(12) United States Patent
Bates et al.

(10) Patent No.: US 9,383,364 B2
(45) Date of Patent: Jul. 5, 2016

(54) PREDICTIVE MARKER OF DNMT1 INHIBITOR THERAPEUTIC EFFICACY AND METHODS OF USING THE MARKER

(75) Inventors: Paula J. Bates, Louisville, KY (US); Mohammad Tariq Malik, Prospect, KY (US); Francesca R. Salipur, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/003,714

(22) PCT Filed: Mar. 7, 2012

(86) PCT No.: PCT/US2012/027982
§ 371 (c)(1),
(2), (4) Date: Apr. 16, 2014

(87) PCT Pub. No.: WO2012/122219
PCT Pub. Date: Sep. 13, 2012

(65) Prior Publication Data
US 2014/0329911 A1     Nov. 6, 2014

Related U.S. Application Data

(60) Provisional application No. 61/450,051, filed on Mar. 7, 2011.

(51) Int. Cl.
| | |
|---|---|
| *A61K 31/215* | (2006.01) |
| *A61K 31/22* | (2006.01) |
| *G01N 33/574* | (2006.01) |
| *C12Q 1/68* | (2006.01) |
| *A61K 31/045* | (2006.01) |
| *C07K 16/18* | (2006.01) |
| *G01N 33/53* | (2006.01) |

(52) U.S. Cl.
CPC .......... *G01N 33/5748* (2013.01); *A61K 31/045* (2013.01); *C07K 16/18* (2013.01); *C12Q 1/6886* (2013.01); *C12Q 2600/106* (2013.01); *C12Q 2600/158* (2013.01); *G01N 33/53* (2013.01)

(58) Field of Classification Search
CPC .............................. A61K 31/045; G01N 33/53
USPC ................................................. 514/529, 546
See application file for complete search history.

(56) References Cited

U.S. PATENT DOCUMENTS

| | | | |
|---|---|---|---|
| 4,018,802 A | 4/1977 | Cragoe, Jr. et al. | |
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,223,409 A | 6/1993 | Ladner et al. | |
| 6,387,901 B1 | 5/2002 | Chupak | |
| 8,207,381 B2 * | 6/2012 | Hammond et al. | ........... 568/843 |
| 8,703,829 B2 * | 4/2014 | Hammond et al. | ........... 514/745 |
| 2008/0188570 A1 | 8/2008 | Hammond et al. | |
| 2010/0028364 A1 | 2/2010 | Brown et al. | |

FOREIGN PATENT DOCUMENTS

| | | |
|---|---|---|
| AU | 2008/213666 B2 | 8/2008 |
| CA | 1064961 A1 | 10/1979 |
| DE | 10029709 A1 | 1/2002 |
| JP | 51125020 A | 11/1976 |
| WO | 90/02809 A1 | 3/1990 |
| WO | 91/17271 A1 | 11/1991 |
| WO | 92/01047 A1 | 1/1992 |
| WO | 92/09690 A2 | 6/1992 |
| WO | 92/15679 A1 | 9/1992 |
| WO | 92/18619 A1 | 10/1992 |
| WO | 92/20791 A1 | 11/1992 |
| WO | 93/01288 A1 | 1/1993 |
| WO | 01/96262 A1 | 12/2001 |
| WO | 2007/093657 A2 | 8/2007 |
| WO | 2007/096576 A1 | 8/2007 |
| WO | 2008/098077 A2 | 8/2008 |
| WO | 2010/056993 A2 | 5/2010 |

OTHER PUBLICATIONS

Australian App. No. 2008213666, Examiner's First Report dated Jan. 30, 2012, 3 pp.
Australian App. No. 2008213666, Patent Examination Report No. 2 dated Mar. 26, 2013, 6 pp.
EP App 08729198.5 Communication Article 94(3) EPC dated Apr. 19, 2013, 3pp.
Japanese App. No. 2009-549221, Office Action, dated Apr. 16, 2013, 5 pp. (English language translation).
PCT/US12/027982 ISR and WO mailed Jun. 20, 2012, 9 pp.
PCT/US2008/053214, International Search Report and Written Opinion, mailed Oct. 22, 2008, 18 pp.
U.S. Appl. No. 12/027,154, Advisory Action dated Oct. 1, 2010, 3 pp.
U.S. Appl. No. 12/027,154, Final Office action dated May 24, 2010, 10 pp.

(Continued)

*Primary Examiner* — Kevin E Weddington
(74) *Attorney, Agent, or Firm* — Calfee, Halter & Griswold LLP; Harry J. Guttman

(57) ABSTRACT

Provided herein are methods for predicting efficacy of a DNA (cytosine-5)-methyltransferase 1 (DNMT1) inhibitor treatment in a subject having a cancer, methods of identifying a subject having a cancer that is more likely to respond to a DNMT1 inhibitor treatment, and methods of selecting a treatment for a subject having a cancer that include determining a level of SOX9 in a sample containing cells from a subject having a cancer. Also provided are methods of treating a subject having a cancer that include selectively administering a DNMT1 inhibitor to a subject having cancer determined to have an elevated level of SOX9 in a sample containing cells from the subject compared to a reference level. Also provided are antibodies and antigen-binding antibody fragments that specifically bind to SOX9, and nucleic acid sequences that contain at least 10 nucleotides complementary to a contiguous sequence present in a SOX9 nucleic acid for use in these methods.

14 Claims, 14 Drawing Sheets

(56) References Cited

OTHER PUBLICATIONS

U.S. Appl. No. 12/027,154, Non-Final Office action dated Nov. 13, 2009, 8 pp.
U.S. Appl. No. 12/027,154, Notice of Allowance with Examiner's Amendment dated Feb. 28, 2012, 17 pp.
U.S. Appl. No. 12/027,154, Restriction Requirement dated Aug. 11, 2009, 10 pp.
Abdel-Samad et al., "MiniSOX9, a dominant-negative variant in colon cancer cells" Oncogene (2011) vol. 30, No. 22, pp. 2493-2503.
Acevedo et al., "Inducible FGFR-1 activation leads to irreversible prostate adenocarcinoma and an epithelial-to-mesenchymal transition" Cancer Cell (2007) vol. 12, pp. 559-571.
Afonja et al., "RAR agonists stimulate SOX9 gene expression in breast cancer cell lines: evidence for a role in retinoid-mediated growth inhibition" Oncogene (2002) vol. 21, No. 51, pp. 7850-7860.
Aitken et al., "Synthesis of Linear Alkynes from Other Alkynes" Science of Synthesis (2008) vol. 43, pp. 555-630.
Aleman et al., "Identification of DNA hypermethylation of SOX9 in association with bladder cancer progression using CpG microarrays" British Journal of Cancer (2008) vol. 98, pp. 466-473.
Altschul et al., Nucleic Acids Research (1997) vol. 25, pp. 3389-3402.
American Cancer Society. Cancer Facts and Figures 2010.
Andre et al., "Oxalipalatin, Fluorouracil, and Leucovorin as Adjuvant Treatment for Colon Cancer" New England Journal of Medicine (2004) vol. 350, pp. 2343-2351.
Andres et al., "Relationships of ESR1 and XBP1 expression in human breast carcinoma and stromal cells isolated by laser capture microdissection compared to intact breast cancer tissue" Endocrine (2011) vol. 40, No. 2, pp. 212-221.
Andrianasolo et al., "DNA methyl transferase inhibiting halogenated monoterpenes from the Madagascar red marine alga Portieria hornemannii" J Nat Prod. (2006) vol. 69, No. 4, pp. 576-579.
Annunziata et al., "PARP inhibitors in BRCA1/BRCA2 germline mutation carriers with ovarian and breast cancer" Biol Rep. (2010) vol. 2, No. 10. (4 pages).
Baniwal et al., "Runx2 transcriptome of prostate cancer cells: insights into invasiveness and bone metastasis" Mol. Cancer (2010) vol. 9, No. 258. (18 pages).
Baranwal et al., "Molecular characterization of the tumor-suppressive function of nischarin in breast cancer" J Natl Cancer Inst. (2011) vol. 103, No. 20, pp. 1513-1528.
Battioni et al., "3-Lithiopropargyl halides as alkynylating reagents" Bullentin De Las Societe Chimique de France (1969) No. 3, pp. 911-914.
Battioni et al., "3-Lithiopropargyl halides as alkynylating reagents" Bullentin De Las Societe Chimique de France (1969) No. 3, pp. 911-914; Chemical Abstracts Services, Columbus, Ohio, US, STN Database accession No. 1969:50025y (vol. 71, 1969); English-language abstract. (1 page).
Baylin et al., "Epigenetic gene silencing in cancer—a mechanism for early oncogenic pathway addiction?" Nat. Rev. Cancer (2006) vol. 6, pp. 107-116.
Beck et al., "M-type phospholipase A2 receptor as target antigen in idiopathic membranous nephropathy" N Engl J. Med. (2009) vol. 361, No. 1, pp. 11-21.
Benaim et al., "Reactions of acetylene chlorohydrin with complex anions of molybdenum and manganese; formation of eta.3-bonded .alpha.-methylenelactones" Journal of Organometallic Chemistry (1979) vol. 165, No. 2, pp. C28-C32.
Bertucci et al., "Breast cancer revisited using DNA array-based gene expression profiling" Int J Cancer. (2003) vol. 103, No. 5, pp. 565-571.
Bessard et al., "Ring Opening of gem-Dihalocyclopropanes: Novel Types of 1,4 Elimination Reactions" Tetrahedron (1990) vol. 46, No. 15, pp. 5230-5236.
Bonkhoff et al., "From pathogenesis to prevention of castration resistant prostate cancer" Prostate (2010) vol. 70, No. 1, pp. 100-112.
Bratthauer et al., "Intracellular location of the SOX9 protein in breast disease" The Open Journal of Pathology (2009) vol. 3, pp. 118-123.
Brillon et al., "Synthesis of 11-and 12-membered rings by direct cyclization method" Canadian Journal of Chemistry (1987) vol. 65, No. 43, pp. 43-55.
Buck et al., "Alkylation of 1-alkynes in THF" Tehedron Letters (2001) vol. 42, pp. 5825-5827.
Budman et al., "Identification of potentially useful combinations of epidermal growth factor receptor tyrosine kinase antagonists with conventional cytotoxic agents using median effect analysis" Anticancer Drugs (2006) vol. 17, No. 8, pp. 921-928.
Burton et al., "Facile General Route to Perfluoroalkyl Allenes" Tetrahedron Letters (1990) vol. 31, No. 26, pp. 3699-3702.
Butler et al., "Histone deacetylase inhibitors as therapeutics for polyglutamine disorders" Nature Reviews: Neuroscience (2006) vol. 7, pp. 784-796.
Cajaiba et al., "Sox9 Expression is Not Limited to Chondroid Neoplasms: Variable Occurrence in Other Soft Tissue and Bone Tumors with Frequent Expression by Synovial Sarcomas" Int J Surg Pathol. (2010) vol. 18, No. 5, pp. 319-323.
Carey et al., "Triple-negative breast cancer: disease entity or title of convenience?" Nat Rev Clin Oncol. (2010) vol. 7, No. 12, pp. 683-692.
Chakravarty et al., "Cytoplasmic compartmentalization of SOX9 abrogates the growth arrest response of breast cancer cells that can be rescued by trichostatin a treatment" Cancer Biol Ther. (2011) vol. 11, No. 1, pp. 71-83.
Chakravarty et al., "Prognostic significance of cytoplasmic SOX9 in invasive ductal carcinoma and metastatic breast cancer" Exp. Biol. Med. (2011) vol. 236, pp. 145-155.
Chambers, "MDA-MB-435 and M14 cell lines: identical but not M14 melanoma?" Cancer Res. (2009) vol. 13, pp. 5292-5293.
Cole et al., "The EVV-Hybridoma Technique and Its Application to Human Lung Cancer" from UCLA Symposia on Molecular and Cellular Biology New Series, vol. 27, Section II—Human-Human Hybridomas, [Roche-UCLA Symposium on "Monoclonal Antibodies and Cancer Therapy"] (Copyright 1985) Alan R. Liss, Inc., New York, NY, pp. 77-96.
Cox, George W., "Assay for Macrophage-Mediated Anti-Tumor Cytotoxicity" from Current Protocols in Immunology, Supplement 84 (1994) Edited by Coligan et al. (Copyright 1994) John Wiley & Sons, Inc., Hoboken, NJ, Units 14.7.1-14.7.10.
Cummins et al., "Quantitative mass spectrometry of diabetic kidney tubules identifies GRAP as a novel regulator of TGF-beta signaling" Biochim Biophys Acta. (2010) vol. 1804, No. 4, pp. 653-661.
Thomsen et al., "Sox9 is required for prostate development" Dev. Biol. (2008) vol. 316, pp. 302-311.
Thomsen et al., "The role of Sox9 in prostate development" Differentiation (2008) vol. 76, pp. 728-735.
Uriarte et al., "Comparison of proteins expressed on secretory vesicle membranes and plasma membranes of human neutrophils" J Immunol. (2008) vol. 180, No. 8, pp. 5575-5581.
van Hoesel et al., "Primary tumor classification according to methylation pattern is prognostic in patients with early stage ER-negative breast cancer" Breast Cancer Res Treat. (2012) vol. 131, No. 3, pp. 859-869.
Vidal et al., "SOX9 expression is a general marker of basal cell carcinoma and adnexal-related neoplasms" J Cutan Pathol. (2008) vol. 35, No. 4, pp. 373-379.
Vige et al., "Sexual dimorphism in non-Mendelian inheritance" Pediatr Res (2008) vol. 63, No. 4, pp. 340-347.
Vizniowski et al., "Propargyl Chlorides as Sources for Cobalt Stabilized gamma-Carbonyl Cations" Journal of Organometallic Chemistry (1995) vol. 60, pp. 7496-7502.
Voskoglou-Nomikos et al., "Clinical predictive value of the in vitro cell line, human xenograft, and mouse allograft preclinical cancer models" Clin Cancer Res. (2003) vol. 9, No. 11, pp. 4227-4239.
Wahnon et al., "Mechanism-based Inhibition of an Essential Bacterial Adenine DNA Methyltransferase: Rationally Designed Antibiotics" J. Am. Chem. Soc. (2001) vol. 123, pp. 976-977.
Walker et al., "Do molecularly targeted agents in oncology have reduced attrition rates?" Nat Rev Drug Discov. (2009) vol. 8, No. 1, pp. 15-16.
Wang et al., "A simple Method for Profiling miRNA Expression" Methods Mol. Biol. (2008) vol. 414, pp. 183-190.

(56) References Cited

OTHER PUBLICATIONS

Wang et al., "SOX9 is expressed in human fetal prostate epithelium and enhances prostate cancer invasion" Cancer Res. (2008) vol. 68, pp. 1625-1630.
Wang et al., "SOX9 is expressed in normal prostate basal cells and regulates androgen receptor expression in prostate cancer cells" Cancer Res. (2007) vol. 67, No. 2, pp. 528-536.
Wigginton et al., "Complete regression of established spontaneous mammary carcinoma and the therapeutic prevention of genetically programmed neoplastic transition by IL-12/pulse IL-2: induction of local T cell infiltration, Fas/Fas ligand gene expression, and mammary epithelial apoptosis" J Immunol. (2001) vol. 166, No. 2, pp. 1156-1168.
Wittliff et al., "Molecular signatures of estrogen receptor-associated genes in breast cancer predict clinical outcome" Adv Exp Med Biol. (2008) vol. 617, pp. 349-357.
Workman et al., "Minimally Invasive Pharmacokinetic and Pharmacodynamic Technologies in Hypothesis-Testing Clinical Trials of Innovative Therapies" J Natl Cancer Inst. (2006) vol. 98, No. 9, pp. 580-598.
Xu et al., "A new convenient synthesis of propargylic fluorohydrins and 2,5-diunsubstituted furans form fluoropropargyl chloride" J. Org. Chem, American Chemical Society (2006a) vol. 71, pp. 3518-3521.
Xu et al., "An efficient synthesis of difluoropropargyl bromides" Synthesis (2006b) vol. 5, pp. 803-806.
Yanai et al., "Indium(III) triflate catalyzed tandem azidation/1,3-dipolar cycloaddition reaction of omega,omega-dialkoxyalkyne derivatives with trimethylsilyl azide" Tetrahedron Letters (2005) vol. 46, pp. 8639-8643.
Yang et al., "Inflammatory gene expression in OVE26 diabetic kidney during the development of nephropathy" Nephron Exp Nephrol (2011) vol. 119: e8-e20.
Yang et al., "MicroRNA-145 Regulates Chondrogenic Differentiation of Mesenchymal Stem Cells by Targeting Sox9" PLoS One (2011) vol. 6, No. 7, e21679. (11 pages).
Yang et al., "Targeting DNA methylation for epigenetic therapy" Trends Pharmacol. Sci. (2010) vol. 31, No. 11, pp. 536-546.
Yasui et al., "Transcriptome dissection of gastric cancer: identification of novel diagnostic and therapeutic targets from pathology specimens" Pathol Int. (2009) vol. 59, pp. 121-136.
Yilmaz et al., "Pten dependence distinguishes haematopoietic stem cells from leukaemia-initiating cells" Nature (2006) vol. 441, pp. 475-482.
Yin et al., "Profiling microRNA expression with microarrays" Trends in Biotechnology (2008) vol. 26, No. 2, pp. 70-76.
Yoo et al., "Epigenetic therapy of cancer: past, present and future" Nat Rev Drug Discov. (2006) vol. 5, pp. 37-50.
Zhou et al., "Clinical significance of SOX9 in human non-small cell lung cancer progression and overall patient survival" Journal of Experimental & Clinical Cancer Research (2012) vol. 31, No. 18. (9 pages).
Cummins et al., "Use of quantitative mass spectrometry analysis in kidney research" Semin Nephrol. (2007) vol. 27, No. 6, pp. 574-583.
Dallas, "Aberrant over-expression of a forkhead family member, FOXO1A, in a brain tumor cell line" BMC Cancer (2007) vol. 7, No. 67, doi:10.1186/1471-2407-7-67, 12 pages.
de Bont et al., "Differential expression and prognostic significance of SOX genes in pediatric medulloblastoma and ependymoma identified by microarray analysis" Neuro Oncol. (2008) vol. 10, No. 5, pp. 648-660.
DeFalco et al., "Sex-specific apoptosis regulates sexual dimorphism in the *Drosophila* embryonic gonad" Dev Cell. (2003) vol. 2, pp. 205-216.
Deng et al., "Studies on Highly Steroselective Addition-Elimination Reactions of 3-(Methoycarbonyl)-1,2-allen-4-ols with MX. An Efficient Synthesis of 3-(Methoxycarbonyl)-2-halo-1, 3(Z)-dienes" Journal of Organometallic Chemistry (2007) vol. 72, pp. 5901-5904.

Dong, et al., "FOXO1A is a Candidate for the 13q14 Tumor Supressor Gene Inhibiting Androgen Receptor Signaling in Prostate Cancer" Cancer Res (2006) vol. 66, No. 14, pp. 6998-7006.
Dudley et al., "Calcification of multipotent prostate tumor endothelium" Cancer Cell (2008) vol. 14, No. 3, pp. 201-211.
Duhagon et al., "Genomic profiling of tumor initiating prostatospheres" BMC Genomics (2010) vol. 11, No. 324. (16 pages).
Egorin et al., "In vitro metabolism by mouse and human liver preparations of halomon, an antitumor halogenated monoterpene" Cancer Chemother Pharmacol. (1997) vol. 41, No. 1, pp. 9 14.
Egorin et al., "Plasma pharmacokinetics, bioavailability, and tissue distribution in CD2F1 mice of halomon, an antitumor halogenated monoterpene isolated from the red algae Portieria hornemannii" Cancer Chemother Pharmacol. (1996) vol. 39, No. 1-2, pp. 51-60.
Einat, "Methodologies for High-Throughput Expression Profiling of MicroRNAs" Methods Mol. Biol. (2006) vol. 342, pp. 139-157.
Endo et al., "Role of Sox-9, ER81 and VE-Cadherin in retinoic acid-mediated trans-differentiation of breast cancer cells" PLoS Onc. (2008) vol. 3, No. 7, e2714. (11 pages).
Evano, "Product subclass 9: alk-2-ynoic acids" Science of Synthesis (2006) vol. 20a, pp. 507-531.
Feixas et al., "Synthesis of (Z)-10, 10-Difluoro-13-Hexadecen-11-YNYL Acetate, New Difluoro Analogue of the Sex Pheromone of the Processionary Moth" Bioorganic & Medicinal Chemistry Letters (1992) vol. 2, No. 5, pp. 467-470.
Foulkes et al., "Triple-negative breast cancer" N Engl J Med. (2010) vol. 363, No. 20, pp. 1938-1948.
Fuchs et al., "Targeting Recombinant Antibodies to the Surface of *Escherichia coli*: Fusion to a Peptidoglycan Associated Lipoprotein" BioTechnology (1991) vol. 9, pp. 1370-1372.
Fuller et al., "A pentahalogenated monoterpene from the red alga Portieria hornemannii produces a novel cytotoxicity profile against a diverse panel of human tumor cell lines" J Med Chem. (1992) vol. 35, No. 16, pp. 3007-3011.
Fuller et al., "Isolation and structure/activity features of halomon-related antitumor monoterpenes from the red alga Portieria hornemannii" J Med Chem. (1994) vol. 37, pp. 4407-4411.
Garraway et al., "Lineage dependency and lineage-survival oncogenes in human cancer" Nat. Rev./Cancer (2006) vol. 6, pp. 593-602 plus Erratum (1 page).
Gillmann et al., "Convenient Synthesis of Methyl 2-Bromo-and 2-Iodo-2, 3-Butadiennoates" Synthetic Communications (1994) vol. 24, No. 15, pp. 2133-2138.
Goffin et al., "DNA methyltransferase inhibitors-state of the art" Annals of Oncology (2002) vol. 13, pp. 1699-1716.
Green et al., "The C3(1)/SV40 T-antigen transgenic mouse model of mammary cancer: ductal epithelial cell targeting with multistage progression to carcinoma" Oncogene (2000) vol. 19, pp. 1020-1027.
Griffiths et al., "Human anti-self antibodies with high specificity from phage display libraries" EMBO J. (1993) vol. 12, No. 2, pp. 725-734.
Gupta et al., "Mullerian inhibiting substance suppresses tumor growth in the C3(1)T antigen transgenic mouse mammary carcinoma model" Proc Natl Acad Sci U S A (2005) vol. 102, No. 9, pp. 3219-3224.
Gushchin et al., "Iodine-127 NQR spectra in a series of iodo derivatives of aliphatic compounds" Izvestiya Akademii Nauk SSSR (1983) vol. 8, pp. 1920-1922. (published English Translation of original article in Russian language).
Hammond, "Nucleophilic and electrophilic substitutions of difluoropropargyl bromides" Journal of Fluorine Chemistry (2006) vol. 127, pp. 476-488.
Hamper, "Regioselective Synthesis of 1-Methyl-3-Hydroxy-5-perfluoroalkylpyrazoles by the Addition of Methyhydrazine to Perfluoroalkylacetylenic Esters" Journal of Fluorine Chemistry (1990) vol. 48, pp. 123-131.
Hastie et al., Generalized Additive Models (1990) Chapman and Hall, New York, NY, Chapter 1 (16 pages).
Hay et al., "Bacteriophage cloning and *Escherichia coli* expression of a human IgM Fab" Hum. Antibod. Hybridomas (1992) vol. 3, pp. 81-85.

(56) References Cited

OTHER PUBLICATIONS

Hong et al., "An Efficient Synthesis of Difluoropropargyl Bromides" Synthesis (2006) vol. 5, pp. 803-806.

Huch et al., "Sox9 marks adult organ progenitors" Nat. Genet. (2011) vol. 43, No. 1, pp. 9-10.

Huh et al., "Inhibition of VEGF receptors significantly impairs mammary cancer growth in C3(1)/Tag transgenic mice through antiangiogenic and non-antiangiogenic mechanisms" Oncogene (2005) vol. 24, pp. 790-800.

Huse et al., "Generation of a large combinatorial library of the immunoglobulin repertoire in phage lambda" Science 8 (1989) vol. 246, No. 4935, pp. 1275-1281.

Issa et al., "Targeting DNA methylation" Clin Cancer Res. (2009) vol. 15, No. 12, pp. 3938-3946.

Jakob et al., "Sex determination and the control of Sox9 expression in mammals" FEBS J. (2011) vol. 278, No. 7, pp. 1002-1009.

Jazin et al., "Sex differences in molecular neuroscience: from fruit flies to humans" Nat Rev Neurosci. (2010) vol. 11, No. 1, pp. 9-17.

Jeon et al., "Inhibition of Bovine Plasma Amine Oxidase by 1,4-Diamino-2-butenes and -2-butynes" Bioorganic & Medicinal Chem. (2003) vol. 11, pp. 4631-4641.

Jiang et al., "Upregulation of SOX9 in lung adenocarcinoma and its involvement in the regulation of cell growth and tumorigenicity" Clin Cancer Res. (2010) vol. 16, No. 17, pp. 4363-4373.

Jose et al., "Novel histone deacetylase inhibitors: cyclic tetrapeptide with trifluoromethyl and pentafluoroethyl ketones" Bioorganic & Medicinal Chemistry Letters (2004) vol. 14, pp. 5343-5346.

Kelland, "Of mice and men: values and liabilities of the athymic nude mouse model in anticancer drug development" Eur J Cancer. (2004) vol. 40, No. 6, pp. 827-836.

Kerr et al., "A five-gene model predicts clinical outcome in ER+/PR+, early-stage breast cancers treated with adjuvant tamoxifen" Horm Cancer. (2011) vol. 2, No. 5, pp. 261-271.

Khleif et al., "AACR-FDA-NCI Cancer Biomarkers Collaborative. AACR-FDA-NCI Cancer Biomarkers Collaborative consensus report: advancing the use of biomarkers in cancer drug development" Clin Cancer Res. (2010) vol. 16, No. 13, pp. 3299-3318.

Kidd et al., "Angiogenesis-associated sequence variants relative to breast cancer recurrence and survival" Cancer Causes Control (2010) vol. 21, No. 10, pp. 1545-1557.

Kohler et al., "Continuous cultures of fused cells secreting antibody of predefined specificity" Nature (1975) vol. 256, pp. 495-497.

Kozbor et al., "The production of monoclonal antibodies from human lymphocytes" Immunol. Today (1983) vol. 4, No. 3, p. 72-79.

Kwok et al., "Total Synthesis of 7,7-, 10,10-, and 13,13-Difluoroarachidonic Acids" J. Am. Chem. Soc. (1987) vol. 109, pp. 3684-3692.

Lan et al., "An Efficient Preparation of TIPS-Halofluoropropyane and its Application to the Diastereoselective synthesis of Propargylic Fluorohydrins" J. Org. Chem., American Chemical Society (2000) vol. 65, No. 13, pp. 4217-4221.

Le Coq, "Synthesis and properties of 3,4-epoxy-1, 1-dichloro-1-butene and trichlorotetrolaldehyde" Annales De Chimie (Paris, France) (1968) vol. 3, No. 6, pp. 529-541.

Lee et al., "Inhibition of DNA methylation by caffeic acid and chlorogenic acid, two common catechol-containing coffee polyphenols" Carcinogenesis (2006) vol. 27, No. 2, pp. 269-277.

Lehmann et al. "Identification of human triple-negative breast cancer subtypes and preclinical models for selection of targeted therapies" J. Clin. Invest. (2011) vol. 121, No. 7, pp. 2750-2767.

Linardou et al., "Assessment of somatic k-RAS mutations as a mechanism associated with resistance to EGFR-targeted agents: a systematic review and meta-analysis of studies in advanced non-small-cell lung cancer and metastatic colorectal cancer" Lancet Oncol. (2008) vol. 9, pp. 962-972.

Lis et al., "Synthesis of Aminoprostanoids A and J" Zhurnal Organnicheskoi Khimii (1992) vol. 28, No. 9, pp. 1854-1861.

Lis et al., "Synthesis of Aminoprostanoids A and J" Institute of Bioorganic Chemistry, Belorussian Academy of Sciences, Minsk—an English-language translation published 1993 of an original article printed in the Zhurnal Organnicheskoi Khimii (1992) vol. 28, No. 9, pp. 1854-1861. (6 pages).

Liu et al., "Oncolytic herpes simplex virus vector therapy of breast cancer in C3(1)/SV40 T-antigen transgenic mice" Cancer Res (2005) vol. 65, No. 4, pp. 1532-1540.

Lominadze et al., "Proteomic analysis of human neutrophil granules" Mol Cell Proteomics. (2005) vol. 4, No. 10, pp. 1503-1521.

Lü et al., "Analysis of SOX9 expression in colorectal cancer" Am J Clin Pathol. (2008) vol. 130, pp. 897-904.

Malki et al., "Expression and biological role of the prostaglandin D synthase/SOX9 pathway in human ovarian cancer cells" Cancer Lett. (2007) vol. 255, pp. 182-193.

Maroulakou et al., "Prostate and mammary adenocarcinoma in transgenic mice carrying a rat C3(1) simian virus 40 large tumor antigen fusion gene" Proc Natl Acad Sci U S A (1994) vol. 91, pp. 11236-11240.

Marson, "Structure-activity relationships of aryloxyalkanoic acid hydroxyamides as potent inhibitors of histone deacetylase" Bioorganic & Medicinal Chemistry Letters (2007) vol. 17, pp. 136-141.

Matheu et al., "Oncogenicity of the Developmental Transcription Factor Sox9" Amer Assn for Cancer Research (2012) vol. 72, pp. 1301-1315.

McCabe et al., "Cancer DNA methylation: molecular mechanisms and clinical implications" Clin Cancer Res. (2009) vol. 15, No. 12, pp. 3927-3937.

McCarry et al., "A Facile Synthesis of Muscimol" Tetrahedron Letters (1981) vol. 22, No. 51, pp. 5153-5156.

Merchant et al., "Microfiltration isolation of human urinary exosomes for characterization by MS" Proteomics Clin Appl. (2010) vol. 4, pp. 84-96.

Miller et al., "Integrative genomic analyses of neurofibromatosis tumours identify SOX9 as a biomarker and survival gene" EMBO Mol Med. (2009) vol. 1, pp. 236-248.

Mohammad et al., "Loss of a single Hic1 allele accelerates polyp formation in Apc(Δ716) mice" Oncogene (2011) vol. 30, pp. 2659-2669.

Morgan, "Tetrazolium (MTT) Assay for Cellular Viability and Activity" Methods in Molecular Biology (1998) vol. 79, pp. 179-183.

Mori-Akiyama et al., "SOX9 is required for the differentiation of paneth cells in the intestinal epithelium" Gastroenterology (2007) vol. 133, No. 2, pp. 539-546.

Muller et al., "SOX9 mediates the retinoic acid-induced HES-1 gene expression in human breast cancer cells" Breast Cancer Res Treat. (2010) vol. 120, pp. 317-326.

Needleman et al., "A General Method Application to the Search for Similarities in the Amino Acid Sequence of Two Proteins" J. Mol. Biol. (1970) vol. 48, pp. 443-453.

Nicoll et al., "Expression of the Hypermethylated in Cancer gene (HIC-1) is associated with good outcome in human breast cancer" Br. J. Cancer (2001) vol. 85, pp. 1878-1882.

Okada et al., "Stereoselective construction of functionalized (Z)-fluoroalkenes directed to depsipeptide isosteres" Tetrahedron Letters (2002) vol. 43, pp. 5845-5847.

Ottewell et al., "Differential effect of doxorubicin and zoledronic acid on intraosseous versus extraosseous breast tumor growth in vivo" Clin Cancer Res. (2008) vol. 14, No. 14, pp. 4658-4666.

Passeron et al., "SOX9 is a key player in ultraviolet B-induced melanocyte differentiation and pigmentation" Proc Natl Acad Sci U S A (2007) vol. 104, No. 35, pp. 13984-13989.

Passeron et al., "Upregulation of SOX9 inhibits the growth of human and mouse melanomas and restores their sensitivity to retinoic acid" J Clin Invest. (2009) vol. 119, No. 4, pp. 954-963.

Pathiraja et al., "Epigenetic regulation in estrogen receptor-positive breast cancer-Role in treatment response" J Mammary Gland Biol Neoplasia. (2010) vol. 15, pp. 35-47.

Penaloza et al., "Sex of the cell dictates its response: differential gene expression and sensitivity to cell death inducing stress in male and female cells" FASEB J. (2009) vol. 23, No. 6, pp. 1869-1879.

Piekarz et al., "Epigenetic modifiers: basic understanding and clinical development" Clin. Cancer Res. (2009) vol. 15, pp. 3918-3926.

(56) References Cited

OTHER PUBLICATIONS

Powell et al., "Defining mitogen-activated protein kinase pathways with mass spectrometry-based approaches" Mass Spectrom Rev. (2005) vol. 24, No. 6, pp. 847-864.

Powell et al., "Discovery of regulatory molecular events and biomarkers using 2D capillary chromatography and mass spectrometry" Expert Rev Proteomics. (2006) vol. 3, No. 1, pp. 63-74.

Pritchett et al., "Understanding the role of SOX9 in acquired diseases: lessons from development" Trends Mol. Med. (2011) vol. 17, No. 3, pp. 166-174.

Prud'Homme et al., "Breast cancer stem-like cells are inhibited by a non-toxic aryl hydrocarbon receptor agonist" PLoS One. (2010) vol. 5, No. 11: e13831. (15 pages).

Qi et al., "Siah2-dependent concerted activity of HIF and FoxA2 regulates formation of neuroendocrine phenotype and neuroendocrine prostate tumors" Cancer Cell (2010) vol. 18, No. 1, pp. 23-38.

Radojicic et al., "MicroRNA expression analysis in triple-negative (ER, PR and Her2/neu) breast cancer" Cell Cycle (2011) vol. 10, pp. 507-517.

Richert et al., "Metastasis of hormone-independent breast cancer to lung and bone is decreased by alpha-difluoromethylornithine treatment" Breast Cancer Res. (2005) vol. 7, No. 5, R819-R827.

Rico et al., "Reactivity of the Perhalogenoalkanes CF2BrX (X = Cl, Br) with Nucleophiles. Part 4. Condensation with Carbanions" Journal of the Chemical Society, Perkin Transactions I, Organic and Bio-organic Chemistry (1982) vol. 4, pp. 1063-1065.

Rodriquez et al. "Total Synthesis, NMR Solution Structure, and Binding Model of the Potent Histone Deacetylase Inhibitor FR235222" Angew, Chem. Int. Ed. (2006) vol. 45, pp. 423-427.

Rozen et al., "Bromochlorodifluoromethane" e-EROS Encyclopedia of Reagents for Organic Synthesis (2001). (4 pages).

Santel et al., "Atu027 prevents pulmonary metastasis in experimental and spontaneous mouse metastasis models" Clin Cancer Res. (2010) vol. 16, No. 22, pp. 5469-5480.

Schaeffer et al., "Androgen-induced programs for prostate epithelial growth and invasion arise in embryogenesis and are reactivated in cancer" Oncogene (2008) vol. 27, pp. 7180-7191.

Scott et al., "SOX9 induces and maintains neural stem cells" Nat Neurosci. (2010) vol. 13, No. 10, pp. 1181-1189, plus Methods (1 page) and Supplementary Information (13 pages).

Sharma, et al. "Cell line-based platforms to evaluate the therapeutic efficacy of candidate anticancer agents" Nat Rev/Cancer. (2010) vol. 10, pp. 241-253.

Shin et al., "Global gene expression analysis of very small embryonic-like stem cells reveals that the Ezh2-dependent bivalent domain mechanism contributes to their pluripotent state" Stem Cells Dev. (2012) vol. 21, No. 10, pp. 1639-1652.

Shinji, "Design, synthesis, and evaluation of cyclic amide/imide-bearing hydroxamic acid derivatives as class-selective histone deacetylase (HDAC) inhibitors" Bioorganic & Medicinal Chemistry (2006) vol. 14, pp. 7625-7651.

Shoemaker, et al. "The NCI60 human tumour cell line anticancer drug screen" Nat Rev Cancer. (2006) vol. 6, pp. 813-823.

Shoushtari et al., "Comparing genetically engineered mouse mammary cancer models with human breast cancer by expression profiling" Breast Dis. (2007) vol. 28, pp. 39-51.

Sigalotti et al., "Epigenetic modulation of solid tumors as a novel approach for cancer immunotherapy" Semin. Oncol. (2005) vol. 32, pp. 473-478.

Stange et al., "Expression of an ASCL2 Related Stem Cell Signature and IGF2 in Colorectal Cancer Liver Metastases with 11p15.5 Gain" Gut. (2010) vol. 59, pp. 1236-1244.

Taylor et al., "Exosome isolation for proteomic analyses and Rna profiling" Methods Mol Biol. (2011) vol. 728, pp. 235-246.

Thayer, "Fabulous Fluorine" Chem. Eng. News (2006) vol. 84, No. 23, pp. 15-24.

Thomsen et al., "SOX9 elevation in the prostate promotes proliferation and cooperates with PTEN loss to drive tumor formation" Cancer Res. (2010) vol. 70, No. 3, pp. 979-987, plus Correction, 2 pages.

\* cited by examiner (also known as BX11)

(also known as BX12 or XB-05a)

XB-05b (also known as BX17 or TMO-117)

PREDICTIVE MARKER OF DNMT1 INHIBITOR THERAPEUTIC EFFICACY AND METHODS OF USING THE MARKER

CROSS-REFERENCE TO RELATED APPLICATIONS

This application is a National Stage Entry of International Application No. PCT/US2012/027982 filed Mar. 7, 2012, which is herein incorporated by reference in its entirety, which claims the benefit of U.S. Provisional Application No. 61/450,051, filed Mar. 7, 2011, which is herein incorporated by reference in its entirety.

U.S. GOVERNMENT RIGHTS

The invention was made with Government support under National Institutes of Health contract No. P20RR018733. The Government has certain rights in the invention.

BACKGROUND OF THE INVENTION

Cancer drug development has undergone massive changes during the past decade, largely as a result of targeted therapies that have stemmed from increased understanding of the molecular aspects of cancer. Moreover, we can now assess the molecular driving forces behind each patient's cancer, offering possibilities for individually tailored therapies. Despite advances in the pace of molecular target identification and drug discovery, translation to safe and effective therapies remains challenging. Rates of attrition in cancer drug development are alarmingly high with estimates that at least 80% of oncology drugs entering Phase I clinical trials will not make it to market (Walker et al., *Nat. Rev. Drug Discov.* 8:15-16, 2009). Consequently, the cost of drug development is skyrocketing and a recent analysis set the price of bringing a new drug to market at $0.8-1.0 billion (Walker et al., *Nat. Rev. Drug Discov.* 8:15-16, 2009). To address these issues, experts and regulatory agencies have called for increased use of biomarkers in cancer drug development (Workman et al., *Cancer Res.* 98:580-598, 2006; Khleif et al., *Clin. Cancer Res.* 16:3299-3318, 2010). Arguably, the most useful type of biomarker for drug development will be one that predicts for response to a drug because it will allow patients to be preselected for clinical trials. This should increase the chances of observing a clinical response and thereby reduce the number of patients who need to take part in the trial. Examples of validated predictive biomarkers include HER2 levels to predict response to trastuzumab for breast cancer patients, EGFR mutations that predict response to small molecule EGFR inhibitors in lung cancer, and K-Ras mutations as a contraindication to therapy with EGFR inhibitors in the setting of colon cancer (Linardou et al., *Lancet Oncol.* 9:962-672, 2008). In some cases, the biomarker is the molecular target of the drug, as with HER2. In others, the relationship is indirect—e.g. the increased sensitivity of patients with BRCA mutations to PARP inhibitors due to a "synthetic lethal" effect (Annunziata et al., *Biol Rep.* 2, p. 10, 2010)—or based on purely empirical observations.

Prostate cancer will claim the lives of more than 30,000 American men this year (American Cancer Society Facts and Figures 2010). African American men will be disproportionately represented in this group, being more than twice as likely to die from prostate cancer compared to Caucasian American men (American Cancer Society Facts and Figures 2010). Men who present with localized prostate cancer have an excellent chance for a cure following treatment by surgery and/or radiotherapy, although these treatments can have significant side effects. Men who have regionally advanced or metastic disease at the time of diagnosis often have long-term cancer control when treated by androgen-deprivation therapies (ADT), but cures are rare because the disease inevitably becomes resistant to therapy and progresses to castration-resistant prostate cancer (CRPC). CRPC causes considerable morbidity, notably bone pain and fatigue, and survival is typically 1-3 years. Treatment options for patients with CRPC are limited because the disease is generally resistant to chemotherapies. Docetaxel can produce a modest increase in median survival, but almost all patients will eventually progress. Therefore, there is a clear need in the art for novel therapies that can effectively treat CRPC.

Extensive basic/translational research has revealed many of the biological changes associated with progression to CRPC, by both androgen receptor (AR)-dependent and AR-independent pathways (Bonkhoff et al., *Prostate* 70:100-112, 2010). It is clear that CRPC is a heterogenous disease, so it is unlikely that a "one size fits all" therapy can be developed. However, several pathways have emerged that are frequently upregulated in advanced prostate cancers and these represent targets for development of therapies that should help the majority of men with this disease.

Therefore, what is needed then are markers for identifying patients suffering from prostate and other cancers which can be used to predict the therapeutic efficacy of agents used to treat the disease.

SUMMARY OF THE INVENTION

It has now been discovered that SOX9, a transcription factor that has been implicated in regulating multipotency and differentiation of neural crest stem cells and several tissue stem cells is a marker useful for predicting the efficacy of treatment with XB05 (BX11) and related compounds for patients suffering from a wide variety of cancers such as colon, breast and prostate cancer.

In one aspect, the present invention provides a method for identifying a patient suffering from cancer who will respond to treatment with XB05 (BX11) and related compounds including the steps of providing a sample of cancer cells isolated from said patient and analyzing said cells for SOX9 expression, wherein if SOX9 is expressed in said patient will respond to said treatment.

Provided herein are methods for predicting efficacy of a DNA (cytosine-5)-methyltransferase 1 (DNMT1) inhibitor treatment in a subject having a cancer that include determining a level of SOX9 in a sample containing cells from a subject having a cancer, and predicting increased efficacy of a DNMT1 inhibitor treatment in a subject that has an elevated (e.g., a significant, detectable, or observable increase) level of SOX9 in the sample compared to a reference level, or decreased efficacy of a DNMT1 inhibitor treatment in a subject that has no significant change or a decreased (e.g., a significant, detectable, or observable decrease) level of SOX9 in the sample compared to a reference level. In some embodiments, the reference level is a level of SOX9 in a sample containing cells from a healthy subject. In some embodiments, the sample containing cells is a cancer biopsy sample. In some embodiments, the level of SOX9 in the sample is a level of SOX9 protein in the sample. In some embodiments, the level of SOX9 in the sample is a level of SOX9 mRNA in the sample. In some embodiments, the subject has a cancer selected from the group of: chondrosarcoma cancer, lung cancer, malignant peripheral nerve sheath tumor, prostate cancer, malignant melanoma, a sarcoma, breast cancer, colon cancer, gastric cancer, pancreatic cancer, brain cancer, basal cell carcinoma, liver cancer, leukemia, and myelodysplastic syndrome. Some embodiments further include selecting a subject having a cancer.

In some embodiments, the DNMT1 inhibitor treatment comprises the administration of one or more DNMT1 inhibitors of Formula I

wherein: $R_1$ is carboxy, $(C_1-C_{20})$alkoxycarbonyl, $(C_2-C_{20})$alkenyloxycarbonyl, $(C_{2-20})$alkynyloxycarbonyl, $(C_1-C_{20})$alkyl, $(C_2-C_{20})$alkenyl, or $(C_2-C_{20})$alkynyl, which $(C_{1-20})$alkyl, $(C_2-C_{20})$alkenyl, or $(C_2-C_{20})$alkynyl, is substituted with one or more groups independently selected from halo, hydroxy, mercapto, $(C_1-C_{20})$alkoxy, $(C_2-C_{20})$alkenyloxy, $(C_2-C_{20})$alkynyloxy, aryloxy, heteroaryloxy, $(C_3-C_{20})$cycloalkyloxy, heterocyclyloxy, $(C_1-C_{20})$alkylthio, $(C_2-C_{20})$alkenylthio, $(C_2-C_{20})$alkynylthio, carboxy, $(C_1-C_{20})$alkoxycarbonyl, $(C_2-C_{20})$alkenyloxycarbonyl, $(C_2-C_{20})$alkynyloxycarbonyl, aryl, heteroaryl, cycloalkyl, heterocyclyl, $NR_aR_b$, $(C_2-C_{20})$alkynoyloxy, and arylcarbonyloxy;

$R_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, $CF_2I$, $CFHI$, $C(R_c)(R_d)I$, $CF(R_e)I$ or $CCl_3$;

each $R_a$ and $R_b$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, $(C_2-C_{20})$alkynyloxy, or aryl-$(C_1-C_{20})$alkoxycarbonyl;

each $R_c$ and $R_d$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and $R_e$ is $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;

wherein each aryl, heteroaryl, heterocyclyl, aryloxy, heteroaryloxy, arylcarbonyloxy or heteroarylcarbonyloxy of $R_1$ is optionally substituted with one or more groups independently selected from halo, hydroxy, nitro, cyano, trifluoromethyl, trifluoromethoxy, mercapto, carboxy, $(C_1-C_{20})$alkyl, $(C_2-C_{20})$alkenyl, $(C_2-C_{20})$alkynyl, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, $(C_1-C_{20})$alkoxycarbonyl, $(C_2-C_{20})$alkenyloxycarbonyl, $(C_2-C_{20})$alkynyloxycarbonyl, aryl, heteroaryl, aryl$(C_1-C_{20})$alkyl, heteroaryl$(C_1-C_{20})$alkyl, aryl$(C_2-C_{20})$alkenyl, aryl$(C_2-C_{20})$alkynyl, heteroaryl$(C_2-C_{20})$alkenyl, heteroaryl$(C_2-C_{20})$alkynyl, $(C_1-C_{20})$alkanoyloxy, $(C_2-C_{20})$alkenoyloxy, $(C_2-C_{20})$alkynoyloxy; or a salt thereof.

In some embodiments, the DNMT1 inhibitor treatment comprises the administration of

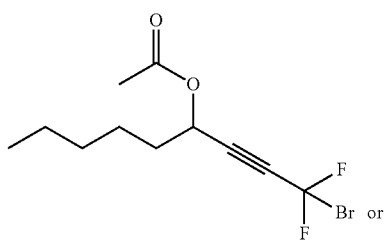

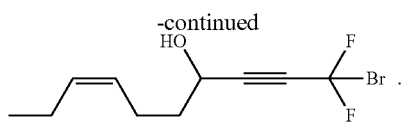

Also provided are methods of identifying a subject having a cancer that is more likely to respond to a DNA (cytosine-5)-methyltransferase 1 (DNMT1) inhibitor treatment that include determining a level of SOX9 in a sample containing cells from a subject having a cancer, and identifying a subject having an elevated level of SOX9 in the sample compared to a reference level as being more likely to respond to a DNMT1 inhibitor treatment. In some embodiments, the reference level is a level of SOX9 in a sample contains cells from a healthy subject. In some embodiments, the sample containing cells is a cancer biopsy sample. In some embodiments, the level of SOX9 in the sample is a level of SOX9 protein in the sample. In some embodiments, the level of SOX9 in the sample is a level of SOX9 mRNA in the sample. In some embodiments, the subject has a cancer selected from the group of: chondrosarcoma cancer, lung cancer, malignant peripheral nerve sheath tumor, prostate cancer, malignant melanoma, a sarcoma, breast cancer, colon cancer, gastric cancer, pancreatic cancer, brain cancer, basal cell carcinoma, liver cancer, leukemia, and myelodysplastic syndrome. Some embodiments further include selecting a subject having a cancer.

In some embodiments, the DNMT1 inhibitor treatment comprises the administration of one or more DNMT1 inhibitors of Formula I

wherein: $R_1$ is carboxy, $(C_1-C_{20})$alkoxycarbonyl, $(C_2-C_{20})$alkenyloxycarbonyl, $(C_{2-20})$alkynyloxycarbonyl, $(C_1-C_{20})$alkyl, $(C_2-C_{20})$alkenyl, or $(C_2-C_{20})$alkynyl, which $(C_{1-20})$alkyl, $(C_2-C_{20})$alkenyl, or $(C_2-C_{20})$alkynyl, is substituted with one or more groups independently selected from halo, hydroxy, mercapto, $(C_1-C_{20})$alkoxy, $(C_2-C_{20})$alkenyloxy, $(C_2-C_{20})$alkynyloxy, aryloxy, heteroaryloxy, $(C_3-C_{20})$cycloalkyloxy, heterocyclyloxy, $(C_1-C_{20})$alkylthio, $(C_2-C_{20})$alkenylthio, $(C_2-C_{20})$alkynylthio, carboxy, $(C_1-C_{20})$alkoxycarbonyl, $(C_2-C_{20})$alkenyloxycarbonyl, $(C_2-C_{20})$alkynyloxycarbonyl, aryl, heteroaryl, cycloalkyl, heterocyclyl, $NR_aR_b$, $(C_2-C_{20})$alkynoyloxy, and arylcarbonyloxy;

$R_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, $CF_2I$, $CFHI$, $C(R_c)(R_d)I$, $CF(R_e)I$ or $CCl_3$;

each $R_a$ and $R_b$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, $(C_2-C_{20})$alkynyloxy, or aryl-$(C_1-C_{20})$alkoxycarbonyl;

each $R_c$ and $R_d$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and $R_e$ is $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;

wherein each aryl, heteroaryl, heterocyclyl, aryloxy, heteroaryloxy, arylcarbonyloxy or heteroarylcarbonyloxy of $R_1$ is optionally substituted with one or more groups independently selected from halo, hydroxy, nitro, cyano, trifluoromethyl, trifluoromethoxy, mercapto, carboxy, (C$_1$-C$_{20}$)alkyl, (C$_2$-C$_{20}$)alkenyl, (C$_2$-C$_{20}$)alkynyl, (C$_1$-C$_{20}$)alkoxy, (C$_2$-C$_{20}$)alkenyloxy, (C$_2$-C$_{20}$)alkynyloxy, (C$_1$-C$_{20}$)alkylthio, (C$_2$-C$_{20}$)alkenylthio, (C$_2$-C$_{20}$)alkynylthio, (C$_1$-C$_{20}$)alkoxycarbonyl, (C$_2$-C$_{20}$)alkenyloxycarbonyl, (C$_2$-C$_{20}$)alkynyloxycarbonyl, aryl, heteroaryl, aryl(C$_1$-C$_{20}$)alkyl, heteroaryl(C$_1$-C$_{20}$)alkyl, aryl(C$_2$-C$_{20}$)alkenyl, aryl(C$_2$-C$_{20}$)alkynyl, heteroaryl(C$_2$-C$_{20}$)alkenyl, heteroaryl(C$_2$-C$_{20}$)alkynyl, (C$_1$-C$_{20}$)alkanoyloxy, (C$_2$-C$_{20}$)alkenoyloxy, (C$_2$-C$_{20}$)alkynoyloxy; or a salt thereof.

In some embodiments, the DNMT1 inhibitor treatment comprises the administration of

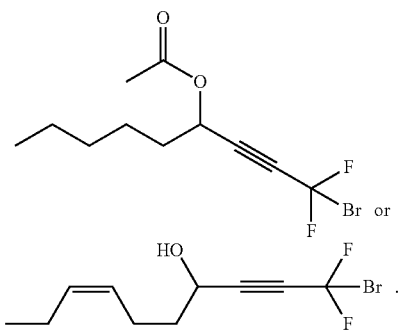

Also provided are methods of selecting a treatment for a subject having a cancer that include determining a level of SOX9 in a sample containing cells from a subject having a cancer, and selecting a DNMT1 inhibitor treatment for a subject having an elevated level of SOX9 in the sample compared to a reference level. In some embodiments, the reference level is a level of SOX9 in a sample containing cells from a healthy subject. In some embodiments, the sample containing cells is a cancer biopsy sample. In some embodiments, the level of SOX9 in the sample is a level of SOX9 protein in the sample. In some embodiments, the level of SOX9 in the sample is a level of SOX9 mRNA in the sample. In some embodiments, the subject has a cancer selected from the group of: chondrosarcoma cancer, lung cancer, malignant peripheral nerve sheath tumor, prostate cancer, malignant melanoma, a sarcoma, breast cancer, colon cancer, gastric cancer, pancreatic cancer, brain cancer, basal cell carcinoma, liver cancer, leukemia, and myelodysplastic syndrome. Some embodiments further include selecting a subject having a cancer.

In some embodiments, the DNMT1 inhibitor treatment includes the administration of one or more DNMT1 inhibitors of Formula I

(I)

wherein: R$_1$ is carboxy, (C$_1$-C$_{20}$)alkoxycarbonyl, (C$_2$-C$_{20}$)alkenyloxycarbonyl, (C$_{2-20}$)alkynyloxycarbonyl, (C$_1$-C$_{20}$)alkyl, (C$_2$-C$_{20}$)alkenyl, or (C$_2$-C$_{20}$)alkynyl, which (C$_{1-20}$) alkyl, (C$_2$-C$_{20}$)alkenyl, or (C$_2$-C$_{20}$)alkynyl, is substituted with one or more groups independently selected from halo, hydroxy, mercapto, (C$_1$-C$_{20}$)alkoxy, (C$_2$-C$_{20}$)alkenyloxy, (C$_2$-C$_{20}$)alkynyloxy, aryloxy, heteroaryloxy, (C$_3$-C$_{20}$)cycloalkyloxy, heterocyclyloxy, (C$_1$-C$_{20}$)alkylthio, (C$_2$-C$_{20}$)alkenylthio, (C$_2$-C$_{20}$)alkynylthio, carboxy, (C$_1$-C$_{20}$)alkoxycarbonyl, (C$_2$-C$_{20}$)alkenyloxycarbonyl, (C$_2$-C$_{20}$)alkynyloxycarbonyl, aryl, heteroaryl, cycloalkyl, heterocyclyl, NR$_a$R$_b$, (C$_2$-C$_{20}$)alkynoyloxy, and arylcarbonyloxy;

R$_2$ is CF$_2$Br, CFHBr, CF$_2$Cl, CFHCl, CFBr$_2$, CFCl$_2$, CBr$_3$, C(R$_c$)(R$_d$)Br, C(R$_c$)(R$_d$)Cl, CF(R$_e$)Br, CF$_2$I, CFHI, C(R$_c$)(R$_d$)I, CF(R$_e$)I or CCl$_3$;

each R$_a$ and R$_b$ is independently H, (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$)alkoxy, (C$_2$-C$_{20}$)alkenyloxy, (C$_2$-C$_{20}$)alkynyloxy, or aryl-(C$_1$-C$_{20}$)alkoxycarbonyl;

each R$_c$ and R$_d$ is independently H, (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$)alkoxy, (C$_2$-C$_{20}$)alkenyloxy, or (C$_2$-C$_{20}$)alkynyloxy; and R$_e$ is (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$)alkoxy, (C$_2$-C$_{20}$)alkenyloxy, or (C$_2$-C$_{20}$)alkynyloxy;

wherein each aryl, heteroaryl, heterocyclyl, aryloxy, heteroaryloxy, arylcarbonyloxy or heteroarylcarbonyloxy of R$_1$ is optionally substituted with one or more groups independently selected from halo, hydroxy, nitro, cyano, trifluoromethyl, trifluoromethoxy, mercapto, carboxy, (C$_1$-C$_{20}$)alkyl, (C$_2$-C$_{20}$)alkenyl, (C$_2$-C$_{20}$)alkynyl, (C$_1$-C$_{20}$)alkoxy, (C$_2$-C$_{20}$)alkenyloxy, (C$_2$-C$_{20}$)alkynyloxy, (C$_1$-C$_{20}$)alkylthio, (C$_2$-C$_{20}$)alkenylthio, (C$_2$-C$_{20}$)alkynylthio, (C$_1$-C$_{20}$)alkoxycarbonyl, (C$_2$-C$_{20}$)alkenyloxycarbonyl, (C$_2$-C$_{20}$)alkynyloxycarbonyl, aryl, heteroaryl, aryl(C$_1$-C$_{20}$)alkyl, heteroaryl(C$_1$-C$_{20}$)alkyl, aryl(C$_2$-C$_{20}$)alkenyl, aryl(C$_2$-C$_{20}$)alkynyl, heteroaryl(C$_2$-C$_{20}$)alkenyl, heteroaryl(C$_2$-C$_{20}$)alkynyl, (C$_1$-C$_{20}$)alkanoyloxy, (C$_2$-C$_{20}$)alkenoyloxy, (C$_2$-C$_{20}$)alkynoyloxy; or a salt thereof.

In some embodiments, the DNMT1 inhibitor treatment includes the administration of

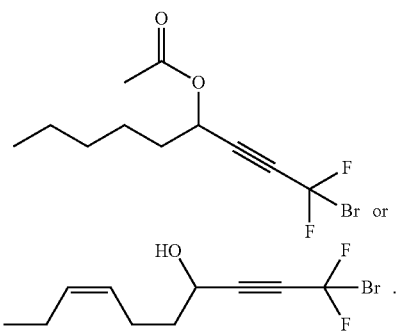

Some embodiments further include administering one or more DNMT1 inhibitors to the subject having a detectable level of SOX9 in the sample. In some embodiments, the one or more DNMT1 inhibitors are one or more DNMT1 inhibitors of Formula I

(I)

wherein: R$_1$ is carboxy, (C$_1$-C$_{20}$)alkoxycarbonyl, (C$_2$-C$_{20}$)alkenyloxycarbonyl, (C$_{2-20}$)alkynyloxycarbonyl, (C$_1$-C$_{20}$)alkyl, (C$_2$-C$_{20}$)alkenyl, or (C$_2$-C$_{20}$)alkynyl, which (C$_1$-20) alkyl, (C$_2$-C$_{20}$)alkenyl, or (C$_2$-C$_{20}$)alkynyl, is substituted with one or more groups independently selected from halo, hydroxy, mercapto, (C$_1$-C$_{20}$)alkoxy, (C$_2$-C$_{20}$)alkenyloxy, (C$_2$-C$_{20}$)alkynyloxy, aryloxy, heteroaryloxy, (C$_3$-C$_{20}$)cycloalkyloxy, heterocyclyloxy, $(C_1-C_{20})$alkylthio, $(C_2-C_{20})$alkenylthio, $(C_2-C_{20})$alkynylthio, carboxy, $(C_1-C_{20})$alkoxycarbonyl, $(C_2-C_{20})$alkenyloxycarbonyl, $(C_2-C_{20})$alkynyloxycarbonyl, aryl, heteroaryl, cycloalkyl, heterocyclyl, $NR_aR_b$, $(C_2-C_{20})$alkynoyloxy, and arylcarbonyloxy;

R$_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, $CF_2I$, $CFHI$, $C(R_c)(R_d)I$, $CF(R_e)I$ or $CCl_3$;

each $R_a$ and $R_b$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, $(C_2-C_{20})$alkynyloxy, or aryl-$(C_1-C_{20})$alkoxycarbonyl;

each $R_c$ and $R_d$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and $R_e$ is $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;

wherein each aryl, heteroaryl, heterocyclyl, aryloxy, heteroaryloxy, arylcarbonyloxy or heteroarylcarbonyloxy of R$_1$ is optionally substituted with one or more groups independently selected from halo, hydroxy, nitro, cyano, trifluoromethyl, trifluoromethoxy, mercapto, carboxy, $(C_1-C_{20})$alkyl, $(C_2-C_{20})$alkenyl, $(C_2-C_{20})$alkynyl, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, $(C_1-C_{20})$alkoxycarbonyl, $(C_2-C_{20})$alkenyloxycarbonyl, $(C_2-C_{20})$alkynyloxycarbonyl, aryl, heteroaryl, aryl$(C_1-C_{20})$alkyl, heteroaryl$(C_1-C_{20})$alkyl, aryl$(C_2-C_{20})$alkenyl, aryl$(C_2-C_{20})$alkynyl, heteroaryl$(C_2-C_{20})$alkenyl, heteroaryl$(C_2-C_{20})$alkynyl, $(C_1-C_{20})$alkanoyloxy, $(C_2-C_{20})$alkenoyloxy, $(C_2-C_{20})$alkynoyloxy; or a salt thereof.

In some embodiments, the DNMT1 inhibitor treatment includes the administration of

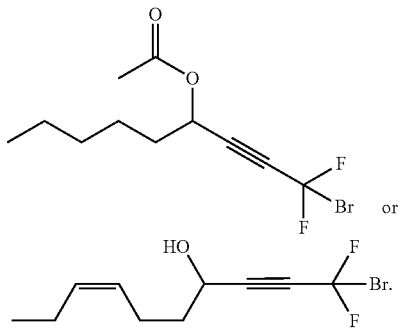

Also provided are methods of treating a subject having a cancer that include selectively administering a DNMT1 inhibitor to a subject having cancer determined to have an elevated level of SOX9 in a sample containing cells from the subject compared to a reference level. In some embodiments, the reference level is a level of SOX9 in a sample containing cells from a healthy subject. In some embodiments, the sample containing cells is a cancer biopsy sample. In some embodiments, the sample is a level of SOX9 protein in the sample. In some embodiments, the level of SOX9 in the sample is a level of SOX9 mRNA in the sample. In some embodiments, the subject has a cancer selected from the group of: chondrosarcoma cancer, lung cancer, malignant peripheral nerve sheath tumor, prostate cancer, malignant melanoma, a sarcoma, breast cancer, colon cancer, gastric cancer, pancreatic cancer, brain cancer, basal cell carcinoma, liver cancer, leukemia, and myelodysplastic syndrome.

In some embodiments, the DNMT1 inhibitor is a DNMT1 inhibitor of Formula I

wherein: R$_1$ is carboxy, $(C_1-C_{20})$alkoxycarbonyl, $(C_2-C_{20})$alkenyloxycarbonyl, $(C_{2-20})$alkynyloxycarbonyl, $(C_1-C_{20})$alkyl, $(C_2-C_{20})$alkenyl, or $(C_2-C_{20})$alkynyl, which $(C_{1-20})$alkyl, $(C_2-C_{20})$alkenyl, or $(C_2-C_{20})$alkynyl, is substituted with one or more groups independently selected from halo, hydroxy, mercapto, $(C_1-C_{20})$alkoxy, $(C_2-C_{20})$alkenyloxy, $(C_2-C_{20})$alkynyloxy, aryloxy, heteroaryloxy, $(C_3-C_{20})$cycloalkyloxy, heterocyclyloxy, $(C_1-C_{20})$alkylthio, $(C_2-C_{20})$alkenylthio, $(C_2-C_{20})$alkynylthio, carboxy, $(C_1-C_{20})$alkoxycarbonyl, $(C_2-C_{20})$alkenyloxycarbonyl, $(C_2-C_{20})$alkynyloxycarbonyl, aryl, heteroaryl, cycloalkyl, heterocyclyl, $NR_aR_b$, $(C_2-C_{20})$alkynoyloxy, and arylcarbonyloxy;

R$_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, $CF_2I$, $CFHI$, $C(R_c)(R_d)I$, $CF(R_e)I$ or $CCl_3$;

each $R_a$ and $R_b$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, $(C_2-C_{20})$alkynyloxy, or aryl-$(C_1-C_{20})$alkoxycarbonyl;

each $R_c$ and $R_d$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and $R_e$ is $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;

wherein each aryl, heteroaryl, heterocyclyl, aryloxy, heteroaryloxy, arylcarbonyloxy or heteroarylcarbonyloxy of R$_1$ is optionally substituted with one or more groups independently selected from halo, hydroxy, nitro, cyano, trifluoromethyl, trifluoromethoxy, mercapto, carboxy, $(C_1-C_{20})$alkyl, $(C_2-C_{20})$alkenyl, $(C_2-C_{20})$alkynyl, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, $(C_1-C_{20})$alkoxycarbonyl, $(C_2-C_{20})$alkenyloxycarbonyl, $(C_2-C_{20})$alkynyloxycarbonyl, aryl, heteroaryl, aryl$(C_1-C_{20})$alkyl, heteroaryl$(C_1-C_{20})$alkyl, aryl$(C_2-C_{20})$alkenyl, aryl$(C_2-C_{20})$alkynyl, heteroaryl$(C_2-C_{20})$alkenyl, heteroaryl$(C_2-C_{20})$alkynyl, $(C_1-C_{20})$alkanoyloxy, $(C_2-C_{20})$alkenoyloxy, $(C_2-C_{20})$alkynoyloxy; or a salt thereof.

In some embodiments, the DNMT1 inhibitor is

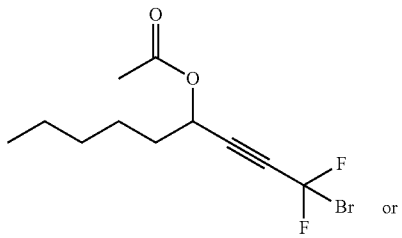

-continued

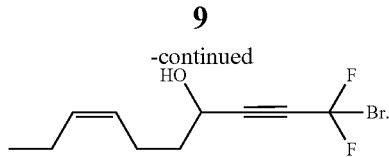

Some embodiments further include determining a level of SOX9 in a sample containing cells from a subject having a cancer.

Also provided are antibodies and antigen-binding antibody fragments that bind specifically to a SOX9 protein for use in any of the methods described herein.

Also provided are nucleic acid sequences that contain at least 10 nucleotides, that are complementary to a contiguous sequence present in a SOX9 nucleic acid for use in any of the methods described herein.

Also provided are kits containing one or more of these antibodies, antigen-binding antibody fragments, and nucleic acid sequences, and instructions for using the one or more antibodies, antigen-binding antibody fragments, and nucleic acid sequences in any of the methods described herein. In some embodiments, the one or more antibodies or antigen-binding antibody fragments are provided in an enzyme-linked immunosorbent assay (ELISA).

As used herein, the term "SOX9 expression" refers to detectable levels of SOX9 protein or mRNA. Most normal (e.g. non-cancerous) tissues do not express any appreciable levels of SOX9 protein or mRNA.

By the term "DNA (cytosine-5)-methyltransferase 1 (DNMT1) inhibitor" is meant a molecule that decreases (e.g., a significant, observable, or detectable decrease) the activity of DNMT1 (e.g., decreases the activity of DNMT1 in a mammalian cell, e.g., a mammalian cancer cell). Non-limiting examples of DNMT1 inhibitors are described herein (e.g., XB05 (BX11) related compounds). Additional, non-limiting examples of DNMT1 inhibitors are described in Yang et al., *Trends Pharmacol. Sci.* 31:536-546, 2010 (e.g., 5-azacytidine, 5-aza-2'-deoxycytidine, 5,6-dihydro-5-azacytidine, zebularine, 5-fluoro-2'-deoxycytidine, NPEOC-DAC, 5110, hydralazine, RG108, procainamide, and SGI-1027). Additional examples of DNMT1 inhibitors are known in the art. Non-limiting examples of methods for determining the activity DNMT1 are described herein. Additional methods for determining the activity of DNMT1 are known in the art.

"XB05 related compounds" are disclosed in International application WO 2008/098077 A2, published on Aug. 14, 2008. XB05a (BX12) is particularly preferred for use in the present invention. The chemical structures of XB05 (BX11), XB05a (BX12), and XB05b (BX17) are shown in FIG. 1.

By the term "DNMT1 inhibitor treatment" is meant the administration of one or more DNMT1 inhibitors to a mammal (e.g., a mammal having cancer). Non-limiting examples of DNMT1 inhibitor treatment are described herein. Additional examples of DNMT1 inhibitor treatment are known in the art.

By the term "SOX9" is meant a mammalian (e.g., human) SOX9 protein or a nucleic acid encoding a mammalian (e.g., human) SOX9 protein (e.g., a SOX9 mRNA). Non-limiting examples of SOX9 proteins and SOX9 nucleic acids are described herein.

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
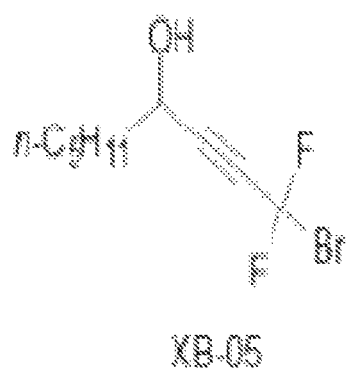
FIG. 1 shows the structure of XB05 (BX11), XB05a (BX12), and XB05b (BX17).
Figure 1:
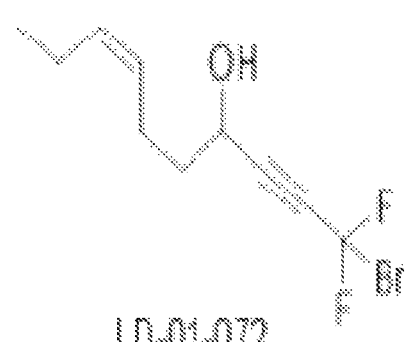
Figure 1:
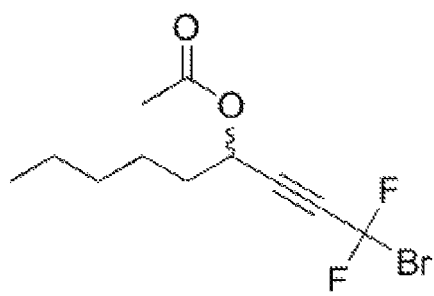

The present invention is based on the unexpected discovery that SOX9 expression can be used as a marker to predict the efficacy of the antitumor activity of XB05 (BX11) and related compounds in patients suffering from a wide variety cancers such as colon, breast and prostate cancer. The prospect that cells that express detectable levels of SOX9 will be selectively killed by XB05 (BX11) and related compounds is especially relevant to men with prostate cancer, because SOX9 is frequently expressed in aggressive and recurrent prostate cancers (see, e.g., Thomsen et al., Cancer Res. 70:979-987, 2010; Wang et al., Cancer Res. 68:1625-1630, 2008; Thomsen et al., Dev. Biol. 316:302-311, 2008; Avevedo et al., Cancer Cell 12:559-571, 2007; Wang et al., Cancer Res. 67:528-536, 2007; Baniwal et al., Mol. Cancer. 9:258, 2010; Qi et al., Cancer Cell 18:23-38, 2010); Schaeffer et al., Oncogene 27:7180-7191, 2008; Dudley et al., Cancer Cell 14:201-211, 2008; and Thomsen et al., Differentiation 76:728-735, 2008). Recently SOX9 has been implicated in various cancers (see Table 1).

TABLE 1

SOX9 and Its Role in Prostate Cancer

Expression is higher in recurrent human tumors (after failure of ADT) than in primary tumors (Wang et al., Cancer Res. 67: 528-536, 2007).
In human specimens (n = 880, Gleason 4-10), 46% had SOX9 staining; there was a positive correlation with Gleason score (Thomsen et al., Cancer Res. 70: 979-987, 2010).
Expression is associated with epithelial-mesenchymal transition (EMT) (Avevedo et al., Cancer Cell 12: 559-571, 2007).
Increased in prostate cancers with neuroendrocrine differentitation (Qi et al., Cancer Cell 18: 23-38, 2010).
High levels in metastatic tumors in a mouse model of prostate cancer (Avevedo et al., Cancer Cell 12: 559-571, 2007).
Suggested role in prostate cancer metastasis to bone (Baniwal et al., Mol. Cancer 9: 258, 2010).
Expressed in most prostate cancer cell lines (Wang et al., Cancer Res. 67: 528-536, 2007).
Required for prostate formation during development and expressed in normal
prostate basal cells in adult men (Wang et al., Cancer Res. 68: 1625-1630, 2008; Thomsen et al., Dev. Biol. 316: 302-311, 2008; Wang et al., Cancer Res. 67: 528-536, 2007; Schaeffer et al., Oncogene 27: 7180-7191, 2008; Thomsen et al., Differentiation 76: 728-735, 2008).
Regulates androgen receptor (AR) expression (Wang et al., Cancer Res. 67: 528-536, 2007).
Cooperates with PTEN loss to drive prostate tumorigenesis in a transgenic mouse model of prostate cancer (Thomsen et al., Cancer Res. 70: 979-987, 2010).
Upregulated in prostate tumor endothelium that has TABLE 1-continued SOX9 and Its Role in Prostate Cancer undergone EMT (Dudley et al., Cancer Cell 14: 201-211, 2008).
SOX9-transfected prostate cancer cells have increased growth, angiogenesis, and invasion in vivo; SOX9 shRNA reduces growth (Wang et al., Cancer Res. 68: 1625-1630, 2008).

The availability of a predictive marker for response to antitumor therapy will greatly expedite clinical development of drugs (such as XB05a (BX12), an optimized analog of XB05 (BX11)) for treating cancer and will allow pre-selection of patients most likely to respond. Thus, new treatments could be available in clinical trial settings within a relatively short period of time.

Some of the methods provided herein include the steps of providing a sample of cells isolated from a patient suffering from cancer and analyzing the cells for the expression of SOX9, where if SOX9 is expressed in the patient's cancer cells, the patient will respond to the treatment.

Also provided herein are methods for predicting efficacy of a DNA (cytosine-5)-methyltransferase 1 (DNMT1) inhibitor treatment in a subject having a cancer, methods of identifying a subject having a cancer that is more likely to respond to a DNMT1 inhibitor treatment, and methods of selecting a treatment for a subject having a cancer that include determining a level of SOX9 in a sample containing cells from a subject having a cancer. Also provided are methods of treating a subject having a cancer that include selectively administering a DNMT1 inhibitor to a subject having cancer determined to have an elevated level of SOX9 in a sample containing cells from the subject compared to a reference level. Also provided are antibodies and antigen-binding antibody fragments that specifically bind to SOX9, and nucleic acid sequences that contain at least 10 nucleotides complementary to a contiguous sequence present in a SOX9 nucleic acid for use in these methods. Various non-limiting aspects of these methods, antibodies, antigen-binding antibody fragments, and nucleic acids are described below.

Cancers

Provided herein are methods for predicting efficacy of a DNMT1 inhibitor treatment in a subject having a cancer, methods of identifying a subject having a cancer that is more likely to respond to a DNMT1 inhibitor treatment, and methods of selecting a treatment for a subject having a cancer that include determining a level of SOX9 in a sample containing cells from a subject having a cancer. Also provided are methods of treating a subject having a cancer that include selectively administering a DNMT1 inhibitor to a subject having cancer determined to have an elevated level of SOX9 in a sample containing cells from the subject compared to a reference level.

In some embodiments, the subject has chondrosarcoma cancer, lung cancer, malignant peripheral nerve sheath tumor, prostate cancer, malignant melanoma, a sarcoma, breast cancer, colon cancer, gastric cancer, or pancreatic cancer. In some embodiments, the subject has already been diagnosed as having a cancer. In some embodiments, the subject can present with one or more (e.g., two or more, or three or more) symptoms of a cancer (e.g., persistent fatigue, unintentional weight loss, pain, bowel changes, chronic cough, lump or thickening that can be felt under the skin, yellowing, darkening, or redness of the skin, difficulty swallowing, hoarseness, and persistent indigestion). In some non-limiting embodiments, the subject has a cancer is selected from the group of prostate cancer, lung adenocarcinoma, colon cancer, gastric carcinoma, basal cell carcinoma, malignant peripheral nerve sheath tumors, breast cancer, malignant melanoma, and a sarcoma.

A subject can be diagnosed or identified as having a cancer by the observation or detection of one or more symptoms of cancer in a subject (e.g., one or more of the symptoms described herein or other symptoms of cancer known in the art). In some embodiments, the subject is diagnosed or identified as having a cancer through the use of imaging (e.g., X-ray, ultrasound, computed tomograph, and magnetic resonance imaging).

DNMT1 Inhibitors

As described herein a DNMT1 inhibitor has the ability to decrease the activity or level of DNMT1 (e.g., the ability to decrease the activity or level of DNMT1 in a mammalian (e.g., human) cell, e.g., in a mammalian (e.g., human) cancer cell).

Non-limiting examples of DNMT1 inhibitors are described in U.S. Patent Application Publication No. 2008/0188570 (incorporated by reference in its entirety). In some embodiments, a DNMT1 inhibitor is a DNMT1 inhibitor of Formula I

wherein:

R$_1$ is carboxy, (C$_1$-C$_{20}$)alkoxycarbonyl, (C$_2$-C$_{20}$)alkenyloxycarbonyl, (C$_{2-20}$)alkynyloxycarbonyl, (C$_1$-C$_{20}$)alkyl, (C$_2$-C$_{20}$)alkenyl, or (C$_2$-C$_{20}$)alkynyl, which (C$_{1-20}$)alkyl, (C$_2$-C$_{20}$)alkenyl, or (C$_2$-C$_{20}$)alkynyl, is substituted with one or more groups independently selected from halo, hydroxy, mercapto, (C$_1$-C$_{20}$)alkoxy, (C$_2$-C$_{20}$)alkenyloxy, (C$_2$-C$_{20}$)alkynyloxy, aryloxy, heteroaryloxy, (C$_3$-C$_{20}$)cycloalkyloxy, heterocyclyloxy, (C$_1$-C$_{20}$)alkylthio, (C$_2$-C$_{20}$)alkenylthio, (C$_2$-C$_{20}$)alkynylthio, carboxy, (C$_1$-C$_{20}$)alkoxycarbonyl, (C$_2$-C$_{20}$)alkenyloxycarbonyl, (C$_2$-C$_{20}$)alkynyloxycarbonyl, aryl, heteroaryl, cycloalkyl, heterocyclyl, NR$_a$R$_b$, (C$_2$-C$_{20}$)alkynoyloxy, and arylcarbonyloxy;

R$_2$ is CF$_2$Br, CFHBr, CF$_2$Cl, CFHCl, CFBr$_2$, CFCl$_2$, CBr$_3$, C(R$_c$)(R$_d$)Br, C(R$_c$)(R$_d$)Cl, CF(R$_e$)Br, CF$_2$I, CFHI, C(R$_c$)(R$_d$)I, CF(R$_e$)I or CCl$_3$;

each R$_a$ and R$_b$ is independently H, (C$_1$-C$_{20}$)alkyl, (C$_1$-C$_{20}$)alkanoyl, (C$_2$-C$_{20}$ alkenylcarbonyl, (C$_2$-C$_{20}$)alkynylcarbonyl, (C$_1$-C$_{20}$)alkoxy, (C$_2$-C$_{20}$)alkenyloxy, (C$_2$-C$_{20}$)alkynyloxy, or aryl-(C$_1$-C$_{20}$)alkoxycarbonyl;

each R$_c$ and R$_d$ is independently H, (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$)alkoxy, (C$_2$-C$_{20}$)alkenyloxy, or (C$_2$-C$_{20}$)alkynyloxy; and R$_e$ is (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$)alkoxy, (C$_2$-C$_{20}$)alkenyloxy, or (C$_2$-C$_{20}$)alkynyloxy;

wherein each aryl, heteroaryl, heterocyclyl, aryloxy, heteroaryloxy, arylcarbonyloxy or heteroarylcarbonyloxy of R$_1$ is optionally substituted with one or more groups independently selected from halo, hydroxy, nitro, cyano, trifluoromethyl, trifluoromethoxy, mercapto, carboxy, (C$_1$-C$_{20}$)alkyl, (C$_2$-C$_{20}$)alkenyl, (C$_2$-C$_{20}$)alkynyl, (C$_1$-C$_{20}$)alkoxy, (C$_2$-C$_{20}$)alkenyloxy, (C$_2$-C$_{20}$)alkynyloxy, (C$_1$-C$_{20}$)alkylthio, (C$_2$-C$_{20}$)alkenylthio, (C$_2$-C$_{20}$)alkynylthio, (C$_1$-C$_{20}$)alkoxycarbonyl, (C$_2$-C$_{20}$)alkenyloxycarbonyl, (C$_2$-C$_{20}$)alkynyloxycarbonyl, aryl, heteroaryl, aryl(C$_1$-C$_{20}$)alkyl, heteroaryl(C$_1$-C$_{20}$)alkyl, aryl(C$_2$-C$_{20}$)alkenyl, aryl(C$_2$-C$_{20}$)alkynyl, heteroaryl(C$_2$-C$_{20}$) alkenyl, heteroaryl(C$_2$-C$_{20}$)alkynyl, (C$_1$-C$_{20}$)alkanoyloxy, (C$_2$-C$_{20}$)alkenoyloxy, (C$_2$-C$_{20}$)alkynoyloxy; or a salt thereof.

In some embodiments, the DNMT1 inhibitor is

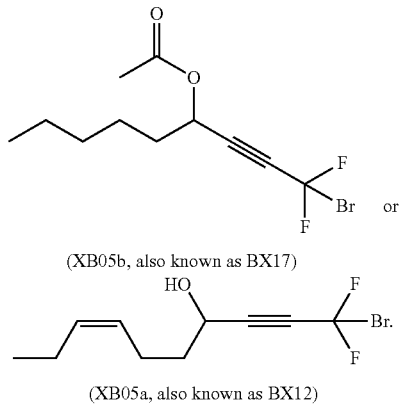

(XB05b, also known as BX17)

(XB05a, also known as BX12)

In some embodiments, the DNMT1 inhibitor is 5-azacytidine (Vidaza™) and decitabine (Dacogen™). In some embodiments, the DNMT1 inhibitor is XB05 (BX11), XB05a (BX12), and related small molecules that have been found to be novel agents for treating a variety of cancers including prostate cancer. Additional non-limiting examples of DNMT1 inhibitors are known in the art. Additional, non-limiting examples of DNMT1 inhibitors are described in Yang et al., *Trends Pharmacol. Sci.* 31:536-546, 2010 (e.g., 5-azacytidine, 5-aza-2'-deoxycytidine, 5,6-dihydro-5-azacytidine, zebularine, 5-fluoro-2'-deoxycytidine, NPEOC-DAC, 5110, hydralazine, RG108, procainamide, and SGI-1027). One or more DNMT1 inhibitors can be administered to the subject in a DNMT1 inhibitor treatment in any combination.

The chemical structure of XB05 (BX11), XB05a (BX12), and XB05b (BX17) are shown in FIG. 1. Additional examples of DNMT1 inhibitors are described in WO 2008/098077 A2, published on Aug. 14, 2008, and U.S. Patent Application Publication No. 2008/0188570 (herein incorporated by reference in its entirety) which disclose the structure, synthesis, and activity of DNMT1 inhibitors for use in the present invention. These compounds were not originally designed as anticancer agents or to inhibit any specific molecular target. Rather, XB05 (BX11) was developed as a reagent that could be used to introduce fluorine-containing groups into other molecules. Carbon-fluorine bonds are present in many pharmaceuticals and are useful because they resemble C—H bonds, yet are metabolically stable (Thayer, *Chem. Eng. News* 84:15-24, 2006). Examples include several of the most widely used drugs e.g. Lipitor™, Prozac™, ciprofloxacin, as well as oncology agents, 5-fluorouracil and gemcitabine.

The discovery of the resemblance of XB05 (BX11) to certain bioactive molecules led to the experiments described herein, were XB05 (BX11) was tested against cancer cells and, consequently, sent to the National Cancer Institute (NCI) for testing in their 60 human tumor cell line screen (referred to as the "NCI 60"). This well-known screen not only assesses the activity and tumor-type selectivity of agents, but can also be a rich source of mechanistic data because the activity of the tested agent can be compared to publicly available data for more than 40,000 other compounds that have been screened (Shoemaker et al., *Nat. Rev. Cancer* 6:813-823, 2006). Furthermore, the cell lines in the screen have been extensively characterized in molecular terms (including microarray analyses), so the results can also be probed for correlations with gene expression and molecular target activity.

Without being limited to any particular theory or mechanism of action, preferred DNMT1 inhibitors used of this invention, including XB05 (BX11) and other DNMT1 inhibitors of Formula I, are believed to have unique and pleiotropic effects that are summarized in Table 2, below. For example, whereas the DNMT1 inhibitor 5-aza causes global DNA methylation, the DNMT1 inhibition of compounds according to Formula I (including, in particular, XB05 (BX11)) is believed to be more selective. In preferred embodiments, a DNMT1 inhibitor of the invention is believed to induce selective demthylation of silcened tumor-suppressor genes.

The rationale for the use of DNMT1 inhibitors to treat cancer is by now well established (Yoo et al., *Nat. Rev. Drug Discov.* 5:37-50, 2006; McCabe et al., *Clin. Cancer Res.* 15:3927-3937, 2009; Piekarz et al., *Clin. Cancer Res.* 15:3918-3926, 2009; Issa et al., *Clin. Cancer Res.* 15; 3938-3946, 2009). It has become clear that epigenetic changes play a major role in the initiation and progression of cancer. Aberrant DNA methylation is now known to occur frequently in cancer cells and leads to selective silencing of tumor-suppressor genes via promoter hypermethylation. Targeting DNA methylation offers an appealing avenue because, unlike genetic mutations, it is potentially reversible and must be maintained (by DNMT1) after each cell division. Without wishing to be bound by theory, it is believed that blocking DNMT1 activity can lead to re-expression of hundreds of tumor-suppressor genes and reversion to a more normal phenotype. The recent FDA approval of two DNMT inhibitors, 5-azacytidine or "5-aza" (Vidaza™) and decitabine (Dacogen™) to treat myelodysplastic syndrome (MDS) has provided further validation for the idea of targeting DNA methylation. These were first developed as cytotoxic agents, but there is strong evidence that, at the dose used to treat MDS, the epigenetic effects of these agents is the major contributor to their clinical activity (Yoo et al., *Nat. Rev. Drug Discov.* 5:37-50, 2006; McCabe et al., *Clin. Cancer Res.* 15:3927-3937, 2009; Piekarz et al., *Clin. Cancer Res.* 15:3918-3926, 2009; Issa et al., *Clin. Cancer Res.* 15; 3938-3946, 2009).

TABLE 2

| XB05's Pleiotropic Effects & Unusual Features |
| --- |
| Discovered by chance to have potent activity (<100 nM) against several cancer cell lines, including prostate cancer. |
| Its profile in the NCI60 screen suggests a unique mechanism. |
| Mimics the activity of a marine natural product (halomon), but is synthetic and can be easily made. |
| Inhibits DNMT activity and reactivates epigenetically-silenced tumor suppressor genes. |
| Distinct from other DNMT inhibitors in several ways, including no effect on global DNA methylation. |
| Induces senescence in cancer cells. |
| Inhibits endothelial cell activity in in vitro assays. |
| An optimized analog has demonstrated antitumor activity, with no obvious side effects, in animal models of cancer. |

XB05 (BX11) has activities that slightly differ from other agents in this class of compounds. This is illustrated not only by the NCI 60 data, but also by the effects of XB05 (BX11) and 5-aza on cancer cells and tumor xenografts (FIG. 7). For example, in contrast to 5-aza (which was used at higher concentrations than XB05 (BX11) because it is less active), XB05 (BX11) had no obvious effect on global DNA methylation. It also had inhibitory effects on endothelial cells in vitro, could induce cellular senescence in cultured cancer cells, and resulted in unusual effects in vivo (central tumor necrosis, giving the appearance of "hollow tumors"), as summarized in Table 1 and illustrated in FIG. 8. XB05 (BX11) and 5-aza may inhibit DNMT activity by different mechanisms.

U.S. Patent Publication No. 2008/0188570 (herein incorporated by reference in its entirety) further discloses more than 50 analogs of XB05 (BX11). Non-limiting examples of DNMT1 inhibitors that can be used in any of the methods described herein can be these analogs of XB05 (BX11). In some embodiments, the DNMT1 inhibitor is XB05a (BX12). In some embodiments, the DNMT1 inhibitor is XB05a (BX12) and the cancer has prostate cancer. XB05a (BX12) has equivalent or better activity in anti-proliferative and DNMT1 inhibition assays compared to XB05 (BX11). In silico ADME analysis indicates XB05a (BX12) has acceptable drug-like properties (its poor aqueous stability was addressed by use of cremaphor/ethanol/NaCl formulation). XB05a (BX12) (i.v. 25 mg/kg/day×21) has been tested as monotherapy or in combination with cisplatin (4×4 mg/kg·p. every 3 days) in the A549 lung cancer xenograft model and compared with 5-aza (at 6 mg/kg, the maximally tolerated dose in this model), as shown in FIG. 7. Statistically, significant tumor growth delay was observed for XB05 (BX11) alone and in combination with cisplatin (FIG. 7). XB05a (BX12) alone was more active than 5-aza alone and had much less toxicity (body weight loss) than 5-aza or cisplatin. In contrast to 5-aza, no significant myelotoxicity was observed for XB05a (BX12) (data not shown).

DNMT1 Inhibitor Treatment

DNMT1 inhibitor treatment includes the administration of one or more DNMT1 inhibitors to a mammal (e.g., a human) (e.g., one or more of any of the DNMT1 inhibitors described herein). In some embodiments, the mammal is a human (e.g. a human having a cancer, e.g., any of the cancers described herein).

In some embodiments, the one or more DNMT1 inhibitors is administered by oral, intravenous, intaarterial, intramuscular, intraperitoneal, or subcutaneous administration. In some embodiments, the one or more DNMT1 inhibitors is administered locally (e.g., into a cancerous cell mass or in a tissue proximal to a cancerous cell mass). In some embodiments where two or more DNMT1 inhibitors are administered to the subject, they are administered as separate compositions (e.g., via the same or a different route of administration (e.g., any of the routes of administration described herein or known in the art). In some embodiments where two or more DNMT1 inhibitors are administered to the subject, the two or more DNMT1 inhibitors are administered in the same composition.

In some embodiments, the DNMT1 inhibitors are formulated for oral, intravenous, intramuscular, intraperitoneal, or subcutaneous administration using methods known in the art (see, e.g., the methods described in U.S. Patent Application Serial No. 2008-0188570, herein incorporated by reference). In some embodiments, the amount of a DNMT1 inhibitor administered to the subject (or the amount of each DNMT1 inhibitor when more than one DNMT1 inhibitor is administered to the subject) in a single dose is, e.g., between 1 mg to 800 mg, 1 mg to 700 mg, 1 mg to 600 mg, 1 mg to 500 mg, 10 mg to 400 mg, 10 mg to 300 mg, 10 mg to 200 mg, 10 mg to 100 mg, 10 mg to 50 mg, 1 mg to 50 mg, 1 mg to 100 mg, 100 mg to 200 mg, 200 mg to 300 mg, 300 mg to 400 mg, 400 mg to 500 mg, 500 mg to 600 mg, and 600 mg to 800 mg. In some embodiments, the subject is administered a dose of one or more DNMT1 inhibitors at least once every two months (e.g., at least once every month, at least once every two weeks, at least once a week, at least twice a week, at least three times a week, at least once a day, at least twice a day, or at least three times a day). In some embodiments, the one or more DNMT1 inhibitors are administered by a medical professional (e.g., local administration, e.g., injection, to a mass of cancer cells in the subject) or are self-administered by the subject a having a cancer.

The periodic administration of one or more DNMT1 inhibitors can take place over a period of time (e.g., at least one week, at least two weeks, at least one month, at least two months, at least six months, and at least one year).

SOX9

SOX9 is a transcription factor that is crucial for multiple aspects of development. As used herein, SOX9 is a mammalian (e.g., human) form of SOX9 protein or a mammalian (e.g., human) SOX9 nucleic acid (e.g., an mRNA). SOX9 can be the full length transcript or a truncated form thereof, e.g., the recently described truncated version (Abdel-Samad et al., Oncogene 2011 Feb. 7, published in advance of print).

In some embodiments, the SOX9 nucleic acid is the wild type human SOX9 mRNA or cDNA of SEQ ID NO: 1. In some embodiments, the SOX9 nucleic acid (e.g., mRNA or cDNA) contains a sequence that is at least 85% (e.g., at least 86%, 87%, 88%, 89%, 90%, 91%, 92%, 93%, 94%, 95%, 96%, 97%, 98%, 99%, or 100% identical) to a wild type mammalian SOX9 nucleic acid (e.g., SEQ ID NO: 1). In some embodiments, the SOX9 nucleic acid (e.g., mRNA or cDNA) contains a contiguous sequence of at least 300 nucleotides (e.g., at least 400, 500, 600, 700, 800, 900, 1000, 1100, 1200, 1300, 1400, 1500, 1600, 1700, 1800, 1900, 2000, 2100, 2200, 2300, 2400, or 2500 nucleotides) that is at least 85% (e.g., at least 86%, 87%, 88%, 89%, 90%, 91%, 92%, 93%, 94%, 95%, 96%, 97%, 98%, 99%, or 100% identical) to a contiguous sequence present within a wild type mammalian (e.g., human) SOX9 nucleic acid (e.g., SEQ ID NO: 1). Methods and compositions for determining the level of a SOX9 nucleic acid are described herein. Additional methods for determining the level of a SOX9 nucleic acid are known in the art.

Additional wild type mammalian SOX9 nucleic acids include, e.g., chimpanzee SOX9 mRNA (SEQ ID NO: 3), dog SOX9 mRNA (SEQ ID NO: 5), and mouse SOX9 mRNA (SEQ ID NO: 7). Additional examples of mammalian SOX9 nucleic acids are known in the art.

In some embodiments, the SOX9 protein is the wild type human SOX9 protein of SEQ ID NO: 2. In some embodiments, the SOX9 protein contains a sequence that is at least 85% (e.g., at least 86%, 87%, 88%, 89%, 90%, 91%, 92%, 93%, 94%, 95%, 96%, 97%, 98%, 99%, or 100% identical) to a wild type mammalian SOX9 protein (e.g., SEQ ID NO: 2). In some embodiments, the SOX9 protein contains a contiguous sequence of at least 50 amino acids (e.g., at least 100, 150, 200, 250, 300, 350, 400, or 450 amino acids) that is at least 85% (e.g., at least 86%, 87%, 88%, 89%, 90%, 91%, 92%, 93%, 94%, 95%, 96%, 97%, 98%, 99%, or 100% identical) to a contiguous sequence present within a wild type mammalian (e.g., human) SOX9 protein (e.g., SEQ ID NO: 2). Methods and compositions for determining the level of a SOX9 protein are described herein. Additional methods for determining the level of a SOX9 protein are known in the art.

Additional examples of mammalian SOX9 proteins include, e.g., chimpanzee SOX9 protein (SEQ ID NO: 4), dog SOX9 protein (SEQ ID NO: 6), and mouse SOX9 protein (SEQ ID NO: 8). Additional examples of mammalian SOX9 proteins are known in the art.

As is known in the art, the comparison of sequences and determination of percent identity between two sequences can be accomplished using a mathematical algorithm. The percent identity between two amino acid sequences is determined using the Needleman and Wunsch ((1970) J. Mol. Biol. 48:444-453) algorithm, which has been incorporated into the GAP program in the GCG software package (available at http://www.gcg.com), using either a Blossum 62 matrix or a PAM250 matrix, and a gap weight of 16 and a length weight of 1. The percent identity between two nucleotide sequences is determined using the GAP program in the GCG software package (available at http://www.gcg.com), using a NWSgapdna.CMP matrix and a gap weight of 40 and a length weight of 1.

In general, percent identity between amino acid sequences referred to herein is determined using the BLAST 2.0 program, which is available to the public at http://www.ncbi.nlm.nih.gov/BLAST. Sequence comparison is performed using an ungapped alignment and using the default parameters (Blossum 62 matrix, gap existence cost of 11, per residue gap cost of 1, and a lambda ratio of 0.85). The mathematical algorithm used in BLAST programs is described in Altschul et al., Nucleic Acids Research 25:3389-3402, 1997.

Determining a Level of SOX9

Some of the methods described herein include determining a level of SOX9 (e.g., SOX9 protein or SOX9 nucleic acid (e.g., mRNA)) in a sample containing cells from a subject having cancer. In some embodiments, the sample is a biopsy sample of tissue from the subject. In some embodiments, the sample contains one or more cancer cells. In some embodiments, the sample contains prostate tissue or breast tissue.

The expression or level of SOX9 can be determined by assaying for the SOX9 protein or mRNA using techniques well known in the art.

Determining a Level of SOX9 Protein

In some embodiments, the expression or level of SOX9 protein can be detected using immunohistochemistry, immunofluorescence, Western blotting, protein chip technology, immunoprecipitation, ELISA assay, or mass spectrometry using standard methods known in the art. These methods can be performed using antibodies or antigen-binding antibody fragments that specifically bind to a mammalian (e.g., human) SOX9 protein. Detection using these antibodies or antigen-binding antibody fragments can be facilitated by coupling the antibody or antigen-binding antibody fragment to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, 35S or $^3H$.

In some embodiments, the level of SOX9 protein in the cytoplasm of cells present in a sample obtained from a subject (e.g., a subject having cancer) is determined. In some embodiments, the number of cells having cytoplasmic expression of SOX9 protein in a sample containing cells from a subject (e.g., a subject having cancer) is determined Cytoplasmic detection of SOX9 protein or detection of a cell having cytoplasmic expression of SOX9 protein can be performed using a variety of methods known in the art (e.g., immunofluorescent microscopy, fluorescence assisted cell sorting, or collection of cytosolic lysate and Western blotting (e.g., ELISA)). Non-limiting exemplary methods for detecting a cytosolic level of SOX9 protein are described in Chakravarty et al., *Exp. Biol. Med.* 236:145-155, 2011.

Antibodies and Antigen-Binding Antibody Fragments

An isolated mammalian SOX9 protein (e.g., SEQ ID NO: 2), or an antigen-binding antibody fragment, can be used as an immunogen to generate antibodies using standard techniques for polyclonal and monoclonal antibody preparation. The full-length SOX9 protein can be used or, alternatively, antigenic peptide fragments can be used as immunogens. The antigenic peptide of a protein comprises at least 8 (e.g., 10, 15, 20, or 30) amino acid residues of the amino acid sequence of a SOX9 polypeptide, and encompasses an epitope of the protein such that an antibody raised against the peptide forms a specific immune complex with the protein.

An immunogen typically is used to prepare antibodies by immunizing a suitable subject (e.g., rabbit, goat, mouse or other mammal). An appropriate immunogenic preparation can contain, for example, a recombinantly expressed or a chemically synthesized polypeptide. The preparation can further include an adjuvant, such as Freund's complete or incomplete adjuvant, or similar immunostimulatory agent.

Polyclonal antibodies can be prepared as described above by immunizing a suitable subject with a SOX9 polypeptide or fragment as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein, Nature 256:495-497, 1975, the human B cell hybridoma technique (Kozbor et al., Immunol. Today 4:72, 1983), the EBV-hybridoma technique (Cole et al., Monoclonal Antibodies and Cancer Therapy, Alan R. Liss, Inc., pp. 77-96, 1985) or trioma techniques. The technology for producing hybridomas is well known (see generally Current Protocols in Immunology, 1994, Coligan et al. (eds.) John Wiley & Sons, Inc., New York, N.Y.). Hybridoma cells producing a monoclonal antibody are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP* Phage Display Kit, Catalog No. 240612). Additionally, examples of methods and reagents particularly amenable for use in generating and screening antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809; Fuchs et al., Bio/Technology 9:1370-1372, 1991; Hay et al., Hum. Antibod. Hybridomas 3:81-85, 1992; Huse et al., Science 246:1275-1281, 1989; Griffiths et al., EMBO J. 12:725-734, 1993.

In some embodiments, the antigen-binding antibody fragment is a Fab fragment, a F(ab')2 fragment, and a scFv fragment. Methods for generating these antibody fragments are known in the art.

Non-limiting antibodies that can be used in the methods described herein are commercially available (e.g., Santa Cruz Catalog #sc-20095 (Sox-9 (H-90)).

Determining a Level of a SOX9 Nucleic Acid

In some embodiments, the level of a SOX9 nucleic acid (e.g., mRNA) can be detected using fluorescence in situ hybridization, Northern blotting, gene chip analysis, and quantitative real-time polymerase chain reaction (qRT-PCR). Additional methods for deterring a level of a SOX9 nucleic acid are known in the art. These methods include the use of a nucleic acid probe or primers that contain a sequence that is complementary to a sequence present in a SOX9 nucleic acid (e.g., mRNA).

In some embodiments, the level of SOX9 mRNA in the cytoplasm of cells present in a sample containing cells obtained from a subject (e.g., a subject having cancer) is determined. In some embodiments, the percentage of cells having cytoplasmic expression of SOX9 mRNA in a sample containing cells obtained from a subject (e.g., a subject having cancer) is determined. Cytoplasmic detection of SOX9 mRNA or detection of a cell having cytoplasmic expression of SOX9 mRNA can be performed using a variety of methods known in the art (e.g., fluorescence in situ hyrbidization or collection of cytosolic lysate and Northern blotting, gene array analysis, or performing RT-PCR).

Probes and Primers

In some embodiments, a primer that can be used to determine the level of a SOX9 nucleic acid in a sample contains a sequence of at least 10 nucleotides (e.g., at least 11, 12, 13, 14, 15, 16, 17, 18, 19, 20, 21, 22, 23, 24, 25, 26, 27, 28, 29, or 30 nucleotides) that is complementary to a contiguous sequence present in a mammalian SOX9 nucleic acid (e.g., SEQ ID NO: 1). In some embodiments, the primer contains a contiguous sequence of at least 10 nucleotides (e.g., at least 11, 12, 13, 14, 15, 16, 17, 18, 19, 20, 21, 22, 23, 24, 25, 26, 27, 28, 29, or 30 nucleotides) that is complementary to a sequence at least 85% identical (e.g., at least 86%, 87%, 88%, 89%, 90%, 91%, 92%, 93%, 94%, 95%, 96%, 97%, 98%, 99%, or 100% identical) to a sequence present within a mammalian SOX9 nucleic acid (e.g., SEQ ID NO: 1). In some embodiments, two primers can be used to amplify a specific region of a SOX9 nucleic acid (e.g., mRNA), e.g., a region of at least 30 nucleotides (e.g., a region of at least 50, 100, 150, or 200 nucleotides).

In some embodiments, a probe can be used to determine the level of SOX9 nucleic acid in a sample. In some embodiments, the probe can contain a sequence of at least 30 nucleotides (e.g., at least 35, 40, 45, 50, 60, 70, 80, 90, or 100 nucleotides) that contains a sequence that is complementary to a contiguous sequence present in a mammalian SOX9 nucleic acid (e.g., mRNA). In some embodiments, the probe contains a contiguous sequence of at least 30 nucleotides (e.g., at least 35, 40, 45, 50, 60, 70, 80, 90, or 100 nucleotides) that is complementary to a sequence at least 85% identical (e.g., at least 86%, 87%, 88%, 89%, 90%, 91%, 92%, 93%, 94%, 95%, 96%, 97%, 98%, 99%, or 100% identical) to a sequence present within a mammalian SOX9 nucleic acid (e.g., SEQ ID NO: 1).

In some embodiments, the probe or primer can be labeled with a detectable material. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S, $^{32}$P, or $^{3}$H.

Methods of Predicting Efficacy of a DNMT1 Inhibitor Treatment

The present invention is based on the discovery that SOX9 expression in cancer cells is correlated with sensitivity to cell killing by XB05 (BX11). The COMPARE algorithm (Andrianasolo et al., *J. Nat. Prod.* 69:576-579, 2006) was used to search for correlations between response to XB05 (BX11) and gene expression using the NCI 60 cell line screen for XB05 (BX11) and the publicly available microarray studies of the NCI 60 panel. A positive correlation (R=0.59) between the LC50 values (concentration required for 50% cell death) and expression of SOX9 was found. High levels of SOX9 expression were associated with high sensitivity to XB05 (BX11) across the 60 cell lines, as shown in FIG. 3. The role of SOX9 in cancer was initially discovered using the commercially available Affymetrix microarray analysis of XB05 (BX11)-treated colon cancer cells, which showed modulation of a large proportion of genes in pathways that are regulated by SOX9, e.g. chondrogenesis, osteogenesis, sex determination, and Wnt signaling (data not shown). A549 lung cancer cells, which have a modest sensitivity to XB05 (BX11), were used to show that SOX9 levels were linked to prostate cancer. It was found that knockdown of SOX9 using a specific siRNA completely blocked XB05's antiproliferative effects (FIG. 2). The experiments have been repeated multiple times and differences are statistically significant (p<0.05).

Thus, provided herein are methods for predicting efficacy of a DNMT1 inhibitor treatment (e.g., any of the DNMT1 inhibitor treatments described herein) in a subject having a cancer that include determining a level of SOX9 (e.g., protein or mRNA) in a sample containing cells from a subject having a cancer, and predicting increased efficacy of a DNMT1 inhibitor treatment in a subject that has an elevated (e.g., a detectable, observable, or significant increase) level of SOX9 in the sample compared to a reference level (e.g., any of the reference levels described herein), or decreased efficacy of a DNMT1 inhibitor treatment in a subject that has no significant change or a decreased (e.g., a detectable, observable, or significant decrease) level of SOX9 in the sample compared to a reference level. In some embodiments, the level of SOX9 is a cytosolic level of SOX9 protein or a cytosolic level of SOX9 mRNA.

Also provided are methods of predicting efficacy of a DNMT1 inhibitor treatment (e.g., any of the DNMT1 inhibitor treatments described herein) in a subject having a cancer that include determining a percentage of cells expressing SOX9 (e.g., a detectable or observable level of SOX9) (e.g., protein or mRNA) in a sample containing cells from a subject having a cancer, and predicting increased efficacy of a DNMT1 inhibitor treatment in a subject that has an elevated (e.g., a detectable, observable, or significant increase) percentage of cells expressing SOX9 in the sample compared to a reference value (e.g., a threshold percentage value or the percentage of cells expressing SOX9 in a sample from a healthy subject or a sample not containing any cancerous cells), or decreased efficacy of a DNMT1 inhibitor treatment in a subject that has a decreased (e.g., a detectable, observable, or significant decrease) percentage of cells expressing SOX9 in the sample compared to a reference value. Also provided are methods of predicting efficacy of a DNMT1 inhibitor treatment (e.g., any of the DNMT1 inhibitor treatments described herein) in a subject having a cancer that include determining a percentage of cells having cytosolic expression of SOX9 (e.g., a detectable or observable level of SOX9) (e.g., protein or mRNA) in a sample containing cells from a subject having a cancer, and predicting increased efficacy of a DNMT1 inhibitor treatment in a subject that has an elevated (e.g., a detectable, observable, or significant increase) percentage of cells having cytosolic expression of SOX9 in the sample compared to a reference value (e.g., a threshold percentage value or the percentage of cells having cytosolic expression of SOX9 in a sample from a healthy subject or in sample not containing any cancerous cells), or decreased efficacy of a DNMT1 inhibitor treatment in a subject that has a decreased (e.g., a detectable, observable, or significant decrease) percentage of cells having cytosolic expression of SOX9 in the sample compared to a reference value. In some embodiments, the reference value is at 0%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, or 90%.

Non-limiting examples of methods for determining the level of SOX9 protein or nucleic acid (e.g., mRNA) are described herein. Methods for determining a percentage of cells having cytosolic expression of SOX9 (e.g., protein or mRNA) are also described herein.

In some embodiments, the sample is a biopsy sample. In some embodiments, the sample contains one or more cancer cells.

In some embodiments, the subject is suspected of having a cancer. In some embodiments, the subject presents with one or more symptoms of a cancer (e.g., any of the symptoms of a cancer described herein and/or symptoms of cancer known in the art). In some embodiments, the level of SOX9 is determined in a sample previously obtained from the subject (e.g., a stored sample). In some embodiments, the subject is diagnosed with a cancer. In some embodiments, the subject has a cancer selected from the group of chondrosarcoma cancer, lung cancer, malignant peripheral nerve sheath tumor, prostate cancer, malignant melanoma, a sarcoma, breast cancer, colon cancer, gastric cancer, or pancreatic cancer.

In some embodiments, the subject is a male. In some embodiments, the subject is a female. In some embodiments, the subject is a child, a teenager, or an adult (e.g., at least 18, 20, 25, 30, 35, 40, 45, 50, 55, 60, 65, 70, 75, 80, 85, 90, or 95 years old).

Some embodiments further include selecting a subject having a cancer. Some embodiments further include selecting a DNMT1 inhibitor treatment for the subject. Some embodiments further include administering one or more DNMT1 inhibitors to the subject (e.g., any of the DNMT1 inhibitors described herein or known in the art).

In some embodiments, the DNMT1 inhibitor treatment is any DNMT1 inhibitor treatment described herein. In some embodiments, the DNMT1 inhibitor treatment is any DNMT1 inhibitor treatment known in the art.

In some embodiments, the reference level is a level of DNMT1 (e.g., protein or nucleic acid (e.g., mRNA)) present in a reference sample containing cells from a healthy subject (e.g., a subject that does not have cancer, a subject that has not been diagnosed as having cancer, or a subject that does not present with any symptoms of a cancer). In some embodiments, the reference level is obtained from a reference sample containing cells from a healthy subject, and cells present in the reference sample and the sample from the subject having cancer are from the same tissue (e.g., breast tissue or prostate tissue). In some embodiments, the reference level is a level of DNMT1 (e.g., protein or nucleic acid (e.g., mRNA)) present in a sample containing only non-cancerous mammalian cells.
Methods of Identifying a Subject Having Cancer that is More Likely to Respond a DNMT1 Inhibitor Treatment Also provided are methods of identifying a subject having cancer that is more likely to respond to a DNMT1 inhibitor treatment that include determining a level of SOX9 in a sample containing cells from a subject having a cancer, and identifying a subject having an elevated level of SOX9 in the sample compared to a reference level as being more likely to respond to a DNMT1 inhibitor treatment.

Also provided are methods of identifying a subject having cancer that is more likely to respond to a DNMT1 inhibitor treatment that include determining a percentage of cells expressing SOX9 (e.g., a detectable or observable level of SOX9) (e.g., protein or mRNA) in a sample containing cells from a subject having a cancer, and identifying a subject having an elevated (e.g., a detectable, observable, or significant increase) percentage of cells expressing SOX9 in the sample compared to a reference value (e.g., a threshold percentage value or the percentage of cells expressing SOX9 in a sample from a healthy subject or a sample not containing any cancerous cells), as being more likely to respond to a DNMT1 treatment. Also provided are methods of identifying a subject having cancer that is more likely to respond to a DNMT1 inhibitor treatment that include determining a percentage of cells having cytosolic expression of SOX9 (e.g., a detectable or observable level of SOX9) (e.g., protein or mRNA) in a sample containing cells from a subject having a cancer, and identifying a subject having an elevated (e.g., a detectable, observable, or significant increase) percentage of cells having cytosolic expression of SOX9 in the sample compared to a reference value (e.g., a threshold percentage value or the percentage of cells having cytosolic expression of SOX9 in a sample from a healthy subject or in sample not containing any cancerous cells), as being more likely to respond to a DNMT1 treatment. In some embodiments, the reference value is at 0%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, or 90%.

Non-limiting examples of methods for determining the level of SOX9 protein or nucleic acid (e.g., mRNA) are described herein. Methods for determining a percentage of cells having cytosolic expression of SOX9 (e.g., protein or mRNA) are also described herein.

In some embodiments, the sample is a biopsy sample. In some embodiments, the sample contains one or more cancer cells.

In some embodiments, the subject is suspected of having a cancer. In some embodiments, the subject presents with one or more symptoms of a cancer (e.g., any of the symptoms of a cancer described herein and/or symptoms of cancer known in the art). In some embodiments, the level of SOX9 is determined in a sample previously obtained from the subject (e.g., a stored sample). In some embodiments, the subject is diagnosed with a cancer. In some embodiments, the subject has a cancer selected from the group of chondrosarcoma cancer, lung cancer, malignant peripheral nerve sheath tumor, prostate cancer, malignant melanoma, a sarcoma, breast cancer, colon cancer, gastric cancer, or pancreatic cancer.

In some embodiments, the subject is a male. In some embodiments, the subject is a female. In some embodiments, the subject is a child, a teenager, or an adult (e.g., at least 18, 20, 25, 30, 35, 40, 45, 50, 55, 60, 65, 70, 75, 80, 85, 90, or 95 years old).

Some embodiments further include selecting a subject having a cancer. Some embodiments further include selecting a DNMT1 inhibitor treatment (e.g., any of the DNMT1 inhibitor treatments described herein) for the subject. Some embodiments further include administering one or more DNMT1 inhibitors to the subject (e.g., any of the DNMT1 inhibitors described herein or known in the art).

In some embodiments, the DNMT1 inhibitor treatment is any DNMT1 inhibitor treatment described herein. In some embodiments, the DNMT1 inhibitor treatment is any DNMT1 inhibitor treatment known in the art.

In some embodiments, the reference level is a level of DNMT1 (e.g., protein or nucleic acid (e.g., mRNA)) present in a reference sample containing cells from a healthy subject (e.g., a subject that does not have cancer, a subject that has not been diagnosed as having cancer, or a subject that does not present with any symptoms of a cancer). In some embodiments, the reference level is obtained from a reference sample containing cells from a healthy subject, and cells present in the reference sample and the sample from the subject having cancer are from the same tissue (e.g., breast tissue or prostate tissue). In some embodiments, the reference level is a level of DNMT1 (e.g., protein or nucleic acid (e.g., mRNA)) present in a sample containing only non-cancerous mammalian cells.
Methods of Selecting a Treatment for a Subject Having Cancer Also provided are methods of selecting a treatment for a subject having a cancer that include determining a level of SOX9 (e.g., protein or nucleic acid (e.g., mRNA)) in a sample comprising cells from a subject having a cancer, and selecting a DNMT1 inhibitor treatment (e.g., any of the DNMT1 inhibitor treatments described herein or known in the art) for a subject having an elevated (e.g., a significant, detectable, or observable increase) level of SOX9 in the sample compared to a reference level.

Also provided are methods of selecting a treatment for a subject having a cancer that include determining a percentage of cells expressing SOX9 (e.g., a detectable or observable level of SOX9) (e.g., protein or mRNA) in a sample containing cells from a subject having a cancer, and selecting a DNMT1 inhibitor treatment (e.g., any of the DNMT1 inhibitor treatments described herein or known in the art) for a subject having an elevated (e.g., a detectable, observable, or significant increase) percentage of cells expressing SOX9 in the sample compared to a reference value (e.g., a threshold percentage value or the percentage of cells expressing SOX9 in a sample from a healthy subject or a sample not containing any cancerous cells). Also provided are methods of selecting a treatment for a subject having a cancer that include determining a percentage of cells having cytosolic expression of SOX9 (e.g., a detectable or observable level of SOX9) (e.g., protein or mRNA) in a sample containing cells from a subject having a cancer, and selecting a DNMT1 inhibitor treatment (e.g., any of the DNMT1 inhibitor treatments described herein or known in the art) for a subject having an elevated (e.g., a detectable, observable, or significant increase) percentage of cells having cytosolic expression of SOX9 in the sample compared to a reference value (e.g., a threshold percentage value or the percentage of cells having cytosolic expression of SOX9 in a sample from a healthy subject or in sample not containing any cancerous cells). In some embodiments, the reference value is at 0%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, or 90%.

Non-limiting examples of methods for determining the level of SOX9 protein or nucleic acid (e.g., mRNA) are described herein. Methods for determining a percentage of cells having cytosolic expression of SOX9 (e.g., protein or mRNA) are also described herein.

In some embodiments, the sample is a biopsy sample. In some embodiments, the sample contains one or more cancer cells.

In some embodiments, the subject is suspected of having a cancer. In some embodiments, the subject presents with one or more symptoms of a cancer (e.g., any of the symptoms of a cancer described herein and/or symptoms of cancer known in the art). In some embodiments, the level of SOX9 is determined in a sample previously obtained from the subject (e.g., a stored sample). In some embodiments, the subject is diagnosed with a cancer. In some embodiments, the subject has a cancer selected from the group of chondrosarcoma cancer, lung cancer, malignant peripheral nerve sheath tumor, prostate cancer, malignant melanoma, a sarcoma, breast cancer, colon cancer, gastric cancer, or pancreatic cancer.

In some embodiments, the subject is a male. In some embodiments, the subject is a female. In some embodiments, the subject is a child, a teenager, or an adult (e.g., at least 18, 20, 25, 30, 35, 40, 45, 50, 55, 60, 65, 70, 75, 80, 85, 90, or 95 years old).

Some embodiments further include selecting a subject having a cancer. Some embodiments further include administering one or more DNMT1 inhibitors to the subject (e.g., any of the DNMT1 inhibitors described herein or known in the art).

In some embodiments, the DNMT1 inhibitor treatment is any DNMT1 inhibitor treatment described herein. In some embodiments, the DNMT1 inhibitor treatment is any DNMT1 inhibitor treatment known in the art.

In some embodiments, the reference level is a level of DNMT1 (e.g., protein or nucleic acid (e.g., mRNA)) present in a reference sample containing cells from a healthy subject (e.g., a subject that does not have cancer, a subject that has not been diagnosed as having cancer, or a subject that does not present with any symptoms of a cancer). In some embodiments, the reference level is obtained from a reference sample containing cells from a healthy subject, and cells present in the reference sample and the sample from the subject having cancer are from the same tissue (e.g., breast tissue or prostate tissue). In some embodiments, the reference level is a level of DNMT1 (e.g., protein or nucleic acid (e.g., mRNA)) present in a sample containing only non-cancerous mammalian cells.

Methods of Treatment

Also provided are methods of treating a subject having a cancer that include selectively administering a DNMT1 inhibitor to a subject having cancer determined to have an elevated (e.g., a significant, observable, or detectable increase) level of SOX9 in a sample containing cells from the subject compared to a reference level (e.g., any of the reference levels described herein). Also provided are methods of treating a subject having a cancer that include selectively administering a DNMT1 inhibitor to a subject having cancer determined to have an elevated (e.g., a significant, observable, or detectable increase) percentage of cells expressing SOX9 in a sample containing cells from the subject as compared to a reference level (e.g., any of the reference levels described herein). Also provided are methods of treating a subject having cancer that include selectively administering a DNMT1 inhibitor to a subject having cancer determined to have an elevated (e.g., a significant, observable, or detectable increase) percentage of cells having cytosolic expression of SOX9 in a sample containing cells from the subject as compared to a reference level (e.g., any of the reference levels described herein).

In some embodiments, the sample is a biopsy sample. In some embodiments, the sample contains one or more cancer cells.

In some embodiments, the subject is suspected of having a cancer. In some embodiments, the subject presents with one or more symptoms of a cancer (e.g., any of the symptoms of a cancer described herein and/or symptoms of cancer known in the art). In some embodiments, the level of SOX9 is determined in a sample previously obtained from the subject (e.g., a stored sample). In some embodiments, the subject is diagnosed with a cancer. In some embodiments, the subject has a cancer selected from the group of chondrosarcoma cancer, lung cancer, malignant peripheral nerve sheath tumor, prostate cancer, malignant melanoma, a sarcoma, breast cancer, colon cancer, gastric cancer, or pancreatic cancer.

In some embodiments, the subject is a male. In some embodiments, the subject is a female. In some embodiments, the subject is a child, a teenager, or an adult (e.g., at least 18, 20, 25, 30, 35, 40, 45, 50, 55, 60, 65, 70, 75, 80, 85, 90, or 95 years old).

In some embodiments, the subject is non-responsive to a prior cancer treatment. In some embodiments, the subject is further administered one or more additional therapeutic agents (e.g., an analgesic and/or a chemotherapeutic). In some embodiments, the subject is previously administered a cancer treatment, and such prior cancer treatment is terminated prior to administering the DNMT1 inhibitor to the subject.

In some embodiments, the DNMT1 inhibitor treatment is any DNMT1 inhibitor treatment described herein (e.g., any of the individual DNMT1 inhibitors described herein, any of the routes of administration, any of the formulations of a DNMT1 inhibitor, any of the frequencies or doses of administration, and/or any of the total time periods of treatment described herein). In some embodiments, the DNMT1 inhibitor is any DNMT1 inhibitor known in the art.

In some embodiments, the reference level is a level of DNMT1 (e.g., protein or nucleic acid (e.g., mRNA)) present in a reference sample containing cells from a healthy subject (e.g., a subject that does not have cancer, a subject that has not been diagnosed as having cancer, or a subject that does not present with any symptoms of a cancer). In some embodiments, the reference level is obtained from a reference sample containing cells from a healthy subject, and cells present in the reference sample and the sample from the subject having cancer are from the same tissue (e.g., breast tissue or prostate tissue). In some embodiments, the reference level is a level of DNMT1 (e.g., protein or nucleic acid (e.g., mRNA)) present in a sample containing only non-cancerous mammalian cells.

Some embodiments further include selecting a subject having a cancer. Some embodiments further include determining a level of SOX9 in a sample containing cells from the subject (e.g., any of the samples from the subject described herein). Non-limiting examples of methods for determining the level of SOX9 (protein or nucleic acid) are described herein. Some embodiments further include selecting or identifying a subject that has an elevated level of SOX9 (protein or nucleic acid) compared to a reference level (e.g., any of the reference levels described herein).

Compositions and Kits

Also provided are antibodies or antigen-binding antibody fragments that specifically bind to a mammalian (e.g., human) SOX9 protein (e.g., SEQ ID NO: 2) (e.g., any of the antibodies or antigen-binding antibody fragments described herein) for use in any of the methods described herein.

Also provided are nucleic acids (e.g., probes and primers) that are capable of hybridizing to a mammalian wild type SOX9 protein (e.g., SEQ ID NO: 1) (e.g., any of the antibodies or antigen-binding fragments described ehrein) for use in any of the methods described herein. In some embodiments, the nucleic acids (e.g., probes and primers) contain a sequence of at least 10 nucleotides that is complementary to a contiguous sequence present in a mammalian SOX9 nucleic acid (e.g., SEQ ID NO: 1) (e.g., any of the probes or primers described herein).

Also provided are kits that contain one or more antibodies or antigen-binding antibody fragments that specifically bind to a mammalian (e.g., human) SOX9 protein and instructions for using the one or more antibodies or antigen-binding antibody fragments in any of the methods described herein.

Also provided are kits that contain one or more nucleic acids that are capable of hybridizing to a mammalian wild type SOX9 nucleic acid (e.g., any of the probes and primers described herein) and instructions for using the one or more nucleic acids in any of the methods described herein.

In some embodiments of any of the compositions and kits described herein, the one or more antibodies, antigen-binding antibody fragments, and nucleic acids can be labeled with a detectable substance (e.g., any of the detectable substances described herein or known in the art).

EXAMPLES

The Examples provided below are intended to further describe the invention without limiting its scope.

Example 1

Levels of SOX9 Expression Determine Response to XB05 (BX11)

A variety of different breast cancer cell lines were treated with 1 μM BX11, and the cytotoxic effect of 1 μM BX11 was determined. The cytotoxicity data for each breast cancer cell line was correlated with the SOX9 level present in each cell line prior to treatment.

In a second set of experiments, HOP92 cells were transfected for 24 hours with 60 nM siRNA against SOX9, control siRNA, or no RNA (mock). Knockdown of SOX9 was confirmed by Western blots (WB). Cells were then treated with XB05 (BX11) as indicated. After 48 hours, the cell number and viability for each sample was determined using an automated cell counter.

Figure 2A:
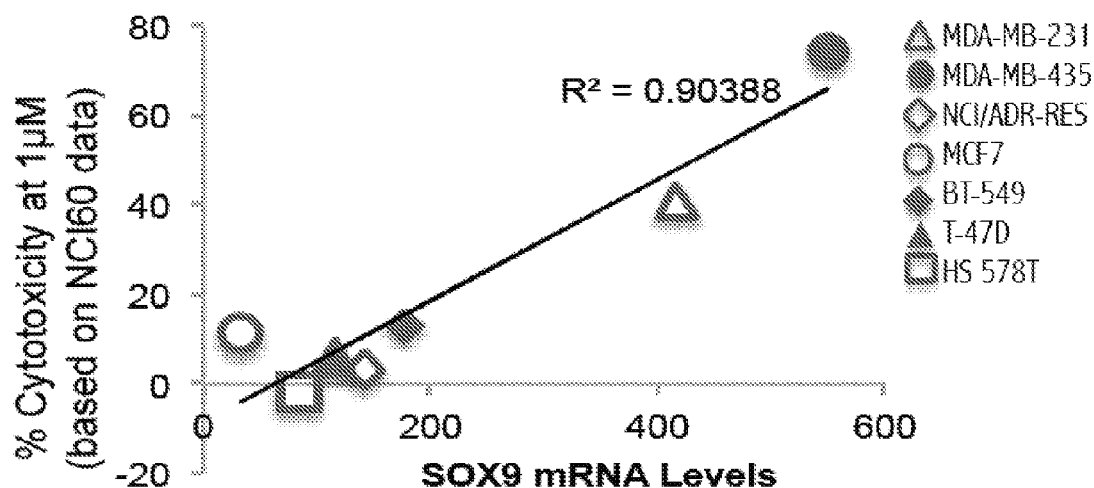
FIG. 2A is a graph showing the correlation between the cytotoxic effect of 1 µM BX11 (also known as XB05a (BX12) or LD-01-072) on various breast cancer cell lines and SOX9 mRNA levels.

The relationship between between BX11 (XB05) activity and SOX9 expression was observed from NC160 data using COMPARE, which show a significant correlation (R=0.58 for 60 cell lines) between the $LC_{50}$ values (concentration of BX11 (XB05) required for 50% cell death) and SOX9 mRNA expression, such that elevated levels of SOX9 were associated with high sensitivity to BX11 (XB05). This same correlation was observed in various breast cancer cell lines (FIG. 2A).

Figure 2B:
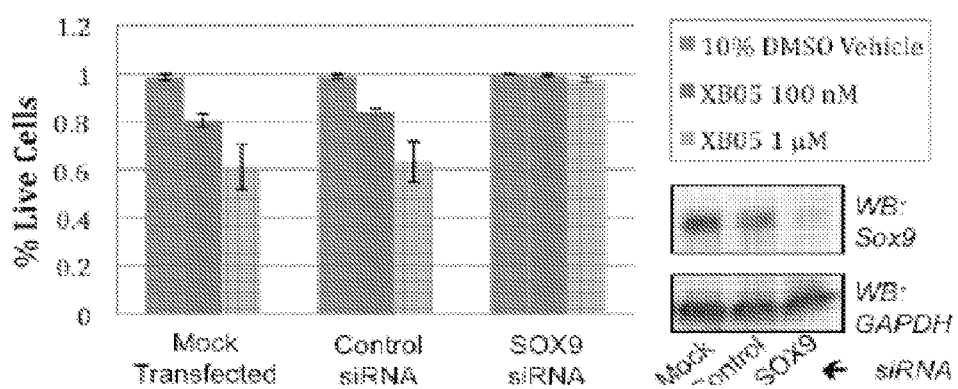
FIG. 2B provides data showing that levels of SOX9 expression determine response to XB05 (BX11).

This relationship between the level of SOX9 and sensitivity to a BX11 (XB05) was also observed in siRNA knockdown experiments. The data from these experiments show that knockdown of SOX9 using a specific siRNA completely blocked XB05's anti-proliferative effects (FIG. 2B).

Example 2

Anti-Proliferative Effects of XB05 (BX11)

Figure 3A:
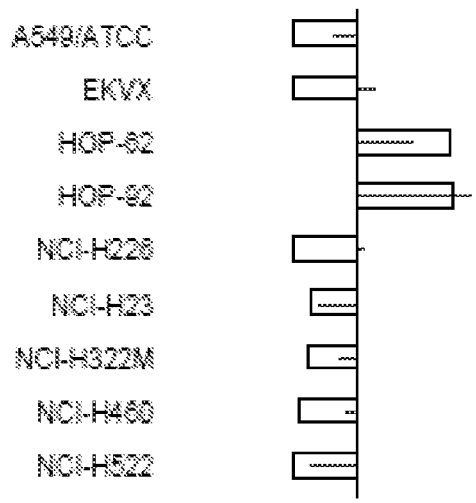
FIG. 3A-3D show that SOX9 expression predicts the response to XB05 (BX11). (3a) results from the NCI 60 cell screen showing a good correlation between the levels of expression of SOX9 and cell death induced by XB05 (BX11); (3b) Western blot showing expression of SOX9 in sensitive cell lines; (3c) clonogenic survival assay in cells sensitive or resistant to XB05 (BX11); (3d) MTT proliferation assays in cells sensitive or resistant to XB05 (BX11).
Figure 3B:
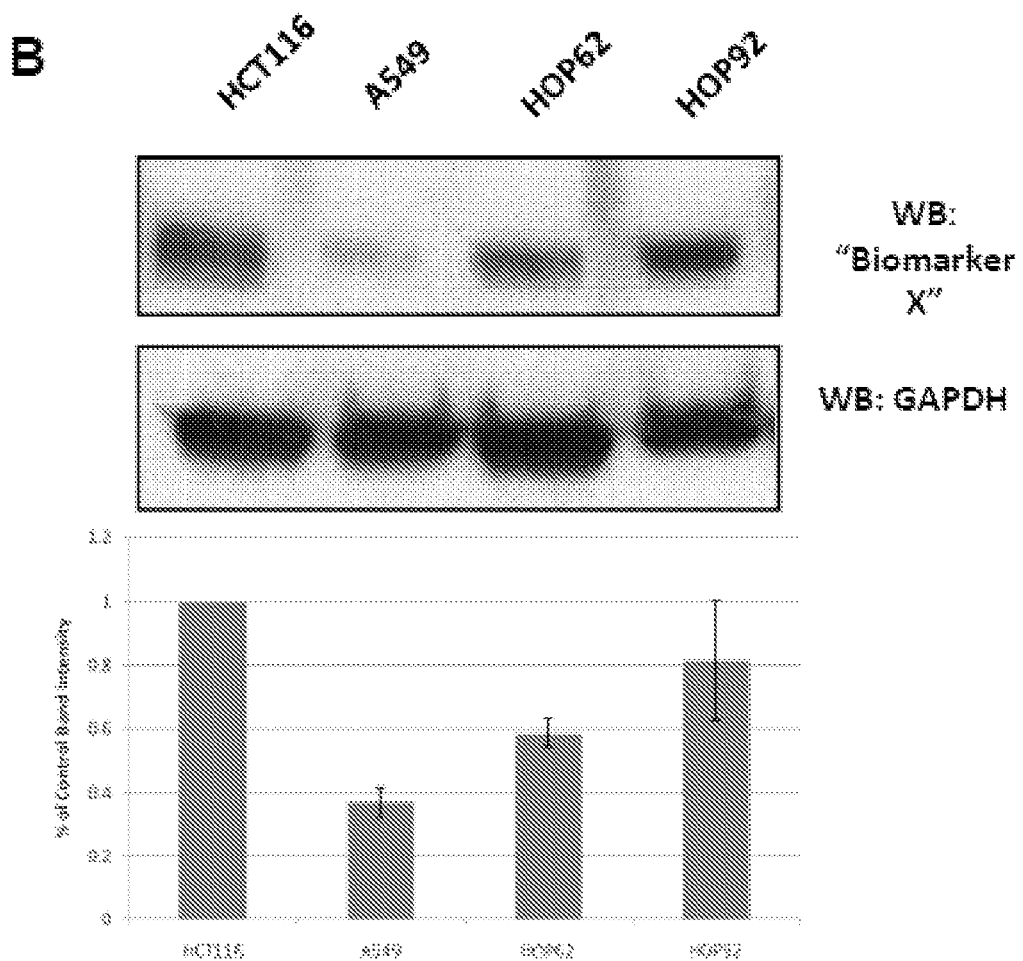
Figure 3C:
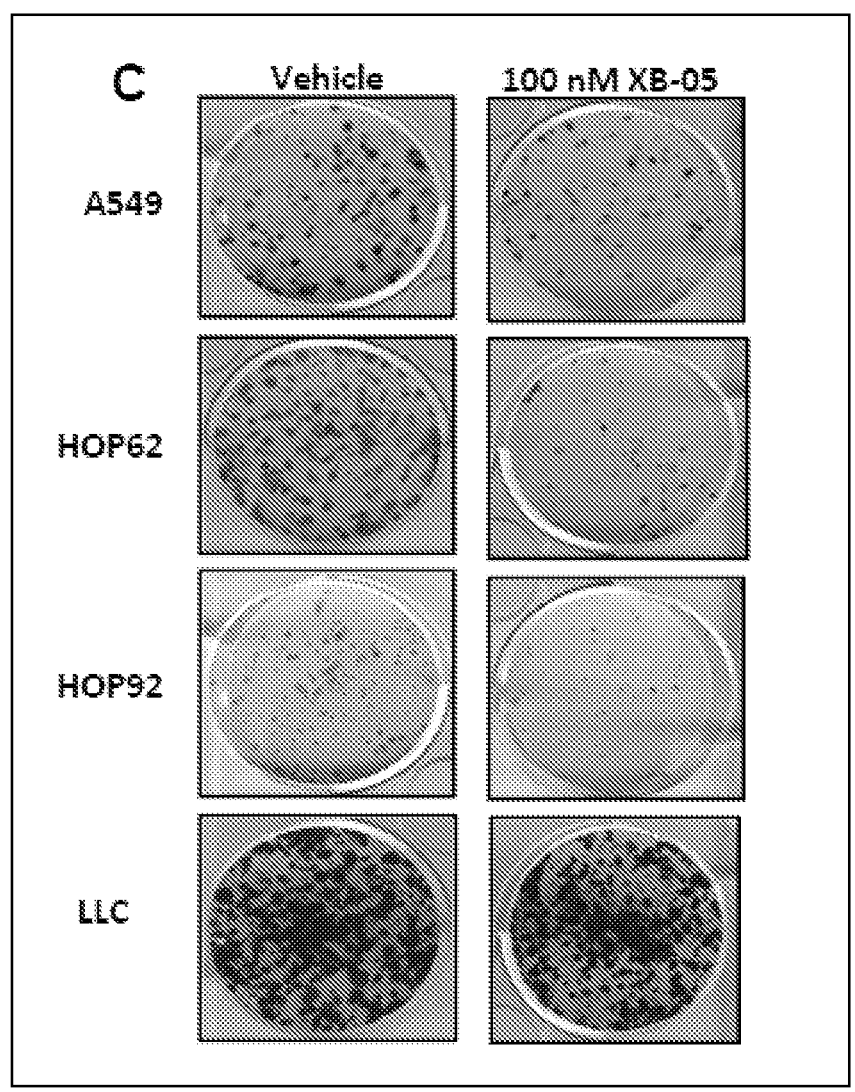
Figure 3D:
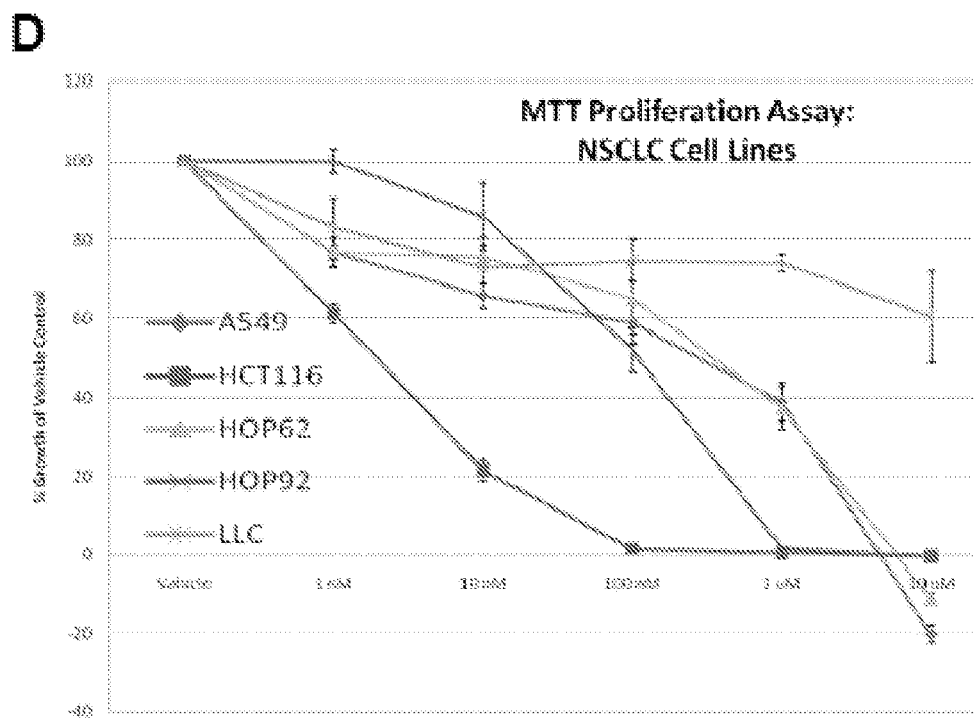

FIG. 3A shows the results from the NCI 60 cell line screen which showed a good correlation between cell death induced by XB05 (BX11) (bars with black outline, indicating relative $LC_{50}$ values) and expression of a gene referred to here as "Biomarker X" (red line, indicating mRNA levels). FIG. 3B are Western blots (WB) confirming expression of Biomarker X (SOX9) protein in the sensitive cell lines. Clonogenic survival assays (FIG. 3C)) and MTT proliferation assays (FIG. 3D) also suggest a correlation between XB05 (BX11) sensitivity and Biomarker X levels. Where indicated, HCT116 cells (colon cancer, sensitive to XB05 (BX11)) and LLC cells (murine lung carcinoma, resistant to XB05 (BX11)) are shown as positive and negative controls, respectively. (SOX9 levels were not assayed in LLC cells because they are of mouse origin).

Example 3

Inhibitory Effects of BX11 on Breast Cancer Cells

Figure 4A:
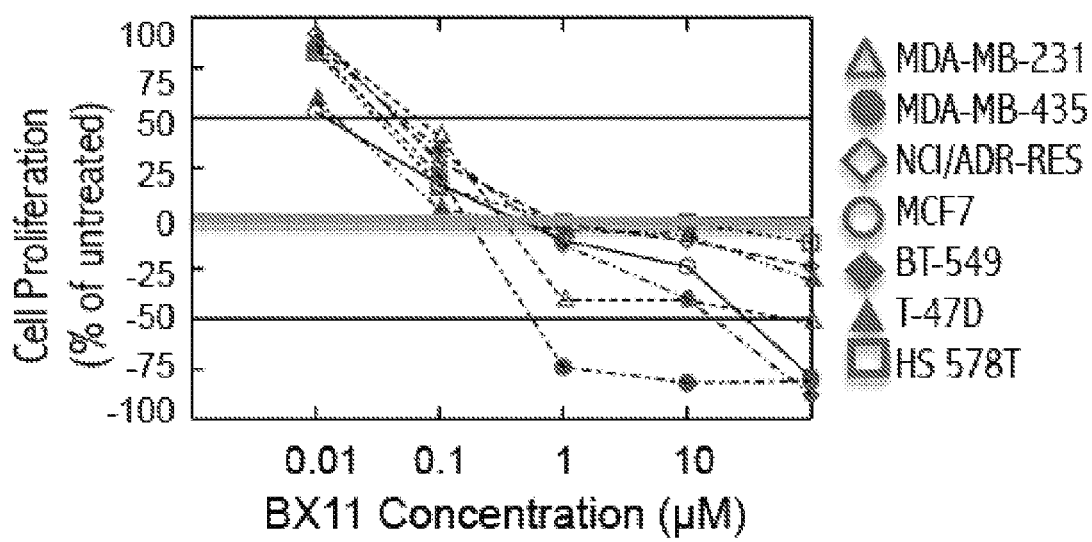
FIG. 4A is NCI60 data showing the effect of XB05 (BX11) on proliferation of various breast cancer cell lines. All cells lines are sensitive to XB05 (BX11) cytostatic effects ($GI_{50}$<100 nM), whereas a few are especially susceptible to cytotoxic effects (e.g., see 1 µM XB05 (BX11) data points).
Figure 4B:
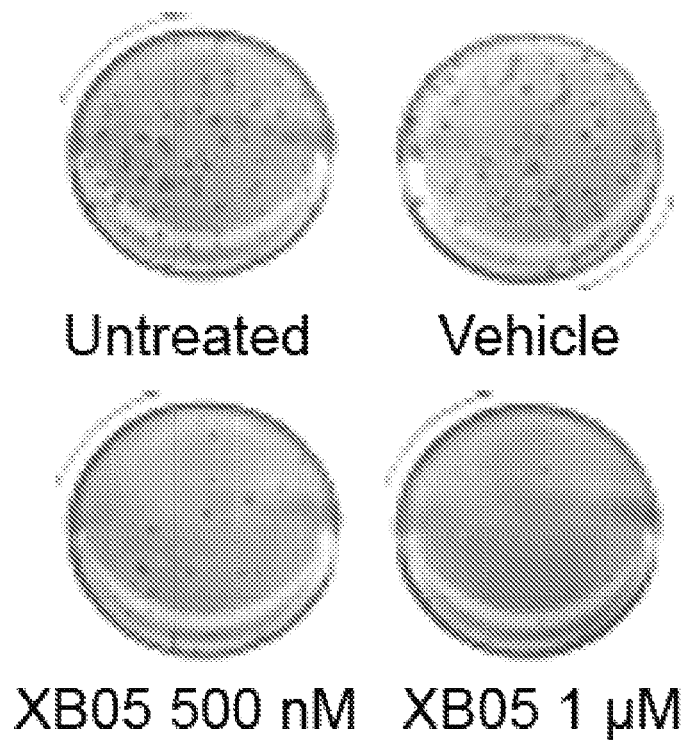
FIG. 4B are data from soft agar colony formation assays for MDA-MB-231 breast cancer cells. The cells were stained with crystal violet 21 days after plating.
Figure 4C:
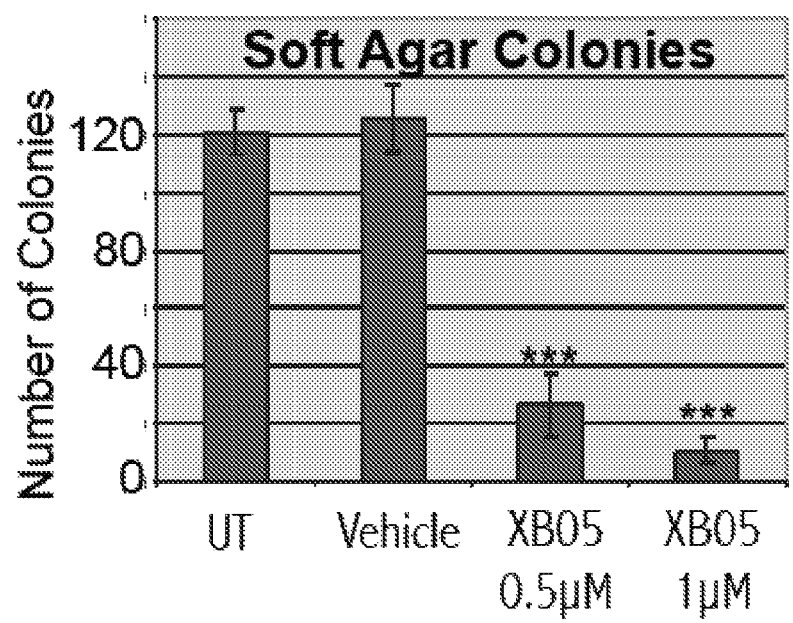
FIG. 4C is a graph of the data from the soft agar colony formation assays for MDA-MB-231 breast cancer cells. The data shown are the mean±standard error (n=3).
Figure 4D:
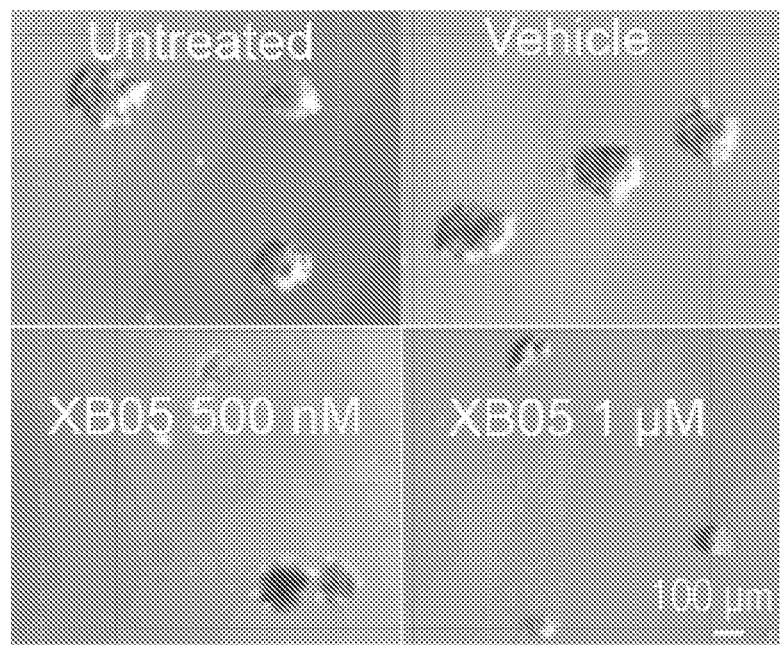
FIG. 4D are data from tumorsphere formation assays for MDA-MB-231 breast cancer cells on day 12 after plating. The data shown are representative images from three separate experiments.
Figure 4E:
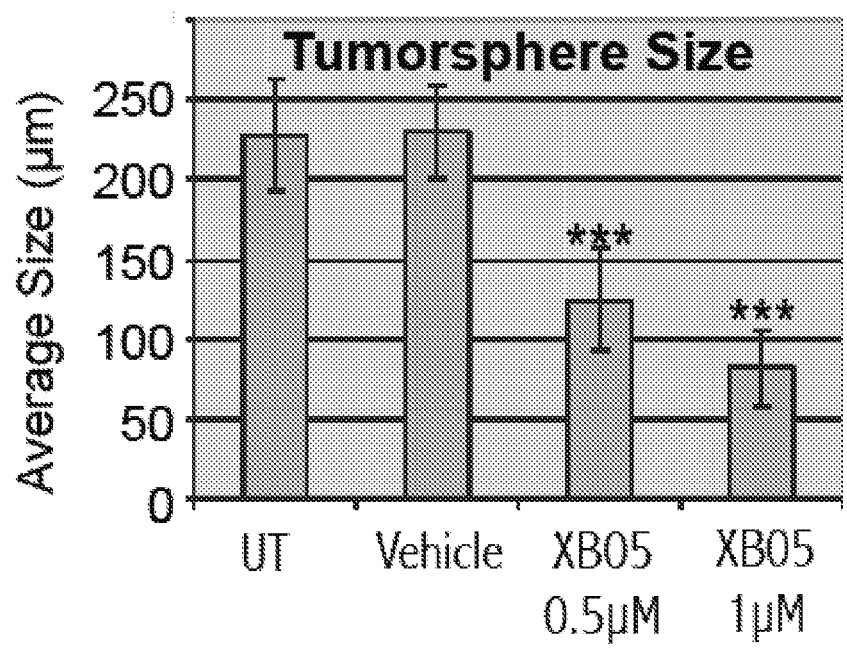
FIG. 4E is a graph of the data from the tumorsphere formation assays for MDA-MB-231 breast cancer cells on day 12 after plating.

BX11 (XB05) has potent antiproliferative and cytotoxic activity on a variety of breast cancer cell types, with some cell types having $GI_{50}$ values less than or equal to 10 μM. There were several cell lines that seemed particularly sensitive to the cytotoxic effects of BX11 (BX05). For example, in the breast cancer panel, only MDA-MB-231 and MDA-MB-435 exhibited significant cell death following treatment with 1 μM BX11 (FIG. 4A). The MDA-MB-231 cell line is derived from a triple negative breast cancer (TNBC) and MDA-MB-435 was originally described as being derived from a TNBC, although its origin is now uncertain (it is unquestionably derived from the same source as the M14 melanoma cell line and many believe it is a melanoma, although some argue that both cell lines are derived from a breast carcinoma). Additional experiments have confirmed the inhibitory effects of BX11 (BX05) on MDA-MB-251 breast cancer cells in standard soft agar assays (an in vitro measure of tumorigenicity) and tumorsphere assays, where cells are grown in three-dimensional, non-adherent cultures. This latter assay is often used to assess activity against the subpopulation of stem-like cancer cells with enhanced tumor-initiating capacity. The data from these experiments show that BX11 (XB05) can inhibit both colony formation in soft agar and tumorsphere growth by MDA-MB-231 breast cancer cells (FIGS. 4B-4E).

Example 4

Inhibiting Effects on DMNT1 Activity

Figure 5A:
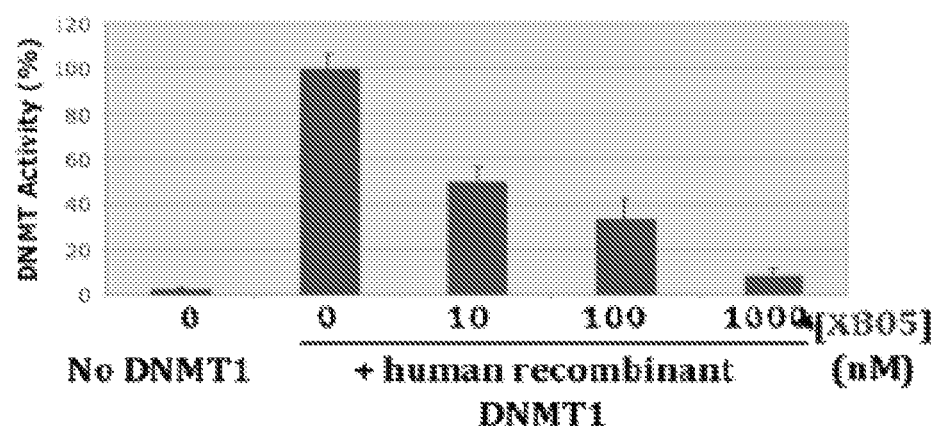
FIGS. 5A and 5B show the inhibitory effects of XB05 (BX11) on DNMT1 activity using recombinant human DNMT1 (4a) or nuclear extracts from cells treated with XB05 (BX11) or 5-Aza (4b).
Figure 5B:
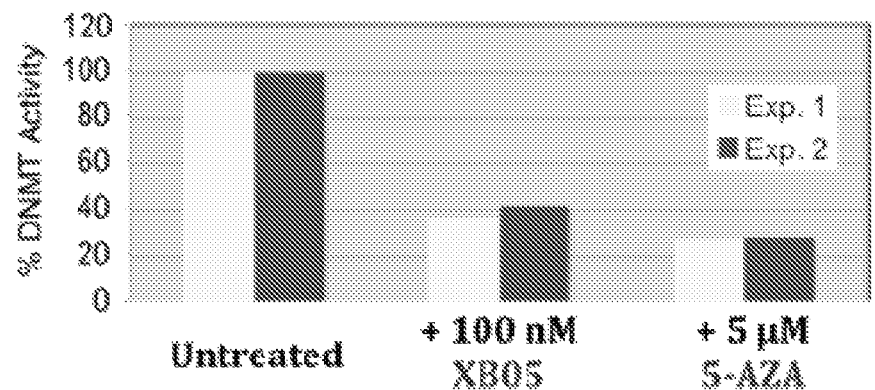

FIGS. 5A and 5B are graphs which show the inhibitory effects of XB05 (BX11) on DNMT1 activity. The assays use recombinant Human DNMT1 (FIG. 5A) or nuclear extracts prepared from cells treated with XB05 (BX11) or XB05a (BX12) (FIG. 5B).

Example 5

Figures 6A, 6B, 6C:
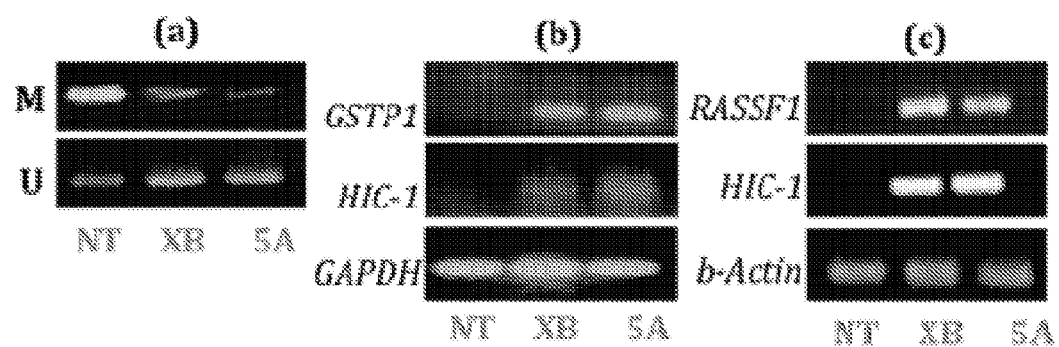
FIG. 6A-6C depict the results of experiments which show that XB05 (BX11) inhibits promoter methylation and reactivates silenced tumor suppressor genes: (a) methylation specific PCR of GST

XB05 (BX11) Inhibits Promoter Methylation and Reactivates Tumor Suppressor Genes in Prostate Cancer Cells FIG. 6A shows methylation specific PCR of GSTP1 promoter from LNCaP cells treated with 100 nm XB05 (BX11) (×5), 5 μm 5-Aza (5A), or a non-treated control (NT). FIG. 6B shows the results obtained from RT-PCR used to detect mRNA expression in DU145 prostate cancer cells. FIG. 6C shows the results obtained from similar RT-PCR assays for LNCaP cells.

Example 6

In Vivo Effects of XB05a (BX12)

Figure 7A:
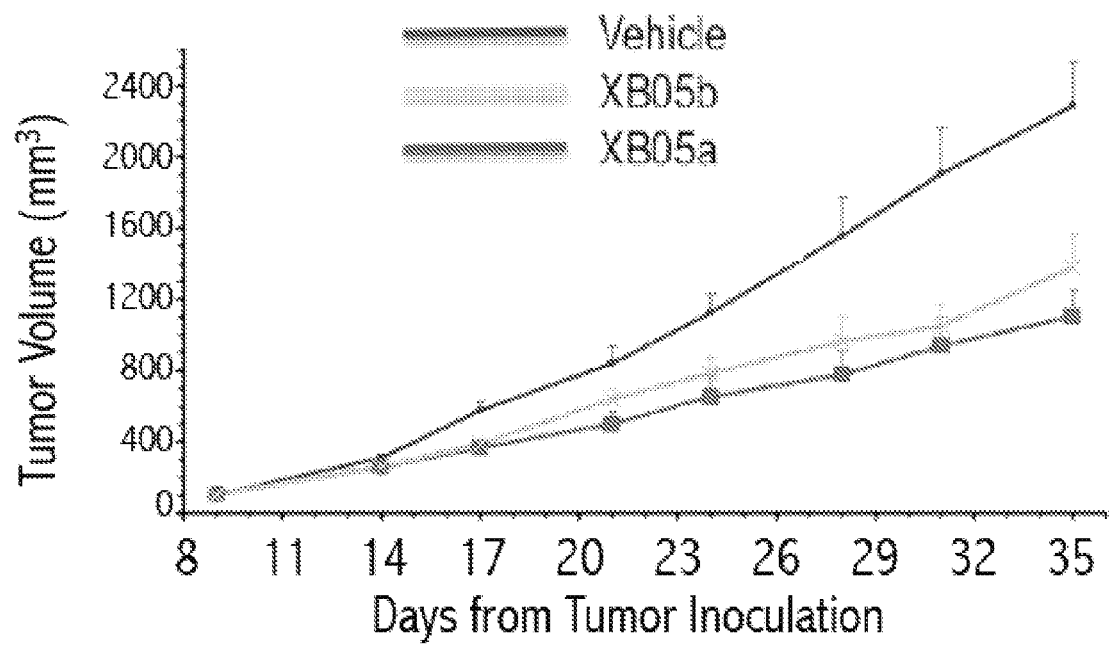
FIG. 7A-7B show the in vivo antitumor effect of XB05a (BX12): (a) nude mice bearing Colo-205 xenografts or (b) similar experiments in mice bearing A549 xenografts with XB05a (BX12) compared to 5-Aza and cisplatin (cis-pt) or with cis-pt.
Figure 7B:
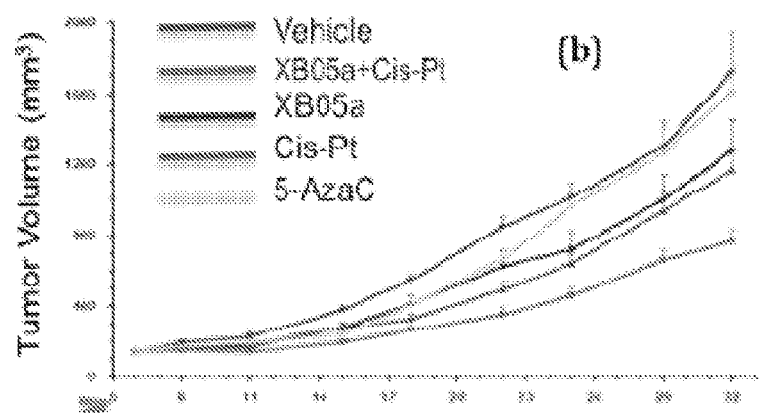
Figure 7C:
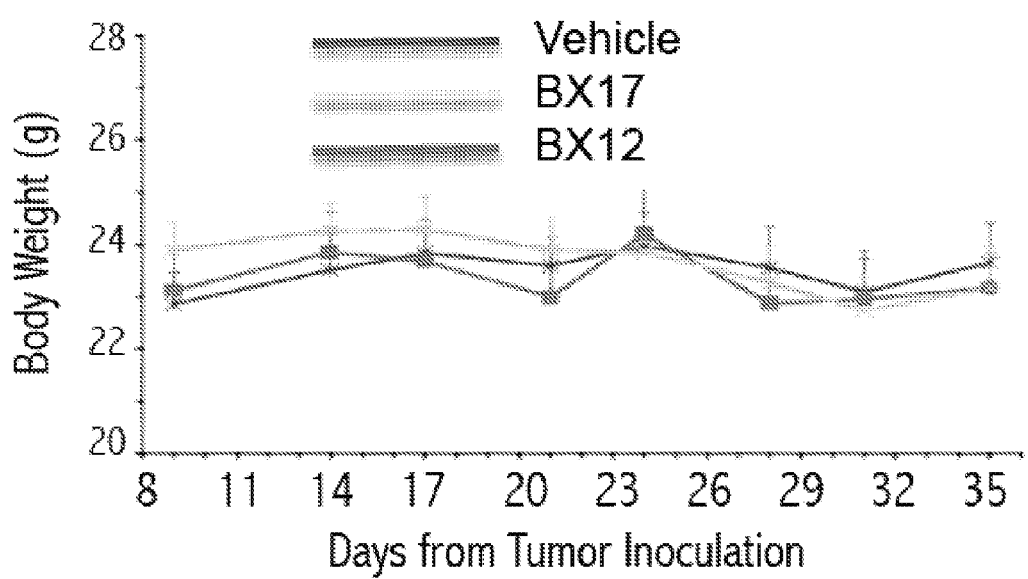
FIG. 7C is a graph of the weight of mice bearing subcutaneous colon cancer xenografts (Colo-205) that were treated with vehicle or 25 mg/kg of BX12 (XB05a) or BX17 (XB05b) daily for 21 days by intravenous injection (except the last four doses of BX12 (XB05a) which were given intraperitoneally due to tail vein sensitivity).
Figures 8A, 8B, 8C, 8D:
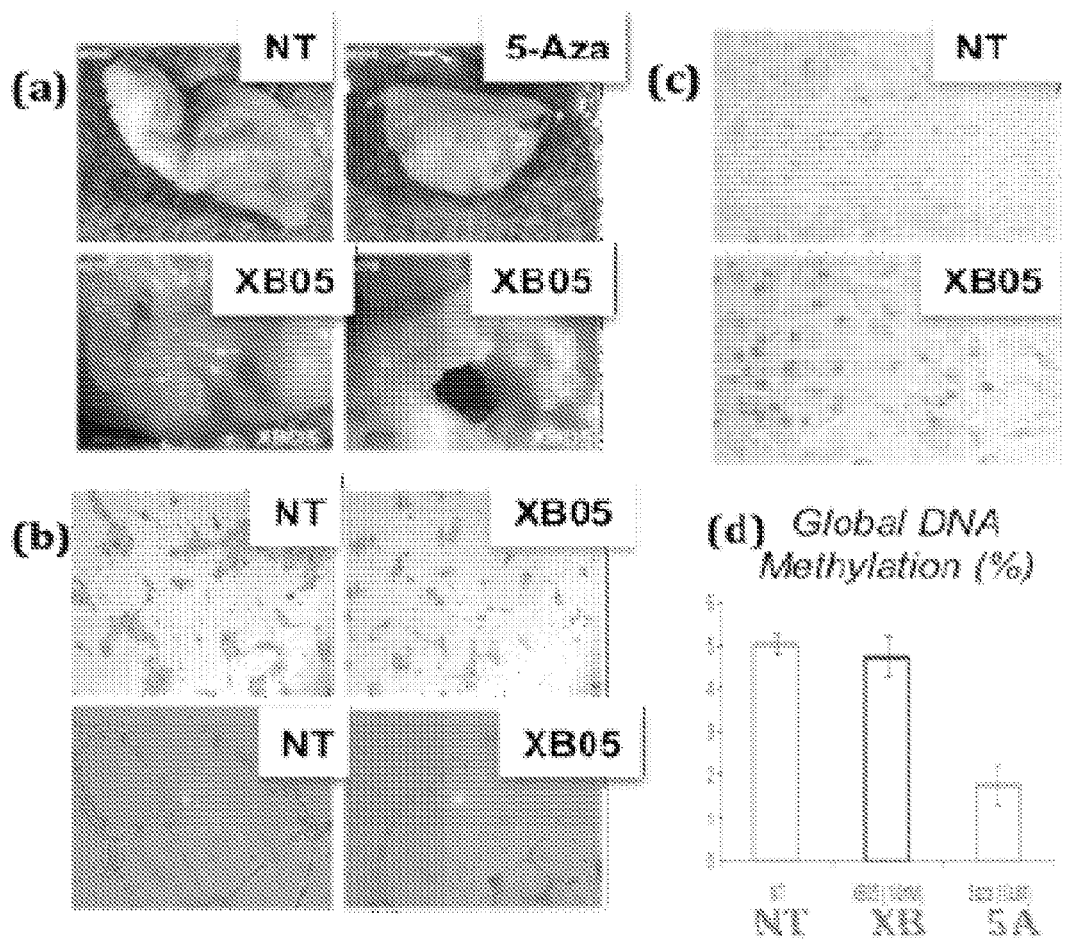
FIG. 8A-8D show unusual properties of XB05 (BX11) that are different from 5-Azacytidine; (a) XB05 (BX11) causes central tumor necrosis leading to "hollow" tumors (HCT116 xenografts); (b) inhibition of endothelial cell (HUVEC) function at 800 nM XB05 (BX11) (non-toxic to HUVECs), as shown by transwell migration (top) and tube formation assay; (c) induction of senescence in HCT116 cells after 96 h with 100 nM XB05 (BX11); (d) no effect of XB05 (BX11) on global DNA methylation suggesting its specificity for aberrantly silenced DNA.

FIGS. 7A-7B show the in vivo antitumor effect of XB05a (BX12) in (a) nude mice bearing Colo-205 xenografts treated with 25 mg/kg/day i.v. with XB05a (BX12) or 2 (analog) for 21 days; and (b) similar experiments in mice bearing A549 xenografts treated with XB05a (BX12), as compared to 5-Aza and cisplatin (cis-pt) or cis-pt alone. FIG. 7C shows the weight of nude mice bearing a Colo-205 xenograft following treatment with a vehicle or 25 mg/kg of XB05a (BX12) or XB05b (BX17) daily for 21 days by i.v. injection.

The data show that XB05a (BX12) and XB05b (BX17) have in vivo antitumor efficacy (FIGS. 7A and 7B) with no evidence of any severe non-specific toxicities, as judged by the body weight of the treated mice (FIG. 7C).

Example 7

Unusual Properties of XB05 (BX11) that are Different from 5-azacytidine

FIGS. 8A-8D show properties of XB05a (BX12) that are different from 5-azacytidine: XB05 (BX11) causes central tumor necrosis leading to "hollow" tumors (HCT116 xenografts); inhibition of endothelial cell (HUVEC) function at 800 nM XB05 (BX11) (non-toxic to HUVECs), as shown by transwell migration and tube formation assay; induction of senescence in HCT116 cells after 96 h with 100 nM XB05 (BX11); and no effect of XB05 (BX11) on global DNA methylation suggesting its specificity for aberrantly silenced DNA.

Example 8

BX11 (XB05) Inhibits DNMT1 Activity

Figure 9A:
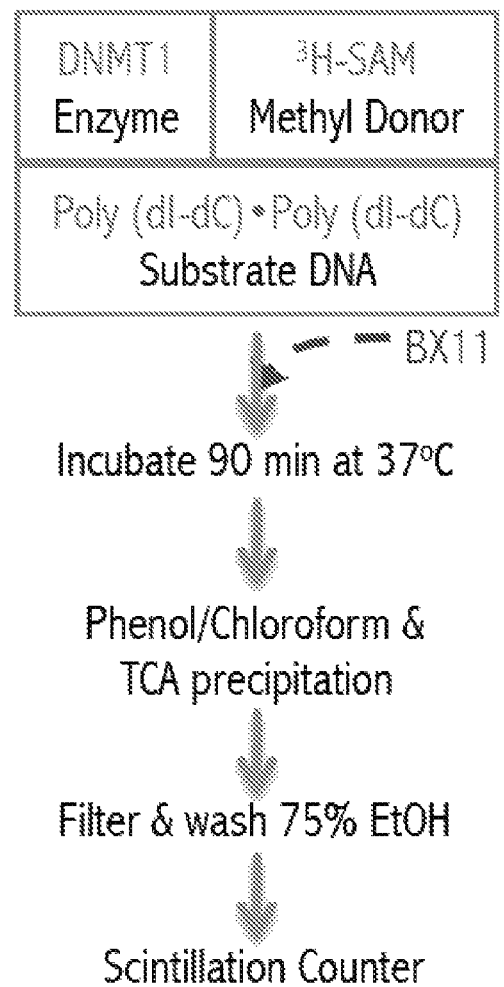
FIG. 9A is a schematic of an exemplary in vitro DNMT activity assay.

Experiments described above were performed to test the effect of BX11 (XB05) on DNMT1 activity. A schematic diagram of these experiments is shown in FIG. 9A. The expression of a number of methylated (repressed) genes in MDA-MB-231 breast cancer cells was further determined using both RT-PCR and Western blotting following treatment with vehicle (control), 1 µM BX11 (XB05), or 10 µM 5-azacytidine (positive control).

Figure 9B:
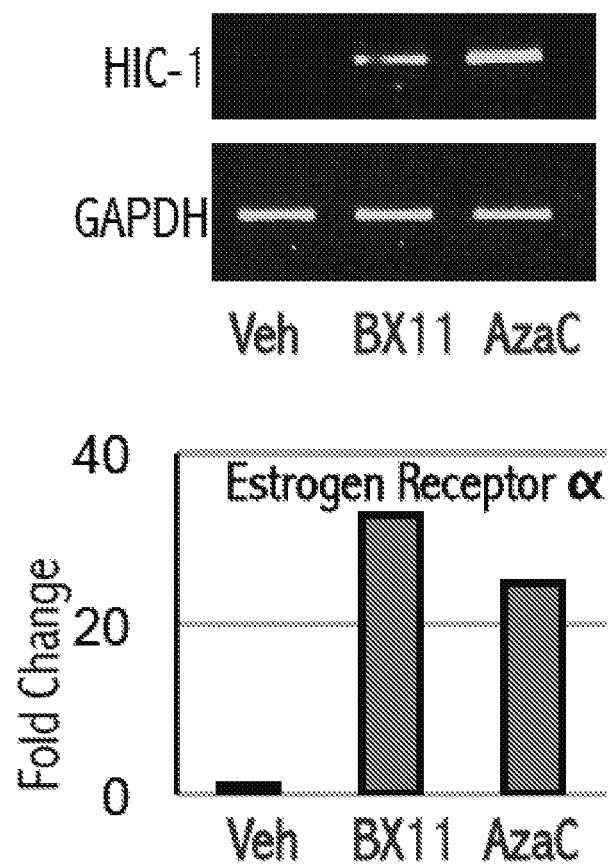
FIG. 9B is RT-PCRT data (top), quantitative RT-PCR data (middle), and Western blot data (bottom) from MDA-MB-231 breast cancer cells that show that genes commonly silenced by methylation in MDA-MB-231 cells are re-expressed after treatment with XB05 (BX11), but the expression of control genes (GAPDH and β-actin) are unchanged.
Figure 9B:
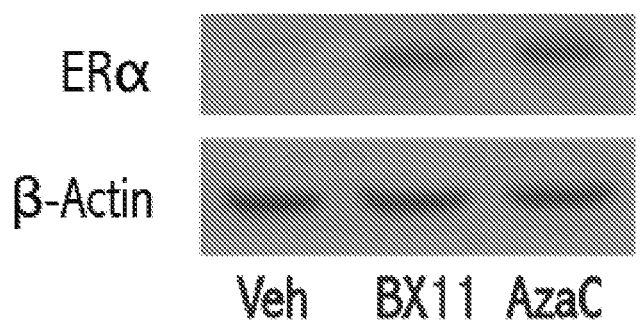

The resulting data show that treatment of breast cancer cells with BX11 (XB05) for 72 hours leads to specific reactivation of genes that are commonly silenced by hypermethylation in breast cancer cells (FIG. 9B).

Example 9

Prostate Cancer Cell dU145 and PC-3 prostate cancer cell lines are used as models for metastatic castration-resistant prostate cancers, and RWPE-1 cells are used as a model for non-malignant prostate cells. Although using cell lines has certain limitations, they can be manipulated to quickly test hypotheses, which can then be confirmed in animal models and in humans. DU145 and PC-3 cells are derived from metastatic prostate cancer lesions (to brain and bone, respectively); they are androgen-insensitive and highly tumorgenic in immunocompromised mice. RWPE-1 cells are derived from normal human prostate epithelial cells transfected with HPV18 DNA to immortalize them; they form normal acini, are androgen-responsive and non-tumorgenic in nude mice, inefficiently form colonies of soft agar, and maintain diploid status during culture.

XB05 (BX11) and XB05a (BX12) are synthesized using a modification of a previously described technique (see, U.S. Patent Application No. 2008/0188570; herein incorporated by reference), which allows for the easy preparation of gram quantities of material. Racemic mixtures are used because structure-activity studies indicate that R and S enantiomers are equally active, but pure enantiomers can be easily synthesized, if necessary, from the commercially available starting material. For all assays, both XB05 (BX11) and XB05a (BX12) are included.

To begin the biological assays, the prostate cell lines that are commercially available (DU145, PC-3, LNCaP, MDA-PCa-2b, RWPE-1, RWPE-2) will be surveyed to evaluate levels of SOX9 protein by Western blotting, SOX9 mRNA by qRT-PCR, and SOX9 localization by immunofluorescence. The response of these cells to XB05 (BX11) and XB05a (BX12) are assessed in terms of antiproliferative effects (MTT assay), clonogenic survival, and cell death induction.

It is expected that SOX9 levels will be increased in the cell lines representing more advanced prostate cancers compared to the non-tumorigenic cell line, RWPE-1, and a correlation will be observed between SOX9 levels and response to XB05 (BX11).

Experiments similar to those shown in FIG. 2 are performed to determine the effects of knocking down SOX9 using prostate cancer cell lines that have appreciable levels of SOX9 and response to XB05 (BX11). Several different SOX9 siRNAs are used.

Complementary experiments are performed to test the hypothesis that non-malignant RWPE-1 cells with ectopic expression of SOX9 will have increased sensitivity to XB05 (BX11) and XB05a (BX12). Transient and stable transfections with a SOX9-expressing construct are used (Wang et al., Cancer Res. 68:1625-1630, 2008; Wang et al., Cancer Res. 67:528-536, 2007). One cell line is selected to create stable transfectants that express either SOX9 cDNA or SOX9 shRNA or empty vector (as control) under the control of a tetracycline-inducible promoter. A retroviral expression system is used with standard BSL2 precautions. This is done by stably transfecting the chosen cell line to express the tetracycline-regulated transactivator using the pRetroX-Tet-On system (Clontech) followed by selection with G418. The resulting clonal cell lines is tested in transient transfection reporter assays to identify the cell lines that give the best doxycycline-induced gene expression (in terms of levels and specificity). These "Tet-On" cell lines are then retrovirally transduced with pRetroX-Tight-Pur vector containing the epitope-tagged SOX9 cDNA or SOX9 shRNA, as recently described (Wang et al., Cancer Res. 68:1625-1630, 2008). Stable clones are selected and maintained in medium containing G418+ puromycin. Gene expression is induced by addition of doxycycline and cells are evaluated for levels of SOX9 expression and induction of cell death in response to XB05 (BX11) and XB05a (BX12).

Example 10

Animal Models of Prostate Cancer

Three murine models of prostate cancer are used to evaluate XB05a (BX12) activity: (i) nude mice bearing subcutaneous DU145 xenografts, e.g., monitored by caliper measurement; (ii) C57BL/6 mice with subcutaneous TRAMP-Cl tumors, monitored by caliper measurement; and (iii) a model of prostate cancer bone metastasis using JCR SCID mice that have received intracardiac injection of luciferase-expressing PC3 cells, e.g., monitored by combined bioluminescent imaging (BLI) and microCT. The second model is used to determine the possibility that XB05 (BX11) has immunomodulatory effects and the known effects of other DNMT inhibitors (Sigalotti et al., Semin. Oncol. 32:473-478, 2005), so it is important to evaluate activity in an immunocompetent mouse model. The third model is perhaps most representative of the clinical problems associated with advanced prostate cancer, so it is important to demonstrate XB05a (BX12) efficacy in this setting.

Prior to these in vivo studies, cultured cells are used to screen for any agents that might have synergistic activity with XB05 (BX11). Due to its DNA demethylating activity, XB05a (BX12) may sensitize cells to the effects of chemotherapy or differentiating agents, so the combination activity index (Budman et al., Anticancer Drugs 17:921-928, 2006) of XB05a (BX12) co-administered with agents, such as HDAC inhibitors, docetaxel, cisplatin, doxorubicin, camptothecin, 5-fluorouracil, anti-androgen, and ATRA, is determined Based on the results, one agent for in vivo testing in combination with XB05a (BX12) is selected. For testing combination of agents, there are four groups of mice (vehicle, XB05a (BX12) alone, other agent alone, XB05a (BX12)+other agent) with typically 10 mice per group.

For subcutaneous tumor formation, 5-8 week old male mice are administered $5 \times 10^6$ cancer cells in 100 µl medium by injection into their rear flanks. When tumors have reached approximately 400 mm$^3$, mice are randomized into groups and receive daily i.v. injections of XB05a (BX12) (25 mg/kg/day) and/or the other agent (doses selected based on the cell-based studies and literature reports) for 21 days. Tumor volume and body weight are monitored throughout. Mice are euthanized when tumor volume reaches approximately 1500 mm$^3$ or before that, if they show any signs of distress. Data are expressed as the mean±SEM and compared using student's t-test and ANOVA analyses. Results are considered statistically significant ifp values are <0.05. For the metastatic model, ICR SCID anaesthetized mice receive intracardiac injection of $1 \times 10^6$ PC-3-luc cells (Caliper Biosciences) in a solution containing blue dye for visual verification. Weekly BLI imaging (following i.p. injection of luciferin) and parallel microCT are carried out under isofluorane anesthesia and at the end of the experiment, bones and organ are harvested for visual confirmation and quantification of metastases.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the claims

What is claimed is:

1. A method for predicting efficacy of a DNA (cytosine-5)-methyltransferase 1 (DNMT1) inhibitor treatment in a subject having a cancer, the method comprising:
determining a level of SOX9 in a sample comprising cells from a subject having a cancer; and
predicting increased efficacy of a DNMT1 inhibitor treatment in a subject that has an elevated level of SOX9 in the sample compared to a reference level, or decreased efficacy of a DNMT1 inhibitor treatment in a subject that has no significant change or a decreased level of SOX9 in the sample compared to a reference level;
where the subject has a cancer selected from the group consisting of: chondrosarcoma cancer, lung cancer, malignant peripheral nerve sheath tumor, prostate cancer, malignant melanoma, a sarcoma, breast cancer, colon cancer, gastric cancer, pancreatic cancer, brain cancer, basal cell carcinoma, liver cancer, leukemia, and myelodysplastic syndrome, and
the DNMT1 inhibitor treatment comprises the administration of one or more DNMT1 inhibitors of Formula I

(I)

wherein:
$R_1$ is carboxy, $(C_1$-$C_{20})$alkoxycarbonyl, $(C_2$-$C_{20})$alkenyloxycarbonyl, $(C_2$-$C_{20})$alkynyloxycarbonyl, $(C_1$-$C_{20})$alkyl, $(C_2$-$C_{20})$alkenyl, or $(C_2$-$C_{20})$alkynyl, which $(C_1$-$C_{20})$alkyl, $(C_2$-$C_{20})$alkenyl, or $(C_2$-$C_{20})$alkynyl, is substituted with one or more groups independently selected from halo, hydroxy, mercapto, $(C_1$-$C_{20})$alkoxy, $(C_2$-$C_{20})$alkenyloxy, $(C_2$-$C_{20})$alkynyloxy, aryloxy, heteroaryloxy, $(C_3$-$C_{20})$cycloalkyloxy, heterocyclyloxy, $(C_1$-$C_{20})$alkylthio, $(C_2$-$C_{20})$alkenylthio, $(C_2$-$C_{20})$alkynylthio, carboxy, $(C_1$-$C_{20})$alkoxycarbonyl, $(C_2$-$C_{20})$alkenyloxycarbonyl, $(C_2$-$C_{20})$alkynyloxycarbonyl, aryl, heteroaryl, cycloalkyl, heterocyclyl, $NR_aR_b$, $(C_2$-$C_{20})$alkynoyloxy, and arylcarbonyloxy;
$R_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, $CF_2I$, $CFHI$, $C(R_c)(R_d)I$, $CF(R_e)I$, or $CCl_3$;

each $R_a$ and $R_b$ is independently H, $(C_1$-$C_{20})$alkyl, $(C_1$-$C_{20})$alkanoyl, $(C_2$-$C_{20})$alkenylcarbonyl, $(C_2$-$C_{20})$alkynylcarbonyl, $(C_1$-$C_{20})$alkoxy, $(C_2$-$C_{20})$alkenyloxy, $(C_2$-$C_{20})$alkynyloxy, or aryl-$(C_1$-$C_{20})$alkoxycarbonyl;
each $R_c$ and $R_d$ is independently H, $(C_1$-$C_{20})$alkyl, $(C_1$-$C_{20})$alkanoyl, $(C_2$-$C_{20})$alkenylcarbonyl, $(C_2$-$C_{20})$alkynylcarbonyl, $(C_1$-$C_{20})$alkoxy, $(C_2$-$C_{20})$alkenyloxy, or $(C_2$-$C_{20})$alkynyloxy; and
$R_e$ is $(C_1$-$C_{20})$alkyl, $(C_1$-$C_{20})$alkanoyl, $(C_2$-$C_{20})$alkenylcarbonyl, $(C_2$-$C_{20})$alkynylcarbonyl, $(C_1$-$C_{20})$alkoxy, $(C_2$-$C_{20})$alkenyloxy, or $(C_2$-$C_{20})$alkynyloxy;
wherein each aryl, heteroaryl, heterocyclyl, aryloxy, heteroaryloxy, arylcarbonyloxy or heteroarylcarbonyloxy of $R_1$ is optionally substituted with one or more groups independently selected from halo, hydroxy, nitro, cyano, trifluoromethyl, trifluoromethoxy, mercapto, carboxy, $(C_1$-$C_{20})$alkyl, $(C_2$-$C_{20})$alkenyl, $(C_2$-$C_{20})$alkynyl, $(C_1$-$C_{20})$alkoxy, $(C_2$-$C_{20})$alkenyloxy, $(C_2$-$C_{20})$alkynyloxy, $(C_1$-$C_{20})$alkylthio, $(C_2$-$C_{20})$alkenylthio, $(C_2$-$C_{20})$alkynylthio, $(C_1$-$C_{20})$alkoxycarbonyl, $(C_2$-$C_{20})$alkenyloxycarbonyl, $(C_2$-$C_{20})$alkynyloxycarbonyl, aryl, heteroaryl, aryl$(C_1$-$C_{20})$alkyl, heteroaryl$(C_1$-$C_{20})$alkyl, aryl$(C_2$-$C_{20})$alkenyl, aryl$(C_2$-$C_{20})$alkynyl, heteroaryl$(C_2$-$C_{20})$alkenyl, heteroaryl$(C_2$-$C_{20})$alkynyl, $(C_1$-$C_{20})$alkanoyloxy, $(C_2$-$C_{20})$alkenoyloxy, $(C_2$-$C_{20})$alkynoyloxy; or a salt thereof.

2. The method of claim 1, wherein the reference level is a level of SOX9 in a sample comprising cells from a healthy subject.

3. The method of claim 1, wherein the sample comprising cells is a cancer biopsy sample.

4. The method of claim 1, wherein the level of SOX9 in the sample is a level of SOX9 protein in the sample.

5. The method of claim 1, wherein the level of SOX9 in the sample is a level of SOX9 mRNA in the sample.

6. The method of claim 1, wherein the subject has a cancer selected from the group consisting of: chondrosarcoma cancer, lung cancer, malignant peripheral nerve sheath tumor, prostate cancer, malignant melanoma, a sarcoma, breast cancer, colon cancer, gastric cancer, pancreatic cancer, brain cancer, liver cancer, leukemia, and myelodysplastic syndrome.

7. The method of claim 1, further comprising selecting a subject having a cancer.

8. The method of claim 1, wherein the DNMT1 inhibitor treatment comprises the administration of one or more DNMT1 inhibitors of Formula I

wherein:
R$_1$ is (C$_1$-C$_{20}$)alkoxycarbonyl, (C$_2$-C$_{20}$)alkenyloxycarbonyl, (C$_2$-C$_{20}$)alkynyloxycarbonyl, (C$_1$-C$_{20}$)alkyl, (C$_2$-C$_{20}$)alkenyl, or (C$_2$-C$_{20}$)alkynyl, which (C$_1$-C$_{20}$)alkyl, (C$_2$-C$_{20}$)alkenyl, or (C$_2$-C$_{20}$)alkynyl, is substituted with one or more groups independently selected from halo, hydroxy, mercapto, (C$_1$-C$_{20}$)alkoxy, (C$_2$-C$_{20}$)alkenyloxy, (C$_2$-C$_{20}$)alkynyloxy, aryloxy, heteroaryloxy, (C$_3$-C$_{20}$)cycloalkyloxy, heterocyclyloxy, (C$_1$-C$_{20}$)alkylthio, (C$_2$-C$_{20}$)alkenylthio, (C$_2$-C$_{20}$)alkynylthio, carboxy, (C$_1$-C$_{20}$)alkoxycarbonyl, (C$_2$-C$_{20}$)alkenyloxycarbonyl, (C$_2$-C$_{20}$)alkynyloxycarbonyl, aryl, heteroaryl, cycloalkyl, heterocyclyl, NR$_a$R$_b$, (C$_2$-C$_{20}$)alkynoyloxy, and arylcarbonyloxy;

R$_2$ is CF$_2$Br, CFHBr, CF$_2$C$_1$, CFHC$_1$, CFBr$_2$, CFCl$_2$, CBr$_3$, C(R$_c$)(R$_d$)Br, C(Rc)(R$_d$)Cl, CF(R$_e$)Br, CF$_2$I, CFHI, C(R$_c$)(R$_d$)I, CF(R$_e$)I, or CCl$_3$;

each R$_a$ and R$_b$ is independently H, (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$)alkoxy, (C$_2$-C$_{20}$)alkenyloxy, (C$_2$-C$_{20}$)alkynyloxy, or aryl-(C$_1$-C$_{20}$)alkoxycarbonyl;

each R$_c$ and R$_d$ is independently H, (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$)alkoxy, (C$_2$-C$_{20}$)alkenyloxy, or (C$_2$-C$_{20}$)alkynyloxy; and R$_e$ is (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$)alkoxy, (C$_2$-C$_{20}$)alkenyloxy, or (C$_2$-C$_{20}$)alkynyloxy;

wherein each aryl, heteroaryl, heterocyclyl, aryloxy, heteroaryloxy, arylcarbonyloxy or heteroarylcarbonyloxy of R$_1$ is optionally substituted with one or more groups independently selected from halo, hydroxy, nitro, cyano, trifluoromethyl, trifluoromethoxy, mercapto, carboxy, (C$_1$-C$_{20}$)alkyl, (C$_2$-C$_{20}$)alkenyl, (C$_2$-C$_{20}$)alkynyl, (C$_1$-C$_{20}$)alkoxy, (C$_2$-C$_{20}$)alkenyloxy, (C$_2$-C$_{20}$)alkynyloxy, (C$_1$-C$_{20}$)alkylthio, (C$_2$-C$_{20}$)alkenylthio, (C$_2$-C$_{20}$)alkynylthio, (C$_1$-C$_{20}$)alkoxycarbonyl, (C$_2$-C$_{20}$)alkenyloxycarbonyl, (C$_2$-C$_{20}$)alkynyloxycarbonyl, aryl, heteroaryl, aryl(C$_1$-C$_{20}$)alkyl, heteroaryl(C$_1$-C$_{20}$)alkyl, aryl(C$_2$-C$_{20}$)alkenyl, aryl(C$_2$-C$_{20}$)alkynyl, heteroaryl(C$_2$-C$_{20}$)alkenyl, heteroaryl(C$_2$-C$_{20}$)alkynyl, (C$_1$-C$_{20}$)alkanoyloxy, (C$_2$-C$_{20}$)alkenoyloxy, (C$_2$-C$_{20}$)alkynoyloxy; or a salt thereof.

9. The method of claim 1, wherein the DNMT1 inhibitor treatment comprises the administration of

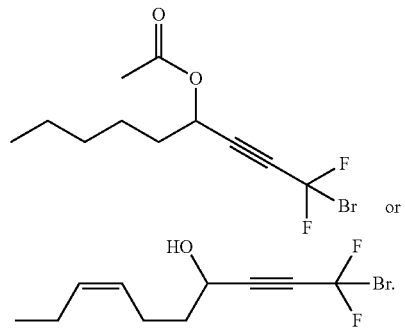

10. The method of claim 1, wherein the subject has a cancer selected from the group consisting of: lung cancer, breast cancer, colon cancer, and prostate cancer.

11. The method of claim 1, wherein
R$_1$ is (C$_1$-C$_{20}$)alkoxycarbonyl, (C$_2$-C$_{20}$)alkenyloxycarbonyl, (C$_1$-C$_{20}$)alkyl, or (C$_2$-C$_{20}$)alkenyl, which (C$_1$-C$_{20}$)alkyl or (C$_2$-C$_{20}$)alkenyl, is substituted with one or more groups independently selected from halo, hydroxy, mercapto, (C$_1$-C$_{20}$)alkoxy, (C$_2$-C$_{20}$)alkenyloxy, (C$_2$-C$_{20}$)alkynyloxy, aryloxy, heteroaryloxy, (C$_3$-C$_{20}$)cycloalkyloxy, heterocyclyloxy, (C$_1$-C$_{20}$)alkylthio, (C$_2$-C$_{20}$)alkenylthio, and (C$_2$-C$_{20}$)alkynylthio, carboxy; and
R$_2$ is CF$_2$Br, CFHBr, CF$_2$C$_1$, CFHC$_1$, CFBr$_2$, CFCl$_2$, CBr$_3$, CF$_2$I, CFHI, or CCl$_3$.

12. The method of claim 1, wherein
R$_1$ is (C$_1$-C$_{20}$)alkyl or (C$_2$-C$_{20}$)alkenyl, which (C$_1$-C$_{20}$)alkyl or (C$_2$-C$_{20}$)alkenyl, is substituted with one or more groups independently selected from hydroxy, (C$_1$-C$_{20}$)alkoxy, (C$_2$-C$_{20}$)alkenyloxy, (C$_2$-C$_{20}$)alkynyloxy, and carboxy; and
R$_2$ is CF$_2$Br, CF$_2$C$_1$, or CF$_2$I.

13. The method of claim 1, wherein the subject has a cancer selected from the group consisting of: lung cancer, breast cancer, colon cancer, and prostate cancer;
R$_1$ is (C$_1$-C$_{20}$)alkyl or (C$_2$-C$_{20}$)alkenyl, which (C$_1$-C$_{20}$)alkyl or (C$_2$-C$_{20}$)alkenyl, is substituted with one or more groups independently selected from hydroxy, (C$_1$-C$_{20}$)alkoxy, (C$_2$-C$_{20}$)alkenyloxy, (C$_2$-C$_{20}$)alkynyloxy, and carboxy; and
R$_2$ is CF$_2$Br, CF$_2$C$_1$, or CF$_2$I.

14. The method of claim 1, wherein the determining a level of SOX9 comprises using an immunohistochemical assay, a Western Blot, a quantitative real-time polymerase chain reaction, or a combination thereof.

* * * * *

SEQUENCE LISTING

```
<160> NUMBER OF SEQ ID NOS: 8

<210> SEQ ID NO 1
<211> LENGTH: 2605
<212> TYPE: DNA
<213> ORGANISM: Homo sapiens

<400> SEQUENCE: 1
atcgtcgacc cacgcgtccg aagcggagct cgaaactgac tggaaacttc agtggcgcgg      60
agactcgcca gtttcaaccc cggaaacttt tctttgcagg aggagaagag aagggtgca     120 agcgccccca cttttgctct ttttcctccc ctcctcctcc tctccaattc gcctcccccc     180
acttggagcg ggcagctgtg aactggccac cccgcgcctt cctaagtgct cgccgcggta     240
gccggccgac gcgccagctt ccccgggagc cgcttgctcc gcatccgggc agccgagggg     300
agaggagccc gcgcctcgag tccccgagcc gccgcggctt ctcgcctttc ccggccacca     360
gccccctgcc ccgggcccgc gtatgaatct cctggacccc ttcatgaaga tgaccgacga     420
gcaggagaag ggcctgtccg gcgcccccag ccccaccatg tccgaggact ccgcgggctc     480
gccctgcccg tcgggctccg gctcggacac cgagaacacg cggcccagg agaacacgtt     540 ccccaagggc gagcccgatc tgaagaagga gagcgaggag gacaagttcc ccgtgtgcat     600
ccgcgaggcg gtcagccagg tgctcaaagg ctacgactgg acgctggtgc ccatgccggt     660
gcgcgtcaac ggctccagca agaacaagcc gcacgtcaag cggcccatga acgccttcat     720
ggtgtgggcg caggcggcgc gcaggaagct cgcggaccag tacccgcact tgcacaacgc     780
```

| | | |
|---|---|---|
| cgagctcagc aagacgctgg gcaagctctg gagacttctg aacgagagcg agaagcggcc | 840 | |
| cttcgtggag gaggcggagc ggctgcgcgt gcagcacaag aaggaccacc cggattacaa | 900 | |
| gtaccagccg cggcggagga agtcggtgaa gaacgggcag gcggaggcag aggaggccac | 960 | |
| ggagcagacg cacatctccc ccaacgccat cttcaaggcg ctgcaggccg actcgccaca | 1020 | |
| ctcctcctcc ggcatgagcg aggtgcactc ccccggcgag cactcggggc aatcccaggg | 1080 | |
| cccaccgacc ccacccacca cccccaaaac cgacgtgcag ccgggcaagg ctgacctgaa | 1140 | |
| gcgagagggg cgccccttgc cagagggggg cagacagccc cctatcgact tccgcgacgt | 1200 | |
| ggacatcggc gagctgagca gcgacgtcat ctccaacatc gagaccttcg atgtcaacga | 1260 | |
| gtttgaccag tacctgccgc ccaacggcca cccgggggtg ccggccacgc acggccaggt | 1320 | |
| cacctacacg ggcagctacg gcatcagcag caccgcggcc accccggcga gcgcgggcca | 1380 | |
| cgtgtggatg tccaagcagc aggcgccgcc gccaccccg cagcagcccc cacaggcccc | 1440 | |
| gccggccccg caggcgcccc cgcagccgca ggcggcgccc ccacagcagc cggcggcacc | 1500 | |
| cccgcagcag ccacaggcgc acacgctgac cacgctgagc agcgagccgg ccagtccca | 1560 | |
| gcgaacgcac atcaagacgg agcagctgag ccccagccac tacagcgagc agcagcagca | 1620 | |
| ctcgccccaa cagatcgcct acagccccctt caacctccca cactacagcc ctcctaccc | 1680 | |
| gcccatcacc cgctcacagt acgactacac cgaccaccag aactccagct cctactacag | 1740 | |
| ccacgcggca ggccagggca ccggcctcta ctccaccttc acctacatga accccgctca | 1800 | |
| gcgccccatg tacacccca tcgccgacac ctctggggtc ccttccatcc cgcagaccca | 1860 | |
| cagccccccag cactgggaac aacccgtcta cacacagctc actcgaccctt gaggaggcct | 1920 | |
| cccacgaagg gcgaagatgg ccgagatgat cctaaaaata accgaagaaa gagaggacca | 1980 | |
| accagaattc cctttggaca tttgtgtttt tttgttttt tattttgttt tgttttttct | 2040 | |
| tcttcttctt cttccttaaa gacatttaag ctaaaggcaa ctcgtaccca aatttccaag | 2100 | |
| acacaaacat gacctatcca agcgcattac ccacttgtgg ccaatcagtg gccaggccaa | 2160 | |
| ccttggctaa atggagcagc gaaatcaacg agaaactgga ctttttaaac cctcttcaga | 2220 | |
| gcaagcgtgg aggatgatgg agaatcgtgt gatcagtgtg ctaaatctct ctgcctgttt | 2280 | |
| ggactttgta attatttttt tagcagtaat taaagaaaaa agtcctctgt gaggaatatt | 2340 | |
| ctctatttta aatattttta gtatgtactg tgtatgattc attaccattt tgaggggatt | 2400 | |
| tatacatatt tttagataaa attaaatgct cttatttttc caacagctaa actactctta | 2460 | |
| gttgaacagt gtgccctagc ttttcttgca accagagtat ttttgtacag atttgctttc | 2520 | |
| tcttacaaaa aaaaaaaaaa aaaaaaaaaa aaaaaaaaaa aaaaaaaaaa aaaaaaaaaa | 2580 | |
| aaaaaaaaaa aaaaaaaaaa aaaaa | 2605 | |

<210> SEQ ID NO 2
<211> LENGTH: 509
<212> TYPE: PRT
<213> ORGANISM: Homo sapiens

<400> SEQUENCE: 2

Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
                20                  25                  30

Ser Pro Cys Pro Ser Gly Ser Gly Ser Asp Thr Glu Asn Thr Arg Pro
            35                  40                  45

```
Gln Glu Asn Thr Phe Pro Lys Gly Glu Pro Asp Leu Lys Lys Glu Ser
     50                  55                  60

Glu Glu Asp Lys Phe Pro Val Cys Ile Arg Glu Ala Val Ser Gln Val
 65                  70                  75                  80

Leu Lys Gly Tyr Asp Trp Thr Leu Val Pro Met Pro Val Arg Val Asn
                 85                  90                  95

Gly Ser Ser Lys Asn Lys Pro His Val Lys Arg Pro Met Asn Ala Phe
                100                 105                 110

Met Val Trp Ala Gln Ala Ala Arg Arg Lys Leu Ala Asp Gln Tyr Pro
            115                 120                 125

His Leu His Asn Ala Glu Leu Ser Lys Thr Leu Gly Lys Leu Trp Arg
        130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
            180                 185                 190

Thr Glu Gln Thr His Ile Ser Pro Asn Ala Ile Phe Lys Ala Leu Gln
        195                 200                 205

Ala Asp Ser Pro His Ser Ser Gly Met Ser Glu Val His Ser Pro
210                 215                 220

Gly Glu His Ser Gly Gln Ser Gln Gly Pro Pro Thr Pro Pro Thr Thr
225                 230                 235                 240

Pro Lys Thr Asp Val Gln Pro Gly Lys Ala Asp Leu Lys Arg Glu Gly
                245                 250                 255

Arg Pro Leu Pro Glu Gly Gly Arg Gln Pro Pro Ile Asp Phe Arg Asp
            260                 265                 270

Val Asp Ile Gly Glu Leu Ser Ser Asp Val Ile Ser Asn Ile Glu Thr
        275                 280                 285

Phe Asp Val Asn Glu Phe Asp Gln Tyr Leu Pro Pro Asn Gly His Pro
290                 295                 300

Gly Val Pro Ala Thr His Gly Gln Val Thr Tyr Thr Gly Ser Tyr Gly
305                 310                 315                 320

Ile Ser Ser Thr Ala Ala Thr Pro Ala Ser Ala Gly His Val Trp Met
                325                 330                 335

Ser Lys Gln Gln Ala Pro Pro Pro Pro Gln Pro Pro Gln Ala
            340                 345                 350

Pro Pro Ala Pro Gln Ala Pro Pro Gln Pro Gln Ala Ala Pro Pro Gln
            355                 360                 365

Gln Pro Ala Ala Pro Gln Gln Pro Gln Ala His Thr Leu Thr Thr
        370                 375                 380

Leu Ser Ser Glu Pro Gly Gln Ser Gln Arg Thr His Ile Lys Thr Glu
385                 390                 395                 400

Gln Leu Ser Pro Ser His Tyr Ser Glu Gln Gln His Ser Pro Gln
                405                 410                 415

Gln Ile Ala Tyr Ser Pro Phe Asn Leu Pro His Tyr Ser Pro Ser Tyr
            420                 425                 430

Pro Pro Ile Thr Arg Ser Gln Tyr Asp Tyr Thr Asp His Gln Asn Ser
        435                 440                 445

Ser Ser Tyr Tyr Ser His Ala Ala Gly Gln Gly Thr Gly Leu Tyr Ser
450                 455                 460

Thr Phe Thr Tyr Met Asn Pro Ala Gln Arg Pro Met Tyr Thr Pro Ile
```

```
                465                 470                 475                 480
Ala Asp Thr Ser Gly Val Pro Ser Ile Pro Gln Thr His Ser Pro Gln
                        485                 490                 495

His Trp Glu Gln Pro Val Tyr Thr Gln Leu Thr Arg Pro
                500                 505
```

<210> SEQ ID NO 3
<211> LENGTH: 1530
<212> TYPE: DNA
<213> ORGANISM: Pan troglodytes

<400> SEQUENCE: 3

| | | | | | |
|---|---|---|---|---|---|
| atgaatctcc | tggaccccctt | catgaagatg | accgacgagc | aggagaaggg | cctgtccggc | 60 |
| gcccccagcc | ccaccatgtc | cgaggactcc | gcgggctcgc | cctgcccgtc | gggctccggc | 120 |
| tcggacaccg | agaacacgcg | gccccaggag | aacacgttcc | caagggcga | gcccgacctg | 180 |
| aagaaggaga | gcgaggagga | caagttcccc | gtgtgcatcc | gcgaggcggt | cagccaggtg | 240 |
| ctcaaaggct | acgactggac | gctggtgccc | atgccggtgc | gcgtcaacgg | ctccagcaag | 300 |
| aacaagccgc | acgtcaagcg | gcccatgaac | gccttcatgg | tgtgggcgca | ggcggcgcgc | 360 |
| aggaagctcg | ggaccagta | cccgcacttg | cacaacgccg | agctcagcaa | gacgctgggc | 420 |
| aagctctgga | gacttctgaa | cgagagcgag | aagcggcccct | tcgtggagga | ggcggagcgg | 480 |
| ctgcgcgtgc | agcacaagaa | ggaccacccg | gattacaagt | accagccgcg | gcggaggaag | 540 |
| tcggtgaaga | cgggcaggc | ggaggcagag | gaggccacgg | agcagacgca | catctccccc | 600 |
| aacgccatct | tcaaggcgct | gcaggccgac | tcgccacact | cctcctccgg | catgagcgag | 660 |
| gtgcactccc | ccggcgagca | ctcggggcaa | tcccagggcc | caccgacccc | acccaccacc | 720 |
| cccaaaaccg | acgtgcagcc | gggcaaggct | gacctgaagc | gagaggggcg | ccccttgcca | 780 |
| gagggggggca | gacagccccc | tatcgacttc | cgcgacgtgg | acatcggcga | gctgagcagc | 840 |
| gacgtcatct | ccaacatcga | gaccttcgat | gtcaacgagt | ttgaccagta | cctgccgccc | 900 |
| aacggccacc | cggggggtgcc | ggccacgcac | ggccaggtca | cctacacggg | cagctacggc | 960 |
| atcagcagca | ccgcggccac | cccggcgagc | gcgggccacg | tgtggatgtc | caagcagcag | 1020 |
| gcgccgccgc | cacccccgca | gcagccccca | caggccccgc | cggccccgca | ggcgccccg | 1080 |
| cagccgcagg | cggcgcccccc | acagcagccg | gcggcacccc | cgcagcagcc | acaggcgcac | 1140 |
| acgctgacca | cgctgagcag | cgagccgggc | cagtcccagc | gaacgcacat | caagacggag | 1200 |
| cagctgagcc | ccagccacta | cagcgagcag | cagcagcact | cgccccaaca | gatcgcctac | 1260 |
| agccccttca | acctcccaca | ctacagcccc | tcctacccgc | ccatcacccg | ctcacagtac | 1320 |
| gactacaccg | accaccagaa | ctccagctcc | tactacagcc | acgcggcagg | ccagggcacc | 1380 |
| ggcctctact | ccaccttcac | ctacatgaac | cccgctcagc | gccccatgta | caccccccatc | 1440 |
| gccgacacct | ctggggtccc | ttccatcccg | cagacccaca | gccccagca | ctgggaacaa | 1500 |
| cccgtctaca | cacagctcac | tcgaccttga | | | | 1530 |

<210> SEQ ID NO 4
<211> LENGTH: 509
<212> TYPE: PRT
<213> ORGANISM: Pan troglodytes

<400> SEQUENCE: 4

```
Met Asn Leu Leu Asp Pro Phe Met Lys Met Thr Asp Glu Gln Glu Lys
1               5                   10                  15
```

```
Gly Leu Ser Gly Ala Pro Ser Pro Thr Met Ser Glu Asp Ala Gly
             20                  25                  30

Ser Pro Cys Pro Ser Gly Ser Gly Ser Asp Thr Glu Asn Thr Arg Pro
         35                  40                  45

Gln Glu Asn Thr Phe Pro Lys Gly Glu Pro Asp Leu Lys Lys Glu Ser
     50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                 85                  90                  95

Gly Ser Ser Lys Asn Lys Pro His Val Lys Arg Pro Met Asn Ala Phe
                100                 105                 110

Met Val Trp Ala Gln Ala Ala Arg Arg Lys Leu Gly Asp Gln Tyr Pro
            115                 120                 125

His Leu His Asn Ala Glu Leu Ser Lys Thr Leu Gly Lys Leu Trp Arg
        130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
            180                 185                 190

Thr Glu Gln Thr His Ile Ser Pro Asn Ala Ile Phe Lys Ala Leu Gln
        195                 200                 205

Ala Asp Ser Pro His Ser Ser Gly Met Ser Glu Val His Ser Pro
210                 215                 220

Gly Glu His Ser Gly Gln Ser Gln Gly Pro Pro Thr Pro Pro Thr Thr
225                 230                 235                 240

Pro Lys Thr Asp Val Gln Pro Gly Lys Ala Asp Leu Lys Arg Glu Gly
                245                 250                 255

Arg Pro Leu Pro Glu Gly Gly Arg Gln Pro Pro Ile Asp Phe Arg Asp
            260                 265                 270

Val Asp Ile Gly Glu Leu Ser Ser Asp Val Ile Ser Asn Ile Glu Thr
        275                 280                 285

Phe Asp Val Asn Glu Phe Asp Gln Tyr Leu Pro Pro Asn Gly His Pro
290                 295                 300

Gly Val Pro Ala Thr His Gly Gln Val Thr Tyr Thr Gly Ser Tyr Gly
305                 310                 315                 320

Ile Ser Ser Thr Ala Ala Thr Pro Ala Ser Ala Gly His Val Trp Met
                325                 330                 335

Ser Lys Gln Gln Ala Pro Pro Pro Pro Gln Gln Pro Pro Gln Ala
            340                 345                 350

Pro Pro Ala Pro Gln Ala Pro Pro Gln Ala Ala Pro Pro Gln
        355                 360                 365

Gln Pro Ala Ala Pro Pro Gln Gln Pro Gln Ala His Thr Leu Thr Thr
        370                 375                 380

Leu Ser Ser Glu Pro Gly Gln Ser Gln Arg Thr His Ile Lys Thr Glu
385                 390                 395                 400

Gln Leu Ser Pro Ser His Tyr Ser Glu Gln Gln His Ser Pro Gln
                405                 410                 415

Gln Ile Ala Tyr Ser Pro Phe Asn Leu Pro His Tyr Ser Pro Ser Tyr
            420                 425                 430

Pro Pro Ile Thr Arg Ser Gln Tyr Asp Tyr Thr Asp His Gln Asn Ser
```

```
          435                 440                 445
Ser Ser Tyr Tyr Ser His Ala Ala Gly Gln Gly Thr Gly Leu Tyr Ser
    450                 455                 460

Thr Phe Thr Tyr Met Asn Pro Ala Gln Arg Pro Met Tyr Thr Pro Ile
465                 470                 475                 480

Ala Asp Thr Ser Gly Val Pro Ser Ile Pro Gln Thr His Ser Pro Gln
                485                 490                 495

His Trp Glu Gln Pro Val Tyr Thr Gln Leu Thr Arg Pro
            500                 505

<210> SEQ ID NO 5
<211> LENGTH: 1542
<212> TYPE: DNA
<213> ORGANISM: Canine lupus

<400> SEQUENCE: 5
atgaatctcc tggacccctt catgaagatg accgacgagc aggagaaggg cctgtccggc      60
gcccccagcc ccaccatgtc cgaggactcg gcgggctcgc cctgcccttc gggctccggc     120
tcggacaccg agaacacgcg gccccaggag aacacgttcc caagggcga gccggacctg      180 aagaaggaga gcgaggagga caagttcccc gtgtgcatcc gcgaggccgt cagccaggtg     240
ctcaagggct acgactggac gctggtgccc atgcccgtgc gcgtcaacgg ctcgagcaag     300
aacaagccgc acgtcaagcg gcccatgaac gccttcatgg tgtgggcgca ggcggcgcgc     360
aggaagctcg ccgaccagta cccgcacctg cacaacgccg agctcagcaa gacgctgggc     420
aagctctgga ggctgctgaa cgagagcgag aagcggccct cgtggagga gcggagcgg      480 ctgcgcgtgc agcacaagaa agaccacccg gattacaagt accagccgcg gcggaggaag     540
tcggtgaaga acgccaggc ggaggccgag gaggccaccg aacagacgca catttccccc      600
aacgccatct tcaagcgcct gcaggccgac tcgccgcact cctcctccgg catgaacgag     660
gtgcactccc ccggcaagca ctcggggcaa tcccagggcc gccgacgcc ccccaccacc      720 ccgaaaaccg acgtgcagcc gggcaaggct gacctgaagc gcgagggccg cccctgccc     780 gagggggccc gacagccccc catcgacttc gcgacgtgg acatcgggga gctgagcagc     840
gacgtcatct ccaacataga gaccttcgac gtcaacgaat cgaccagta cctgccgccc      900 aacgggcacc ccggggtgcc ggccacgcac ggccaggtca cctacacggg cagctacggc     960
atcagcagca ccgcggccac cccggcgggc gcgggccacg tgtggatgtc caagcagcag    1020
gcgccgccgc cgccgccgcc gcccccgcag cagtccccgc aggcgccccc gcagccccg     1080 caggcgcccc cgcaggcccc gcaggcgccc ccgcagccgc agcccgcgcc cccgcagccg    1140
caggcggcgc acacgctgac cccgctgagc agcgagccgg gccaggccca gcgaacgcac    1200
atcaagacgg agcagctgag cccagccac tacagcgagc agcagcagca ctcgccgcag    1260
cagatcgcct acagcccctt cagcctcccg cactacagcc cgtcctaccc gcccatcacc    1320
cgctcgcagt acgactacac tgaccaccag aactccggct cctactacag ccacgcggcg    1380
ggccagggct ccagcctcta ctccaccttc acctacatga ccccgcgca gaggcccatg     1440 tacaccccca tcgccgacac ctccggggtc ccctccatcc cgcagacgca cagcccccag    1500
cactgggaac agcctgtcta cacacagctc accaggcctt ga                        1542

<210> SEQ ID NO 6
<211> LENGTH: 513
<212> TYPE: PRT
<213> ORGANISM: Canine lupus
```

<400> SEQUENCE: 6

```
Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Asp Thr Glu Asn Thr Arg Pro
        35                  40                  45

Gln Glu Asn Thr Phe Pro Lys Gly Glu Pro Asp Leu Lys Lys Glu Ser
    50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
            100                 105                 110

Met Val Trp Ala Gln Ala Ala Arg Arg Lys Leu Ala Asp Gln Tyr Pro
            115                 120                 125

His Leu His Asn Ala Glu Leu Ser Lys Thr Leu Gly Lys Leu Trp Arg
        130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Ala
            180                 185                 190

Thr Glu Gln Thr His Ile Ser Pro Asn Ala Ile Phe Lys Arg Leu Gln
        195                 200                 205

Ala Asp Ser Pro His Ser Ser Gly Met Asn Glu Val His Ser Pro
    210                 215                 220

Gly Lys His Ser Gly Gln Ser Gln Gly Pro Pro Thr Pro Pro Thr Thr
225                 230                 235                 240

Pro Lys Thr Asp Val Gln Pro Gly Lys Ala Asp Leu Lys Arg Glu Gly
                245                 250                 255

Arg Pro Leu Pro Glu Gly Gly Arg Gln Pro Pro Ile Asp Phe Arg Asp
            260                 265                 270

Val Asp Ile Gly Glu Leu Ser Ser Asp Val Ile Ser Asn Ile Glu Thr
        275                 280                 285

Phe Asp Val Asn Glu Phe Asp Gln Tyr Leu Pro Pro Asn Gly His Pro
    290                 295                 300

Gly Val Pro Ala Thr His Gly Gln Val Thr Tyr Thr Gly Ser Tyr Gly
305                 310                 315                 320

Ile Ser Ser Thr Ala Ala Thr Pro Ala Gly Ala Gly His Val Trp Met
                325                 330                 335

Ser Lys Gln Gln Ala Pro Pro Pro Pro Pro Pro Pro Gln Gln Ser
            340                 345                 350

Pro Gln Ala Pro Pro Gln Pro Gln Ala Pro Pro Gln Ala Pro Gln
        355                 360                 365

Ala Pro Pro Gln Pro Gln Pro Ala Pro Gln Pro Gln Ala Ala His
    370                 375                 380

Thr Leu Thr Pro Leu Ser Ser Glu Pro Gly Gln Ala Gln Arg Thr His
385                 390                 395                 400

Ile Lys Thr Glu Gln Leu Ser Pro Ser His Tyr Ser Glu Gln Gln Gln
```

```
                405                 410                 415
His Ser Pro Gln Gln Ile Ala Tyr Ser Pro Phe Ser Leu Pro His Tyr
            420                 425                 430

Ser Pro Ser Tyr Pro Pro Ile Thr Arg Ser Gln Tyr Asp Tyr Thr Asp
        435                 440                 445

His Gln Asn Ser Gly Ser Tyr Tyr Ser His Ala Ala Gly Gln Gly Ser
    450                 455                 460

Ser Leu Tyr Ser Thr Phe Thr Tyr Met Asn Pro Ala Gln Arg Pro Met
465                 470                 475                 480

Tyr Thr Pro Ile Ala Asp Thr Ser Gly Val Pro Ser Ile Pro Gln Thr
                485                 490                 495

His Ser Pro Gln His Trp Glu Gln Pro Val Tyr Thr Gln Leu Thr Arg
            500                 505                 510

Pro

<210> SEQ ID NO 7
<211> LENGTH: 1524
<212> TYPE: DNA
<213> ORGANISM: Mus musculus

<400> SEQUENCE: 7
atgaatctcc tggacccctt catgaagatg accgacgagc aggagaaggg cctgtctggc      60
gcccccagcc ccaccatgtc ggaggactcg gctggttcgc cctgtccctc gggctccggc     120
tcggacacgg agaacacccg gccccaggag aacaccttcc caagggcga gccggatctg      180 aagaaggaga gcgaggaaga taagttcccc gtgtgcatcc gcgaggcggt cagccaggtg     240
ctgaagggct acgactggac gctggtgccc atgcccgtgc gcgtcaacgg ctccagcaag     300
aacaagccac acgtcaagcg acccatgaac gccttcatgg tgtgggcgca ggctgcgcgc     360
aggaagctgg cagaccagta cccgcatctg cacaacgcgg agctcagcaa gactctgggc     420
aagctctgga ggctgctgaa cgagagcgag aagagaccct cgtggagga ggcggagcgg      480 ctgcgcgtgc agcacaagaa agaccacccc gattacaagt accagccccg gcggaggaag     540
tcggtgaaga acggacaagc ggaggccgaa gaggccacgg aacagactca catctctcct     600
aatgctatct tcaaggcgct gcaagccgac tccccacatt cctcctccgg catgagtgag     660
gtgcactccc cggcgagca ctctgggcaa tctcagggtc cgccgacccc acccaccact      720
cccaaaaccg acgtgcaagc tggcaaagtt gatctgaagc gagaggggcg ccctctggca     780 gagggggca gacagccccc catcgacttc cgcgacgtgg acatcggtga actgagcagc      840
gacgtcatct ccaacattga accttcgac gtcaatgagt ttgaccaata cttgccaccc      900
aacggccacc aggggttcc ggccaccac ggccaggtca cctacactgg cagttacggc       960
atcagcagca ccgcacccac ccctgcgacc gcgggccacg tgtggatgtc gaagcagcag    1020
gcgccgcccc ctcctccgca gcagcctccg caggccccgc aagccccaca ggcgcctccg    1080
cagcagcaag caccccgca gcagccgcag gcacccagc agcagcaggc acacacgctc     1140
accacgctga gcagcgagcc aggccagtcc cagcgaacgc acatcaagac ggagcagctg    1200
agccccagcc actacagcga gcagcagcag cactccccgc aacagatctc ctacagcccc    1260
ttcaaccttc ctcactacag cccctcctac ccgcccatca cccgctcgca atacgactac    1320
gctgaccatc agaactccgg ctcctactac agtcacgcag ccggccaggg ctcagggctc    1380
tactccacct tcacttacat gaaccccgcg cagcgcccca tgtacacccc catcgctgac    1440
acctccgggg tcccttccat cccgcagacc cacagcccgc agcactggga acaaccagtc    1500
```

```
tacacacagc tcaccagacc ctga                                          1524
```

<210> SEQ ID NO 8
<211> LENGTH: 507
<212> TYPE: PRT
<213> ORGANISM: Mus musculus

<400> SEQUENCE: 8

```
Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
        35                  40                  45

Gln Glu Asn Thr Phe Pro Lys Gly Glu Pro Asp Leu Lys Lys Glu Ser
    50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
            100                 105                 110

Met Val Trp Ala Gln Ala Ala Arg Arg Lys Leu Ala Asp Gln Tyr Pro
        115                 120                 125

His Leu His Asn Ala Glu Leu Ser Lys Thr Leu Gly Lys Leu Trp Arg
    130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
            180                 185                 190

Thr Glu Gln Thr His Ile Ser Pro Asn Ala Ile Phe Lys Ala Leu Gln
        195                 200                 205

Ala Asp Ser Pro His Ser Ser Ser Gly Met Ser Glu Val His Ser Pro
    210                 215                 220

Gly Glu His Ser Gly Gln Ser Gln Gly Pro Pro Thr Pro Pro Thr Thr
225                 230                 235                 240

Pro Lys Thr Asp Val Gln Ala Gly Lys Val Asp Leu Lys Arg Glu Gly
                245                 250                 255

Arg Pro Leu Ala Glu Gly Gly Arg Gln Pro Pro Ile Asp Phe Arg Asp
            260                 265                 270

Val Asp Ile Gly Glu Leu Ser Ser Asp Val Ile Ser Asn Ile Glu Thr
        275                 280                 285

Phe Asp Val Asn Glu Phe Asp Gln Tyr Leu Pro Pro Asn Gly His Pro
    290                 295                 300

Gly Val Pro Ala Thr His Gly Gln Val Thr Tyr Thr Gly Ser Tyr Gly
305                 310                 315                 320

Ile Ser Ser Thr Ala Pro Thr Pro Ala Thr Ala Gly His Val Trp Met
                325                 330                 335

Ser Lys Gln Gln Ala Pro Pro Pro Pro Gln Gln Pro Pro Gln Ala
            340                 345                 350

Pro Gln Ala Pro Gln Ala Pro Pro Gln Gln Ala Pro Pro Gln Gln
        355                 360                 365
```

```
Pro Gln Ala Pro Gln Gln Gln Ala His Thr Leu Thr Thr Leu Ser
    370                 375             380

Ser Glu Pro Gly Gln Ser Gln Arg Thr His Ile Lys Thr Glu Gln Leu
385                 390                 395                 400

Ser Pro Ser His Tyr Ser Glu Gln Gln Gln His Ser Pro Gln Gln Ile
                405                 410                 415

Ser Tyr Ser Pro Phe Asn Leu Pro His Tyr Ser Pro Ser Tyr Pro Pro
                420                 425                 430

Ile Thr Arg Ser Gln Tyr Asp Tyr Ala Asp His Gln Asn Ser Gly Ser
        435                 440                 445

Tyr Tyr Ser His Ala Ala Gly Gln Gly Ser Gly Leu Tyr Ser Thr Phe
    450                 455                 460

Thr Tyr Met Asn Pro Ala Gln Arg Pro Met Tyr Thr Pro Ile Ala Asp
465                 470                 475                 480

Thr Ser Gly Val Pro Ser Ile Pro Gln Thr His Ser Pro Gln His Trp
                485                 490                 495

Glu Gln Pro Val Tyr Thr Gln Leu Thr Arg Pro
                500                 505
```